US012699906B2

(12) United States Patent (10) Patent No.: US 12,699,906 B2
Lanman et al. (45) **Date of Patent: *Aug. 4, 2026**

(54) IDENTIFICATION OF SOMATIC OR GERMLINE ORIGIN FOR CELL-FREE DNA

(71) Applicants:GUARDANT HEALTH, INC., Redwood City, CA (US); Dana-Farber Cancer Institute, Inc., Boston, MA (US)

(72) Inventors: Richard B. Lanman, Los Altos, CA (US); Geoffrey R. Oxnard, Boston, MA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 1168 days.

This patent is subject to a terminal disclaimer.

(21) Appl. No.: 16/678,060

(22) Filed: Nov. 8, 2019

(65) Prior Publication Data

US 2020/0202224 A1 Jun. 25, 2020

Related U.S. Application Data

(63) Continuation of application No. PCT/US2018/033038, filed on May 16, 2018.

(60) Provisional application No. 62/507,127, filed on May 16, 2017.

(51) Int. Cl.
| | |
|---|---|
| *G06N 3/123* | (2023.01) |
| *C12Q 1/6869* | (2018.01) |
| *G16B 20/10* | (2019.01) |
| *G16B 20/20* | (2019.01) |
| *G16B 30/10* | (2019.01) |
| *G16B 30/20* | (2019.01) |
| *G16B 40/20* | (2019.01) |

(52) U.S. Cl.
CPC ........... *G06N 3/123* (2013.01); *C12Q 1/6869* (2013.01); *G16B 20/10* (2019.02); *G16B 20/20* (2019.02); *G16B 30/10* (2019.02); *G16B 30/20* (2019.02); *G16B 40/20* (2019.02)

(58) Field of Classification Search
None
See application file for complete search history.

(56) References Cited

U.S. PATENT DOCUMENTS

| | | | |
|---|---|---|---|
| 6,582,908 | B2 | 6/2003 | Fodor et al. |
| 2001/0053519 | A1 | 12/2001 | Fodor et al. |
| 2003/0152490 | A1 | 8/2003 | Trulson et al. |
| 2011/0160078 | A1 | 6/2011 | Fodor et al. |
| 2013/0288244 | A1 | 10/2013 | Deciu et al. |
| 2014/0100121 | A1 | 4/2014 | Lo et al. |
| 2014/0296081 | A1 | 10/2014 | Diehn et al. |
| 2015/0368708 | A1 | 12/2015 | Talasaz |
| 2016/0201131 | A1 | 7/2016 | Wang et al. |
| 2016/0232290 | A1 | 8/2016 | Rava et al. |
| 2017/0058332 | A1 | 3/2017 | Kermani et al. |
| 2017/0073774 | A1 | 3/2017 | Lo et al. |
| 2018/0251848 | A1 | 9/2018 | Diehn et al. |
| 2020/0202224 | A1 | 6/2020 | Lanman et al. |
| 2023/0245788 | A1 | 8/2023 | Colley et al. |

FOREIGN PATENT DOCUMENTS

| | | | |
|---|---|---|---|
| JP | 2015535681 | A | 12/2015 |
| WO | 2013142389 | A1 | 9/2013 |
| WO | 2014151117 | A1 | 9/2014 |
| WO | 2015164432 | A1 | 10/2015 |
| WO | 2016109452 | A1 | 7/2016 |
| WO | 2016127944 | A1 | 8/2016 |
| WO | 2016149261 | A1 | 9/2016 |

OTHER PUBLICATIONS

Kamps, R., Brandão, R.D., van den Bosch, B.J., Paulussen, A.D., Xanthoulea, S., Blok, M.J. and Romano, A., Jan. 2017. Next-generation sequencing in oncology: genetic diagnosis, risk prediction and cancer classification. International journal of molecular sciences, 18(2), 308, p. 1-54. (Year: 2017).*

Bennett, C.W., Berchem, G., Kim, Y.J. and El-Khoury, V., 2016. Cell-free DNA and next-generation sequencing in the service of personalized medicine for lung cancer. Oncotarget, 7(43), p. 71013-71035. (Year: 2016).*

Lanman et al., 2015. Analytical and clinical validation of a digital sequencing panel for quantitative, highly accurate evaluation of cell-free circulating tumor DNA. PloS one, 10(10), p. e0140712, pp. 1-27 . (Year: 2015).*

Kockan, C., Hach, F., Sarrafi, I., Bell, R.H., McConeghy, B., Beja, K., Haegert, A., Wyatt, A.W., Volik, S.V., Chi, K.N. and Collins, C.C., Jan. 2017. SiNVICT: ultra-sensitive detection of single nucleotide variants and indels in circulating tumour DNA. Bioinformatics, 33(1), pp. 26-34. (Year: 2017).*

Morozova, O. and Marra, M.A., 2008. Applications of next-generation sequencing technologies in functional genomics. Genomics, 92(5), pp. 255-264. (Year: 2008).*

Extended European search report and opinion dated Apr. 19, 2021 for EP Application No. 18802961.5.

Goode, D.L. et al. "A simple consensus approach improves somatic mutation prediction accuracy" Genome Med j (2013) 5(9):90.

Henaff, E. et al. "Jitterbug: Somatic and Germline Transposon Insertion Detection at Single-Nucleotide Resolution" BMC Genomics Oct. 12, 2015 16(768):1-16; p. 3, col. 2, paragraph 1; DOI:1186/s12864-015-1975-5.

International search report and written opinion dated Aug. 31, 2018 for PCT/US2018/033038.

(Continued)

*Primary Examiner* — G. Steven Vanni
*Assistant Examiner* — Meredith Abbott Vassell
(74) *Attorney, Agent, or Firm* — Stephen W. Chen

(57) ABSTRACT

The present disclosure provides systems and methods to detect somatic or germline variants from cell-free DNA (cfDNA). Generally, the systems and methods comprise receiving sequencing information from cfDNA from said subject, determining whether measures are above or below a threshold; and classifying each as being of somatic origin or classifying each locus as being of germline origin.

30 Claims, 16 Drawing Sheets

Specification includes a Sequence Listing.

(56)                    References Cited

OTHER PUBLICATIONS

Xu, H. et al. "Comparison of Somatic Mutation Calling Methods in Amplicon and Whole Exam Sequence Data" BMC Genomics Mar. 28, 2014; 15(244):1-10; p. 4, col. 2, paragraph 1; figures 2-3; DOI:10.1186/1471-2164-15-244.

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Hu, Y. et al. "Discrimination of Germline EGFR T790M Mutations in Plasma Cell-Free DNA Allows Study of Prevalence Across 31,414 Cancer Patients" Clin Cancer Res. Dec. 2017; 23(23): 7351-7359.

International search report and written opinion dated Feb. 5, 2019 for PCT/US2019/052087.

Kockan, C. et al. "SiNVICT: ultra-sensitive detection of single nucleotide variants and indels in circulating tumour DNA" Bioinformatics (2017) 33(1):26-34.

Lek, M et al. "Analysis of protein-coding genetic variation in 60,706 humans" Nature. Aug. 2016; 536(7616): 285-291.

Murtaza, M. et al. "Non-invasive analysis of acquired resistance to cancer therapy by sequencing of plasma DNA" Nauter (May 2013) 497(7447):108-112.

Newman, et al. An ultrasensitive method for quantitating circulating tumor DNA with broad patient coverage. Nat Med. May 2014;20(5):548-54. doi: 10.1038/nm.3519. Epub Apr. 6, 2014.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415DOI: 10.1126/scitranslmed.aan2415.

Schrader, K.A. et al. "Germline Variants in Targeted Tumor Sequencing Using Matched Normal DNA" JAMA Oncol (2016) 2(1):104-111.

Shiraishi, Y. et al. "An empirical Bayesian framework for somatic mutation detection from cancer genome sequencing data" Nucl Acids Res (2013) 41(7):e89.

Skelly, D.A. et al. "A powerful and flxible statistical framework for testing hypotheses of allele-specific gene expression from RNA-seq data" Gen Res (2011) 1728-1737.

Smith, K.S. et al. "SomVarIUS: somatic variant identification from unpaired tissue samples" Bioinformatics (2016) 32(6):808-813.

Sun, J.X. et al. "A computational approach to distinguish somatic vs. germline origin of genomic alterations from deep sequencing of cancer specimens without a matched normal" PLoS Comp Bio (2018) 14(2):e1005965.

Office Action in Japanese Patent Application No. 2019-563118, dated Feb. 7, 2022.

Hassan, M. et al. "Innovations in Genomics and Big Data Analytics for Personalized Medicine and Health Care: A Review" J Mol. Sci (2022) 23(4645):1-17.

Office Action for U.S. Appl. No. 19/098,448, dated Jul. 1, 2025.

Office Action for U.S. Appl. No. 19/170,988 dated Jun. 24, 2025.

Frenel, J.S. et al. "Serial Next-Generation Sequencing of Circulating Cell-Free DNA Evaluating Tumor Clone Response To Molecularly Targeted Drug Administration" Clin Canc Res (2015) 21(20):4586-4596.

Garcia-Murillas, I. et al. "Mutation tracking in circulating tumor DNA predicts relapse in early breast cancer" Science (2015) 7(302): pp. 302ra133.

Siravegna, G. et al. "Clonal evolution and resistance to EGFR blockade in the blood of colorectal cancer patients" Nature Medicine (2015) 21(7):795-801.

Final Office Action for U.S. Appl. No. 19/098,448, dated Oct. 22, 2025.

Final Office Action for U.S. Appl. No. 19/170,988 dated Oct. 8, 2025.

Krampis, et al., "A review of Cloud Computing Bioinformatics Solutions for Next-Gen Sequencing Data Analysis and Research", Methods Next-Generation Seq. (2015) 2:23-34.

Ocana, et al., "Parallel computing in genomic research: advances and applications" Advances and Applications in Bioinformatics and Chemistry (2015) , 8:23-35.

Office Action for U.S. Appl. No. 19/170,971, dated Aug. 19, 2025.

Office Action for U.S. Appl. No. 19/170,982 dated Aug. 12, 2025.

Final Office Action for U.S. Appl. No. 19/170,982 dated Dec. 15, 2025.

Office Action for U.S. Appl. No. 19/098,448, dated Mar. 13, 2026.

Lennon, N.J. et al. "Technological considerations for genome-guided diagnosis and management of cancer" Gen Med (2016) 8:112.

Office Action for U.S. Appl. No. 19/440,954 dated Apr. 22, 2026.

Siravegna, G. et al. "Integrating liquid biopsies into the management of cancer" Nature Reviews Clinical Oncology (2017) 14:531-548.

* cited by examiner

|  | Germline T790M detected | No germline T790M detected |
|---|---|---|
| Total | 48 | 31,366 |
| Nonsquamous NSCLC | 43 (90%) | 12,731 (41%) |
| Other cancers | 5 (10%) | 18,635 (59%) |

FIG. 6A

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcagcatgtc aagatcacag att                                          23

<210> SEQ ID NO 2
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
cctccttctg catggtattc tttct                                                   25

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
agtttggcca gcccaa                                                             16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
agtttggccc gcccaa                                                             16

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtgagaaagt taaaattccc gtc                                                     23

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cacacagcaa agcagaaac                                                          19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
atcgaggatt tccttgttg                                                          19

<210> SEQ ID NO 8
<211> LENGTH: 22
<212> TYPE: DNA
<213> ORGANISM: Artificial Sequence
<220> FEATURE:
```

-continued

```
<223> OTHER INFORMATION: Description of Artificial Sequence: Synthetic
      probe

<400> SEQUENCE: 8
aggaattaag agaagcaaca tc                                              22

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcctgctggg catctg                                                    16

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctttgtgtt cccggacata gtc                                            23

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
atgagctgcg tgatgag                                                   17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
atgagctgca tgatgag                                                   17
```

IDENTIFICATION OF SOMATIC OR GERMLINE ORIGIN FOR CELL-FREE DNA

CROSS-REFERENCE

This application is a continuation of International Application No. PCT/US2018/033038, filed May 16, 2018, which claims the benefit of U.S. Provisional Application No. 62/507,127, filed May 16, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 30, 2020, is named GH0025US-CON_SL.txt and is 3,080 bytes in size.

BACKGROUND

Comparison of the genome of a subject and a reference genome (e.g., GRCh38.p4), will typically show differences (genetic variation) at about 0.01% of bases. Genetic variants in the germline can represent SNPs transferred through normal heredity or through germinal mutations. Variations can exist in homozygous or heterozygous form.

Certain pathological states, such as cancer, are characterized by genetic variations in the genomes of pathological cells as compared to the germline genome. These variations result from mutation in somatic cells, and are referred to as somatic mutations.

Polynucleotides harboring somatic mutations can be detected in cell-free DNA (cfDNA), where they are mixed with DNA from cells having the germline genome. Where a large background (germline) is present in cfDNA, no computer implemented process can differentiate germline variants from somatic mutations automatically. Instead, conventional systems rely on the expertise of an individual human expert or a consortium of experts (in either case called a Tumor Board) to distinguish somatic mutations from the germline ones.

If noise and biases were to be absent, the germline variants would be those with an allelic fraction of 50% (in the case of heterozygous (het) loci) or 100% (in the case of homozygous (homo) loci). However, in practice, the existence of noise and biases in the system make these crisp numbers fuzzy. In other words, the het or homo loci are not detected at exactly 50% or 100%, but are instead between lower and upper confidence bounds for each of the het and homo categories. For example, a het locus could be in the range of 40% to 60%, while a homo locus could be in the range of 98% to 100%.

SUMMARY

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

In one aspect, the present disclosure provides a method for identifying somatic origin of each of a plurality of genomic loci in cell-free DNA (cfDNA) from a subject, said method comprising: receiving sequencing information from said cfDNA from said subject, said sequencing information comprising cfDNA sequencing reads from said plurality of genomic loci; determining quantitative allele fraction (AF) measures for each of said plurality of genomic loci based on said cfDNA sequencing reads; determining a standard deviation (STDEV) for each of said AF measures; providing a STDEV threshold and an AF threshold; determining whether each of said AF measures has a STDEV above or below said STDEV threshold; determining whether each of said AF measures is above or below said AF threshold; and classifying each locus with a STDEV below said STDEV threshold and an AF measure below said AF threshold below as being of somatic origin.

In one aspect, the present disclosure provides a method for identifying germline origin of each of a plurality of genomic loci in cell-free DNA (cfDNA) from a subject, said method comprising: receiving sequencing information from said cfDNA from said subject, said sequencing information comprising cfDNA sequencing reads from said plurality of genomic loci; determining quantitative allele fraction (AF) measures for each of said plurality of genomic loci based on said cfDNA sequencing reads; determining a standard deviation (STDEV) for each of said AF measures; providing a STDEV threshold and an AF threshold; determining whether each of said AF measures has a STDEV above or below said STDEV threshold; determining whether each of said AF measures is above or below said AF threshold; and classifying each locus with a STDEV below said STDEV threshold and an AF measure above said AF threshold below as being of germline origin.

In some embodiments, an AF measure for a genomic locus below said STDEV threshold indicates low copy number variation (CNV) for said genomic locus.

In some embodiments, an AF measure for a genomic locus above said STDEV threshold indicates high copy number variation (CNV) for the associated genomic locus.

In some embodiments, an AF threshold is determined empirically.

In one aspect, the present disclosure provides a method for identifying somatic origin of each of a plurality of genomic loci in cell-free DNA (cfDNA) from a subject with cancer, said method comprising: receiving sequencing information from said cfDNA from said subject at a first time point before treatment with a cancer therapeutic, said sequencing information comprising a first set of cfDNA sequencing reads from said plurality of genomic loci; receiving sequencing information from said cfDNA from said subject at a second time point after treatment with a cancer therapeutic, said sequencing information comprising a second set of cfDNA sequencing reads from said plurality of genomic loci; determining quantitative allele fraction (AF) measures for each of said plurality of genomic loci based on said cfDNA sequencing reads at said first time point and based on said cfDNA sequencing reads at said second time point; comparing said AF measures from said first time point and from said second time point; wherein said cancer is responsive to said cancer therapeutic; and identifying a genomic locus as being of somatic origin if an AF measure from said genomic locus decreases between said first time point and said second time point.

In one aspect, the present disclosure provides a method for identifying germline origin of each of a plurality of genomic loci in cell-free DNA (cfDNA) from a subject with cancer, said method comprising: receiving sequencing information from said cfDNA from said subject at a first time point before treatment with a cancer therapeutic, said sequencing information comprising a first set of cfDNA sequencing reads from said plurality of genomic loci; receiving sequencing information from said cfDNA from said subject at a second time point after treatment with a cancer therapeutic, said sequencing information comprising a second set of cfDNA sequencing reads from said plurality of genomic loci; determining quantitative allele fraction (AF) measures for each of said plurality of genomic loci based on said cfDNA sequencing reads at said first time point and based on said cfDNA sequencing reads at said second time point; comparing said AF measures from said first time point and from said second time point; wherein said cancer is responsive to said cancer therapeutic; and identifying a genomic locus as being of germline origin if an AF measure from said genomic locus does not decrease between said first time point and said second time point.

In one aspect, the present disclosure provides a method for identifying somatic or germline origin of each of a plurality of genomic loci in cell-free DNA (cfDNA) from a subject, said method comprising: receiving sequencing information from said cfDNA from said subject gathered at a first time point, said sequencing information comprising first cfDNA sequencing reads; providing sequence information from said plurality of genomic loci; performing a binning of each of said plurality of genomic loci, wherein said binning comprises assigning an initial classification for each genomic locus in said plurality of genomic loci, said initial classification selected from the group consisting of: a) presumed somatic origin; b) presumed germline origin; or c) indeterminate origin; thereby generating a first bin comprising genomic loci of presumed somatic origin, a second bin comprising genomic loci of presumed germline origin, and a third bin comprising genomic loci of indeterminate origin; determining, for each of said genomic regions in said first bin, said second bin, and said third bin, a quantitative allele fraction (AF) measure based on said first cfDNA sequencing reads to generate a first AF set, a second AF set, and a third AF set, respectively; generating a first frequency distribution based on said first AF set and a second frequency distribution based on said second AF set, wherein no overlap exists between said first frequency distribution and said second frequency distribution; identifying an AF threshold value based on said first and second frequency distributions, which AF threshold value is (i) no less than the largest quantitative AF measure among said first AF set and (ii) no more than the smallest quantitative AF measure among said second AF set; and assigning a final classification for each of said third bin of genomic loci, which final classification is (A) presumed somatic origin if said genomic locus has a quantitative AF measure no more than said AF threshold value, or (B) presumed germline origin if said genomic region has a quantitative AF measure no less than said AF threshold value.

In one aspect, the present disclosure provides a method for identifying somatic or germline origin of each of a plurality of genomic loci in cell-free DNA (cfDNA) from a subject, said method comprising: receiving sequencing information from said cfDNA from said subject gathered at a first time point, said sequencing information comprising first cfDNA sequencing reads; providing sequence information from said plurality of genomic loci; performing a binning of each of said plurality of genomic loci in said plurality of genomic loci, wherein said binning comprises assigning an initial classification for each genomic locus in said plurality of genomic loci, said initial classification selected from the group consisting of: a) presumed somatic origin; b) presumed germline origin; or c) indeterminate origin; thereby generating a first bin comprising genomic loci of presumed somatic origin, a second bin comprising genomic loci of presumed germline origin, and a third bin comprising genome loci of indeterminate origin; determining, for each of said genomic regions in said first bin, said second bin, and said third bin, a quantitative allele fraction (AF) measure based on said first cfDNA sequencing reads to generate a first AF set, a second AF set, and a third AF set, respectively; generating a first frequency distribution based on said first AF set and a second frequency distribution based on said second AF set, wherein an overlap exists between said first frequency distribution and said second frequency distribution; identifying a first AF threshold value based on said first and second frequency distributions, which first AF threshold value is the largest quantitative AF measure among said first AF set; identifying a second AF threshold value based on said first and second frequency distributions, which second AF threshold value is the smallest quantitative AF measure among said second AF set; and assigning a final classification for each of said plurality of genomic loci, wherein said final classification is (A) presumed somatic origin if said genomic region has a quantitative AF measure no more than said first AF threshold value, (B) presumed germline origin if said genomic region has a quantitative AF measure no less than said second AF threshold value, or (C) ambiguous if said genomic region has a quantitative AF measure greater than said first AF threshold value and less than said second AF threshold value.

In one aspect, the present disclosure provides a method for identifying somatic origin of each of a plurality of genomic loci in cell-free DNA (cfDNA) from a subject, said method comprising: receiving sequencing information from said cfDNA from said subject, said sequencing information comprising a set of cfDNA sequencing reads from said plurality of genomic loci; determining a first set of quantitative allele fraction (AF) measures, said first set of AF measures comprising AF measures for each of said plurality of genomic loci based on said cfDNA sequencing reads; providing a second set of AF measures, said second set of AF measures comprising AF measures for each of one or more known somatic variants; comparing an AF measure from a genomic locus from said first set of AF measures to an AF measure from said second set of AF measures; identifying a genomic locus as being of somatic origin if there is a difference of 10% or less between said AF measure from said first set of AF measures for a genomic locus and said AF measure from said second set of AF measures.

In some embodiments, said second set of AF measures comprises AF measures from a second plurality of genomic loci based on said cfDNA sequencing reads.

In some embodiments, said second set of AF measures comprises AF measures from a plurality of genomic loci from cfDNA from a plurality of control subjects.

In one aspect, the present disclosure provides a method for identifying germline origin of each of a plurality of genomic loci in cell-free DNA (cfDNA) from a subject, said method comprising: receiving sequencing information from said cfDNA from said subject, said sequencing information comprising a set of cfDNA sequencing reads from said plurality of genomic loci; determining a first set of quantitative allele fraction (AF) measures, said first set of AF measures comprising AF measures for each of said plurality of genomic loci based on said cfDNA sequencing reads;

providing a second set of AF measures, said second set of AF measures comprising AF measures for each of one or more known somatic variants; comparing an AF measure from a genomic locus from said first set of AF measures to an AF measure from said second set of AF measures; identifying a genomic locus as being of germline origin if there is a difference of greater than 10% between said AF measure from said first set of AF measures for a genomic locus and said AF measure from said second set of AF measures.

In some embodiments, said second set of AF measures comprises AF measures from a second plurality of genomic loci based on said cfDNA sequencing reads.

In some embodiments, said second set of AF measures comprises AF measures from a plurality of genomic loci from cfDNA from a plurality of control subjects.

In one aspect, the present disclosure provides a method for identifying germline origin of each of a plurality of genomic loci in cell-free DNA (cfDNA) from a subject, said method comprising: receiving sequencing information from said cfDNA from said subject, said sequencing information comprising a set of cfDNA sequencing reads from said plurality of genomic loci; determining a first set of quantitative allele fraction (AF) measures, said first set of AF measures comprising AF measures for each of said plurality of genomic loci based on said cfDNA sequencing reads; providing a second set of AF measures, said second set of AF measures comprising AF measures for each of one or more known germline variants; comparing an AF measure from a genomic locus from said first set of AF measures to an AF measure from said second set of AF measures; identifying a genomic locus as being of germline origin if there is a difference of 10% or less between said AF measure from said first set of AF measures for a genomic locus and said AF measure from said second set of AF measures.

In some embodiments, said second set of AF measures comprises AF measures from a second plurality of genomic loci based on said cfDNA sequencing reads.

In some embodiments, said second set of AF measures comprises AF measures from a plurality of genomic loci from cfDNA from a plurality of control subjects.

In one aspect, the present disclosure provides a method for identifying somatic origin of each of a plurality of genomic loci in cell-free DNA (cfDNA) from a subject, said method comprising: receiving sequencing information from said cfDNA from said subject, said sequencing information comprising a set of cfDNA sequencing reads from said plurality of genomic loci; determining a first set of quantitative allele fraction (AF) measures, said first set of AF measures comprising AF measures for each of said plurality of genomic loci based on said cfDNA sequencing reads; providing a second set of AF measures, said second set of AF measures comprising AF measures for each of one or more known germline variants; comparing an AF measure from a genomic locus from said first set of AF measures to an AF measure from said second set of AF measures; identifying a genomic locus as being of somatic origin if there is a difference of greater than 10% between said AF measure from said first set of AF measures for a genomic locus and said AF measure from said second set of AF measures.

In some embodiments, said second set of AF measures comprises AF measures from a second plurality of genomic loci based on said cfDNA sequencing reads.

In some embodiments, said second set of AF measures comprises AF measures from a plurality of genomic loci from cfDNA from a plurality of control subjects.

In some embodiments, one or more of said genomic loci is a locus in a BRCA gene.

In one aspect, the present disclosure provides a method comprising: a) providing a set of sequence reads of cfDNA molecules, wherein the sequence reads map to a selected genomic region of a reference genome (e.g., a gene, an exon, an intron, a portion of a gene (e.g., at least 100 nucleotides, at least 500 nucleotides, or at least 1000 nucleotides)); b) determining allele frequency of a set comprising a plurality of genetic variants (e.g., nucleotides that differ from the reference sequence) within the genomic region, wherein the set includes a variant of interest; c) determining a measure of variability (e.g., standard deviation or variance) of the allele frequency of the genetic variants in the set; d) providing a measure of variability threshold and an allele frequency threshold; e) determining if the measure of variability is below the variability threshold; and f) if the measure of variability is below the variability threshold: (i) call the variant of interest as having germline origin if the allele frequency of the variant of interest is above the allele frequency threshold, and (ii) call the variant of interest as having somatic origin if the allele frequency of the variant of interest is below the allele frequency threshold.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5, also shows that, when there is lower copy number variation, it is possible to visually distinguish which cases of germline EGFR T790M (501) are likely germline.

FIG. 6A shows that NGS results reveal that 48 (0.15%) cancer patients from a database of 31,414 unique cancer patients were found to carry a germline EGFR T790M mutation, with non-squamous non-small cell lung cancer (NSCLC) being the dominant diagnosis in these patients.

DETAILED DESCRIPTION

Figure 1:
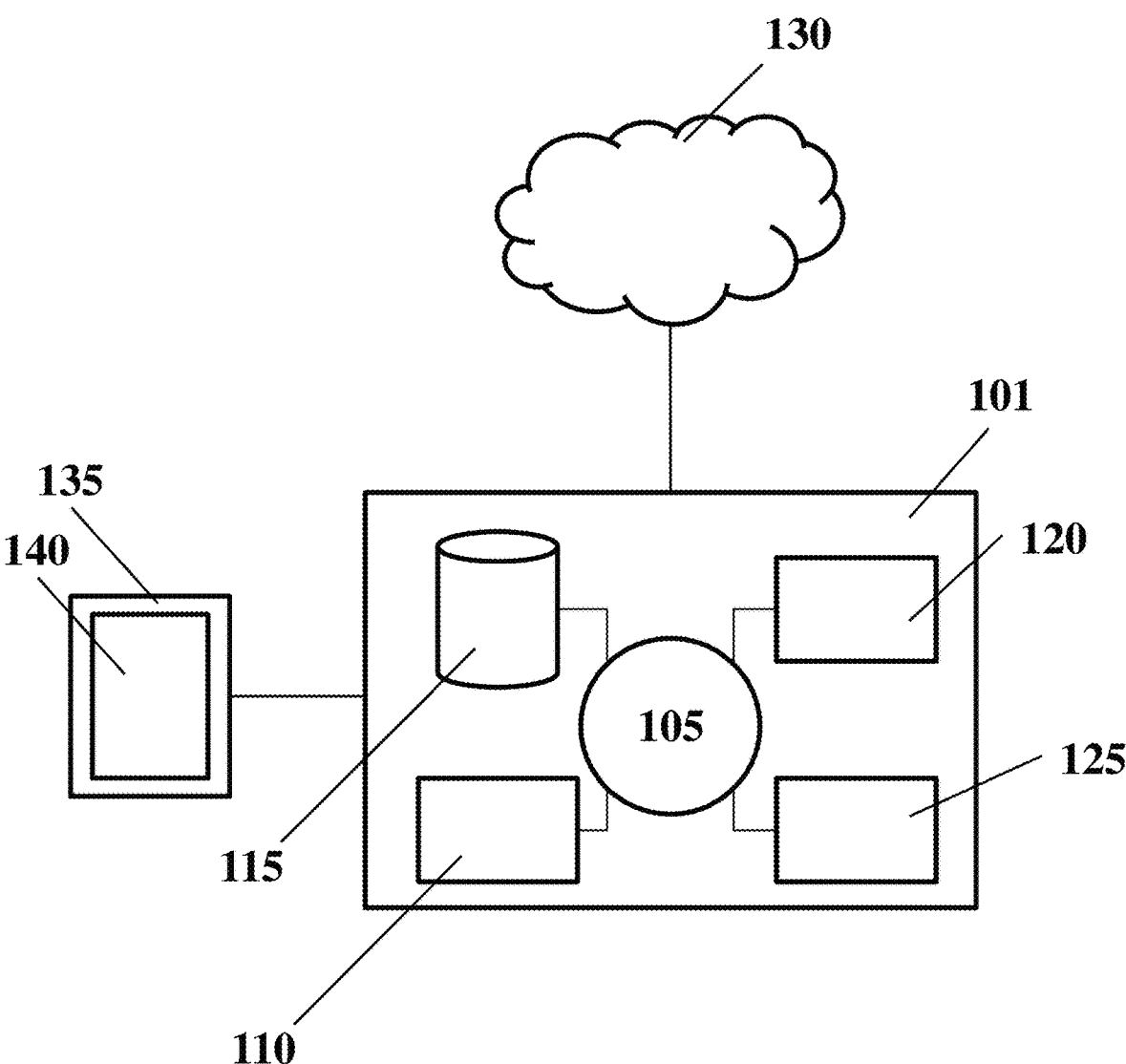
FIG. 1 shows a computer control system that is programmed or otherwise configured to implement methods provided herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present teachings, such that slight and insubstantial equivalents are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or to "one or more." Also, the use of "or" is inclusive, such that the phrase "A or B" is true when "A" is true, "B" is true, or both "A" and "B" are true.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well-known and commonly used in the art.

A "system" sets forth a set of components, real or abstract, comprising a whole where each component interacts with or is related to at least one other component within the whole.

A "biomolecule" may refer to any molecule that is produced by a biological organism, including large polymeric molecules such as proteins, polysaccharides, lipids, and nucleic acids (DNA and RNA), as well as small molecules such as primary metabolites, secondary metabolites, and other natural products.

As used herein, the term "sequencing" refers to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performer by a gene analyzer such as, for example, gene analyzers commercially available from Illumina or Applied Biosystems.

The phrase "next generation sequencing" or NGS refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

The phrase "sequencing run" refers to any step or portion of a sequencing experiment performed to determine some information relating to at least one biomolecule (e.g., a nucleic acid molecule such as DNA or RNA).

DNA (deoxyribonucleic acid) is a chain of nucleotides comprising four types of nucleotides; adenine (A), thymine (T), cytosine (C), and guanine (G). RNA (ribonucleic acid) is a chain of nucleotides comprising four types of nucleotides; A, uracil (U), G, and C. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "nucleotide sequence", "genomic sequence," "genetic sequence," or "fragment sequence," or "nucleic acid sequencing read" denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The terms "adaptor(s)", "adapter(s)" and "tag(s)" are used synonymously throughout this specification. An adaptor or tag can be coupled to a polynucleotide sequence to be "tagged" by any approach including ligation, hybridization, or other approaches.

As used herein, a common variant has at least 5% of GMAF (global minor allele frequency), while a low-frequency variant has about 0.1-5% of GMAF, and a rare variant has 0.5% or less GMAF, where GMAF is a frequency at which the least common allele occurs in a given population.

As used herein, "genotype" refers to allelic identity at a genetic locus on one or more germline chromosomes. This includes full genotype (allelic identity on all chromosomes), partial genotype (allelic identity on at least one chromosome) and null genotype (allele(s) not existing on one or more or all chromosomes), including determining homozygosity or heterozygosity at a locus ("allelic designation").

As used herein, a somatic variant indicates the source is a cancerous tissue. As used herein, somatic origin of a genetic variant refers to a genetic variant that first occurs in a somatic cell and not in the germline. This is in contrast to germline variants, which have normal cells as a source. The variation can be passed on to daughter cells through mitotic division. This can result in a group of cells having a genetic difference from the rest of the cells of an organism. Additionally, as the variation does not occur in a germline cell, the mutation will not be inherited by progeny organisms.

SNP can refer to single-nucleotide polymorphism or variation in the population, usually in the context of germline variants, while SNV can refer to single-nucleotide variant and SSNV can refer to somatic single-nucleotide variant (usually used in the context of cancer-associated variants). For an individual, the term SNV is used for variations detected in both somatic (cancerous) and germline (normal) cfDNA.

CNV can refer to copy-number variant (gene-level copy-number mutation, usually resulting from duplication event).

Cell-free DNA (cfDNA) from a subject having cancer comprises DNA both from cells bearing the germline genome (e.g., from "healthy cells") ("germline DNA") and DNA from cancer cells, typically bearing somatic mutations ("cancer DNA"). The relative amounts of germline DNA and cancer DNA in a cell-free DNA sample depends upon how advanced the cancer is. In early stages, only a small amount of the DNA is cancer DNA. This could be, for example, about 1%-5% of the total DNA. Thus, detecting a small amount (e.g., about 1%-5% of the cfDNA in a sample) of a genetic variant such as a minor allele may be indicative of a somatic mutation, and thus, the presence of cancer DNA. However, as the disease progresses and the tumor expands, the amount of cancer DNA in a cell-free DNA sample can increase significantly, for example to more than 25% of the total cell-free DNA. When the percentage of DNA molecules bearing a genetic variant reaches high levels, it may become ambiguous whether the variant represents a somatic mutation originating from cancer cells or represents heterozygosity in the germline DNA.

Genomic analysis of plasma cfDNA can be as a tool for genomic discovery and for aiding delivery of precision cancer medicine, but the shedding of cancer-derived DNA into the plasma can be highly variable and depends upon cancer stage, extent of metastatic spread, and whether the cancer is responding or progressing. In addition, the plasma levels of somatic genomic alterations can be highly dynamic in response to therapy, at times becoming undetectable within two weeks. As a result, in many patients the majority of plasma cfDNA is germline DNA, largely shed from benign hematopoietic or endothelial cells. The present disclosure provides an approach which can distinguish germline variants from cancer-derived somatic variants within cfDNA next generation sequencing (NGS) profiles, thus providing both tumor genotyping for therapy selection as well as germline characterization for the assessment of hereditary risk with a single assay.

The approach provided by the present disclosure has a number of applications. Plasma NGS will, at times, identify incidental germline mutations in cancer patients which have potential clinical implications for patients and their families. Certain germline EGFR mutations described herein are rare risk alleles thought to be associated with inherited cancer risk, and the approaches described herein can be applied to other germline mutations. Other cancer-related genes (e.g. TP53 or BRCA1/2 and mismatch repair genes) can also be sequenced with plasma NGS, and germline mutations in these genes can have profound clinical implications. The present disclosure describes the presence of a suspected germline mutation using a bioinformatic algorithm predicted for a confirmed germline mutation with a high positive predictive value, an important diagnostic performance characteristic for a rule-in test.

Discernment of germline and somatic variants in plasma cfDNA also can impact the understanding of cancer biology. With tumor NGS, it can be difficult to determine if a variant of unknown significance in an oncogene represents a potential driver mutation or a germline polymorphism. In plasma NGS cases without high copy number variation, the present disclosure allows for the differentiation between these two types of genomic alterations with a single (blood) sample, thereby reducing the risk of a germline polymorphism being therapeutically targeted in error. Additionally, in instances where serial plasma genotyping is being used over time to monitor response and resistance to therapy, the ability to distinguish germline and somatic variants in plasma cfDNA can make it easier to accurately track tumor DNA levels.

Tumor mutation burden (TMB) is an emerging biomarker for understanding sensitivity and resistance to immune checkpoint inhibitors. More mutations within a cancer can lead to more cell surface neoantigens for immune stimulation. However, it can be difficult to calculate mutational burden using tumor NGS because germline polymorphisms can be mistaken for potentially antigenic somatic mutations. The present disclosure provides the ability to overcome this challenge, allowing germline and somatic variants to be bioinformatically distinguished and antigenic somatic variants more clearly identified, thereby reducing the chance of a germline polymorphism being mistaken for a potentially antigenic somatic mutation.

The germline DNA of a subject can be homozygous or heterozygous at any genetic locus. Measurements at a locus can take the form of allelic fractions (AFs), which measure the frequency with which an allele is observed in a sample. For a variety of reasons (including, for example, errors in DNA sequencing), in a set of sequence reads generated from cfDNA of a non-cancer subject, read counts for an allelic form (e.g., an SNV) mapping to a genetic locus for which the subject is homozygous may not be exactly 100%. Similarly, read counts for an allelic form mapping to a genetic locus for which the subject is heterozygous may not be exactly 50%. If an individual is homozygous in the germline for a genetic variant (not matching the allele in a reference genome, the percentage of base calls bearing the genetic variant will typically be close to, but not always identical to, 100% of the calls. Similarly, if an individual is heterozygous in the germline for a genetic variant, the percentage of base calls bearing the genetic variant will typically be close to 50%, but could range from, for example, 30% to 70%. Measurements in this range are consistent with heterozygosity at the locus. However, the measurement may make the determination ambiguous. In this case, one may call a genotype at a locus as heterozygous or homogzygous with a certain level of confidence or probability.

Accordingly, if a subject has cancer, and a genetic variant a locus is measured to be in a range consistent with heterozygosity, one's confidence that the variant resulted from a somatic mutation may be decreased as compared to a measurement in a range between homozygosity and heterozygosity. For example, a measurement in the range of 5% to 20% may indicate that a locus contains a genetic variant in an amount too high to be accounted for by homozygosity and too low to be accounted for by heterozygosity. Thus, it is likely that the measurement is a result of a somatic mutation. By contrast, a measurement around 40% may indicate heterozygosity or it may indicate an abundance of DNA containing a somatic mutation (for example, if that somatic mutation has caused a tumor that has contributed a large relative amount of DNA to the sample).

This disclosure provides, inter alia, methods of determining whether the origin of a genetic variant detected in a cell-free DNA sample is more likely germline (e.g., representing heterozygosity in the germline), or somatic (e.g., from cancer). In particular, the present disclosure provides methods that utilize AFs to make this determination.

In some embodiments, the present disclosure provides a method for identifying germline or somatic origin of each of a plurality of genomic loci in cell-free DNA (cfDNA) from a subject with one or more thresholds that can be used to determine whether a variant at a locus is of germline or somatic origin. One exemplary threshold that can be used is a standard deviation (STDEV) threshold. For example, the skilled worker, after determining a quantitative allele fraction (AF) for a genomic locus, can determine a STDEV for the AF measure. As copy number variation (CNV) increases, STDEVs would be expected to increase as well. Thus, low STDEVs can be assumed to have low CNV, making those data easier to process. A STDEV threshold can be used to separate high CNV from low CNV, increasing the predictive power of the method. A second threshold for AF can be used in combination with or as a substitute for the CNV threshold. Because AF measures would be expected to be higher in germline-derived variants than somatic variants, AF measures above an AF threshold can be classified as germline-derived, whereas AF measures below an AF threshold can be classified as somatic-derived. Exemplary AF thresholds include, but are not limited to, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, and about 35%. In some embodiments, an AF threshold is determined empirically.

The methods described herein also can be used to determine whether a locus from cfDNA is of germline or somatic origin based on response to treatment. For example, sequence information can be obtained from a subject with cancer before and after treatment with a cancer therapeutic. If the cancer is responsive to the cancer therapeutic, and a cancer-associated variant at a locus is of somatic origin, its AF should decrease. Thus, AF can be measured before and after treatment, and those values compared, to determine somatic or germline origin. If the AF measure decreases, the variant can be identified as being of somatic origin. If the AF measure does not decrease (i.e., it stays the same or increases), the variant can be identified as being of germline origin.

In some embodiments, the methods described herein can be used to determine whether loci from cfDNA are of germline or somatic origin by binning loci according to an initial classification of presumed somatic origin, presumed germline origin, or indeterminate origin. Quantitative AF measures then can be determined for the loci of each bin to generate AF sets, which are subsequently used to generate frequency distributions for the loci of presumed somatic or germline origin. The distributions can be used to set an AF threshold value, e.g., a threshold value no less than the largest quantitative AF measure among the "presumed somatic" AF set and no more than the smallest quantitative AF measure among the "presumed germline" AF set. Thus, the "indeterminate origin" loci can be classified as germline or somatic based on whether the AF of a locus is above the AF threshold value (and is therefore germline) or below the AF threshold value (and is therefore somatic). Alternatively, when an overlap exists between a frequency distribution for "presumed somatic" AF measures and a frequency distribution for "presumed germline" AF measures, two threshold values can be determined such that a first AF threshold value is the largest quantitative AF measure among the "presumed somatic" AF set and a second AF threshold value is the smallest quantitative AF measure among the "presumed germline" AF set. In such embodiments, loci with quantitative AF measures below the "presumed somatic" threshold are classified as somatic, loci with quantitative AF measures above the "presumed germline" threshold are classified as germline, and loci with quantitative AF measures below the between the two thresholds are classified as ambiguous. These ambiguous loci can then be, for example, assigned a probability for whether they are of germline or somatic origin based on the position of their AF measure in the frequency distribution.

In some embodiments, the present disclosure provides a method for identifying somatic or germline origin of a genomic locus in cfDNA by comparing an AF measure from a genomic locus in a sample to one or more AF measures from known somatic or germline variants. If, for example, AF measures from known somatic variants are used, genomic loci with AF measures that are similar (e.g., within 30%, within 25%, within 20%, within 15%, within 10%, within 9%, within 8%, within 7%, within 6%, within 5%, within 4%, within 3%, within 2%, within 1%, or within 0.1%) can be classified as being of somatic origin, whereas genomic loci with AF measures that are dissimilar (e.g., not within 30%, not within 25%, not within 20%, not within 15%, not within 10%, not within 9%, not within 8%, not within 7%, not within 6%, not within 5%, not within 4%, not within 3%, not within 2%, not within 1%, or not within 0.1%), can be classified as being of germline origin. Likewise, if measures from known germline variants are used, genomic loci with AF measures that are similar (e.g., within 30%, within 25%, within 20%, within 15%, within 10%, within 9%, within 8%, within 7%, within 6%, within 5%, within 4%, within 3%, within 2%, within 1%, or within 0.1%) can be classified as being of germline origin, whereas genomic loci with AF measures that are dissimilar (e.g., not within 30%, not within 25%, not within 20%, not within 15%, not within 10%, not within 9%, not within 8%, not within 7%, not within 6%, not within 5%, not within 4%, not within 3%, not within 2%, not within 1%, or not within 0.1%), can be classified as being of somatic origin. AF measures from known somatic somatic or germline variants can be from cfDNA sequencing reads from the subject being tested or from a plurality of control subjects.

In some embodiments, cell-free DNA from a subject is sequenced and one or more genetic variants are detected and quantified. For example, the relative amount of total reads (number of read counts) mapping to a locus that contain the variant is determined. If the relative amount is consistent with homozygosity, one can have high confidence that the variant is present in the germline. Such an amount could be, for example, above 95%, above 96%, above 97%, above 98%, above 99%, or 100%. This call can be compared with a determined genotype for confirmation.

If the relative amount is inconsistent with a homozygous or heterozygous genotype at the locus, one can have high confidence that the variant the result of a somatic mutation and is not present in the germline. Such an amount could be, for example, below 30%, below 25%, below 20%, below 15%, below 10%, below 9%, below 8%, below 7%, below 6%, below 5%, below 4%, below 3%, below 2%, or below 1%. Again, this call can be compared with a determined genotype for confirmation.

Alternatively, the relative amount can be consistent with heterozygosity at the locus. Such an amount could be, for example, between 30% and 70%, e.g., between 40% and 60%, between 45% and 55%, between 46% and 54%, between 47% and 53%, between 48% and 52%, or between 49% and 51%. In some embodiments, the probable germline genotype (e.g., as obtained from gDNA) of the subject at the locus is determined. In some embodiments, the genotype is compared with the identity of the variant found in the cell-free DNA. In certain embodiments, if the genotype is homozygous, then one can conclude with high confidence that the variant represents a somatic mutation, and most likely in high amounts. If the genotype is determined to be heterozygous, and the variant is consistent with one of the heterozygous alleles, then one may conclude that the variant is not a somatic mutation, but represents heterozygosity in the germline genotype.

In some embodiments, a homozygous genotype can be ruled out with high confidence but a heterozygous genotype cannot be determined with high confidence, resulting in a potentially ambiguous genotype. For example the variant may be measured on the genomic DNA at an extreme end of the range, e.g., at 30%. In such a case, one may not be able to determine, with high confidence, whether the amount of variant detected in the cfDNA is or is not more likely to represent a somatic mutation or germline heterozygosity. Such a measurement may arise when an abundance of DNA containing the somatic mutation is present in a sample because of, for example, the rapid growth of tumor cells. It should be noted that at any measured level, there is some probability that a variant detected in the genomic DNA does not represent heterozygosity. However, between 30% and 70% detection of a variant in the germline most likely represents heterozygosity, and the variant detected in cfDNA can be measured against this.

In such cases, other information can be used in Bayesian fashion to increase or decrease the probability that a variant in the cfDNA represents a somatic mutation or heterozygosity in the germline. For example, population studies can indicate the prevalence of a variant in the germline of various groups, e.g., based in genetic ancestry. So, for example, if one has low confidence in calling a heterozygous genotype in an individual, and the variant is found at high incidence in the persons sharing the subject's genetic ancestry, then one can determine with higher confidence that the person is, indeed, heterozygous and that the variant in the cfDNA does not represent a somatic mutation. Conversely, if the variant is found at only very low incidence in the persons sharing the subject's genetic ancestry, then one can determine with higher confidence that the person is not heterozygous and that the variant in the cfDNA represents a somatic mutation.

This disclosure contemplates several ways to determine whether an amount (e.g., of read counts) is consistent or inconsistent with a heterozygous genotype. In some embodiments, cutoff values are used. For example, a cutoff of 30% of the total read counts for a particular genetic variant at a locus can be set. In some embodiments, values below the cutoff amount are presumed to represent somatic mutations. In some embodiments, values above the cutoff amount, and, typically below a cutoff for homozygosity, may be presumed to be consistent with heterozygosity and, therefore, require further analysis before calling the variant as a somatic mutation.

In some embodiments, a probabilistic function (e.g., a Bayesian function) is used to calculate a probability that an amount represents heterozygosity. Probabilities above certain levels can trigger the comparison genotype.

In some embodiments, the determination of a genotype is made as a routine part of the analysis. In some embodiments, the determination of a genotype is determined only if an abundance of a variant is consistent with an interpretation of heterozygosity.

In some embodiments, the methods of the present disclosure reduce error rates and bias that can be orders of magnitude higher than what is required to reliably detect de novo genomic alterations associated with cancer. In some embodiments, the methods first capture genetic information by collecting body fluid samples as sources of genetic material (blood, saliva, sweat, among others), followed by sequencing the materials. For example, polynucleotides in a sample can be sequenced, producing a plurality of sequence reads. The tumor burden in a sample that comprises polynucleotides can be estimated as the relative number of sequence reads bearing a variant, to the total number of sequence reads generated from the sample. Also, in the case of copy number variants, the tumor burden can be estimated as the relative excess (in the case of gene duplication) or relative deficit (in the case of gene elimination) of total number of sequence reads at test and control loci. So, for example, a run may produce 1000 reads mapping to an oncogene locus, of which 900 correspond to wild type and 100 correspond to a cancer mutant, indicating a copy number variant at this gene. Next, genetic information is processed and genetic variants are identified. Genetic variants include sequence variants, copy number variants and nucleotide modification variants. A sequence variant is a variation in a genetic nucleotide sequence. A copy number variant is a deviation from wild type in the number of copies of a portion of a genome. Genetic variants include, for example, single nucleotide variations (SNPs), insertions, deletions, inversions, transversions, translocations, gene fusions, chromosome fusions, gene truncations, copy number variations (e.g., aneuploidy, partial aneuploidy, polyploidy, gene amplification), abnormal changes in nucleic acid chemical modifications, abnormal changes in epigenetic patterns and abnormal changes in nucleic acid methylation. The process then determines the frequency of genetic variants in the sample containing the genetic material. Since this process is noisy, the process separates information from noise.

The sequencing methods have error rates. For example, the mySeq system of Illumina can produce percent error rates in the low single digits. Thus, for 1000 sequence reads mapping to a locus, one might expect about 50 reads (about 5%) to include errors. Certain methodologies, such as those described in WO 2014/149134 (Talasaz and Eltoukhy) can significantly reduce the error rate. Errors create noise that can obscure signals from cancer present at low levels in a sample. Thus, if a sample has a tumor burden at a level around the sequencing system error rate, e.g., around 0.1%-5%, it may be difficult to distinguish a signal corresponding to a genetic variant due to cancer from one due to noise.

Diagnosis of cancer can be done by analyzing the genetic variants, even in the presence of noise. The analysis can be based on the frequency of sequence variants or level of CNV and a diagnosis confidence indication or level for detecting genetic variants in the noise range can be established. Next, the process increases the diagnosis confidence. This can be done using a plurality of measurements to increase confidence of diagnosis, or alternatively using measurements at a plurality of time points to determine whether cancer is advancing, in remission or stabilized. The diagnostic confidence can be used to identify disease states. For example, cell free polynucleotides taken from a subject can include polynucleotides derived from normal cells, as well as polynucleotides derived from diseased cells, such as cancer cells. Polynucleotides from cancer cells may bear genetic variants, such as somatic cell mutations and copy number variants. When cell free polynucleotides from a sample from a subject are sequenced, these cancer polynucleotides are detected as sequence variants or as copy number variants. The relative amount of tumor polynucleotides in a sample of cell free polynucleotides is referred to as the "tumor burden."

Measurements of a parameter, whether or not they are in the noise range, may be provided with a confidence interval. Tested over time, one can determine whether a cancer is advancing, stabilized or in remission by comparing confidence intervals over time. Where the confidence intervals do not overlap, this indicates the direction of disease.

Next, the process generates genetic Report/Diagnosis. The process receives germline SNP and somatic cancer mutations and mark somatic cancer mutations and generates a report to annotate somatic mutations similar to human tumor board analysis and provide treatment options to be reviewed and approved by the lab director.

Turning now to the process for generating tumor board recommendations, in some embodiments, the system uses data from cBio portal SNVs for the 68 genes in GH2.7, where GH2.7 is Guardant Health's panel and related testing processes released February 2015 (Guardant360 test) panel. The cBioPortal for Cancer Genomics provides a Web resource for exploring, visualizing, and analyzing multidimensional cancer genomics data. The portal reduces molecular profiling data from cancer tissues and cell lines into readily understandable genetic, epigenetic, gene expression, and proteomic events. The query interface combined with customized data storage enables researchers to interactively explore genetic alterations across samples, genes, and pathways and, when available in the underlying data, to link these to clinical outcomes. The portal provides graphical summaries of gene-level data from multiple platforms, network visualization and analysis, survival analysis, patient-centric queries, and software programmatic access. The system provides variant-level calls as well as sample-level calls in determining whether the director 3 should review the test in depth.

Numerous cancers may be detected using the methods and systems described herein. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as mutations. This phenomenon may be used to detect the presence or absence of cancers individuals using the methods and systems described herein.

In some embodiments, the methods of the present disclosure can be used to diagnose a disease or condition such as cancer or an inflammatory condition. The term "diagnosis" as used herein refers to methods by which the skilled worker can estimate and/or determine whether or not a patient is suffering from a given disease or condition. In some embodiments, the methods of the present disclosure can be used in the prognosis if a disease of a disease or condition such as cancer or an inflammatory condition. The term "prognosis" as used herein refers to the likelihood of a disease or condition progression, including recurrence of a disease or condition. In some embodiments, the methods of the present disclosure can be used to assess the risk of developing a disease or condition such as cancer or an inflammatory condition. In some embodiments, the methods of the present disclosure can be used to assess the efficacy of treatment of a disease or condition such as cancer or an inflammatory condition. For example, the methods of the present disclosure can be used before and after treating a patient with the disease or condition (e.g., before and after administering a drug such as a chemotherapeutic agent). In some embodiments, the methods of the present disclosure can be used to monitor the progression or regression of a disease or condition such as cancer or an inflammatory condition. For example, the methods of the present disclosure can be performed at different time points to monitor the progression or regression. In some embodiments, the methods of the present disclosure can be used to identify a compound for ameliorating or treating a disease or condition such as cancer or an inflammatory condition. For example, the methods of the present disclosure can be used before and after administering the compound to determine whether the compound ameliorates or treats the disease.

As used herein, "treating" a disease or condition refers to taking steps to obtain beneficial or desired results, including clinical results. Beneficial or desired clinical results include, but are not limited to, alleviation or amelioration of one or more symptoms associated with diseases or conditions. As used herein, "administering" or "administration of" a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorbtion, e.g., through a skin duct). A compound or agent can also appropriately be introduced by rechargeable or biodegradable polymeric devices or other devices, e.g., patches and pumps, or formulations, which provide for the extended, slow, or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. In some embodiments, a compound or an agent is administered orally, e.g., to a subject by ingestion, or intravenously, e.g., to a subject by injection. In some embodiments, the orally administered compound or agent is in an extended release or slow release formulation, or administered using a device for such slow or extended release.

In some embodiments, blood from subjects at risk for cancer may be drawn and prepared as described herein to generate a population of cell free polynucleotides. In one example, this might be cell-free DNA. The systems and methods of the disclosure may be employed to detect mutations or copy number variations that may exist in certain cancers present. The method may help detect the presence of cancerous cells in the body, despite the absence of symptoms or other hallmarks of disease.

As used herein, the term "cancer" includes, but is not limited to, various types of malignant neoplasms, most of which can invade surrounding tissues, and may metastasize to different sites (see, for example, PDR Medical Dictionary, 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Such abnormal tissue shows partial or complete lack of structural organization and functional coordination with the normal tissue which may be either benign (such as a benign tumor) or malignant (such as a malignant tumor). Examples of general categories of cancer include, but are not limited to, carcinomas (malignant tumors derived from epithelial cells such as, for example, common forms of breast, prostate, lung and colon cancer), sarcomas (malignant tumors derived from connective tissue or mesenchymal cells), lymphomas (malignancies derived from hematopoietic cells), leukemias (malignancies derived from hematopoietic cells), and germ cell tumors (tumors derived from totipotent cells, in adults most often found in the testicle or ovary; in fetuses, babies and young children, most often found on the body midline, particularly at the tip of the tailbone), blastic tumors (a typically malignant tumor which resembles an immature or embryonic tissue) and the like. Examples of the types of neoplasms intended to be encompassed by the present disclosure include but are not limited to those neoplasms associated with cancers of neural tissue, blood forming tissue, breast, skin, bone, prostate, ovaries, uterus, cervix, liver, lung, brain, larynx, gallbladder, pancreas, rectum, parathyroid, thyroid, adrenal gland, immune system, head and neck, colon, stomach, bronchi, and/or kidneys. In particular embodiments, types and number of cancers that may be detected include, but are not limited to, blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

In some embodiments, the system and methods may be used to detect any number of genetic aberrations that may cause or result from cancers. These may include but are not limited to mutations, mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Additionally, the systems and methods described herein may also be used to help characterize certain cancers. Genetic data produced from the system and methods of this disclosure can allow practitioners to help better characterize a specific form of cancer. Often times, cancers are heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer.

In some embodiments, the systems and methods provided herein are used to monitor already known cancers, or other diseases in a particular subject. This may allow a subject or a practitioner to adapt treatment options in accord with the progress of the disease. In this example, the systems and methods described herein may be used to construct genetic profiles of a particular subject of the course of the disease. In some instances, cancers can progress, becoming more aggressive and genetically unstable. In other examples, cancers may remain benign, inactive or dormant. The system and methods of this disclosure may be useful in determining disease progression.

Further, the systems and methods described herein may be useful in determining the efficacy of a particular treatment option. In some embodiments, successful treatment options may actually increase the amount of copy number variation or mutations detected in subject's blood if the treatment is successful as more cancers may die and shed DNA. In other embodiments, this may not occur. In some embodiments, certain treatment options are correlated with genetic profiles of cancers over time. This correlation may be useful in selecting a therapy. Additionally, if a cancer is observed to be in remission after treatment, the systems and methods described herein may be useful in monitoring residual disease or recurrence of disease.

The methods and systems described herein are not limited to detection of mutations and copy number variations associated with only cancers. Various other diseases and infections may result in other types of conditions that may be suitable for early detection and monitoring. For example, in certain cases, genetic disorders or infectious diseases may cause a certain genetic mosaicism within a subject. This genetic mosaicism may cause copy number variation and mutations that could be observed. In some embodiments, the system and methods of the disclosure may also be used to monitor the genomes of immune cells within the body.

Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing.

In some embodiments, the methods of the present disclosure are applicable to autoimmune or immune-related diseases or conditions. As used herein, "autoimmune or immune-related disease or condition" can refer to any disease, disorder, or condition affecting or associated with the immune system. Examples of autoimmune or immune-related diseases or conditions include, but are not limited to, inflammation, antiphospholipid syndrome, systemic lupus erythematosus, rheumatoid arthritis, autoimmune vasculitis, celiac disease, autoimmune thyroiditis, post-transfusion immunization, maternal-fetal incompatibility, transfusion reactions, immunological deficiency such IgA deficiency, common variable immunodeficiency, drug-induced lupus, diabetes mellitus, Type I diabetes, Type II diabetes, juvenile onset diabetes, juvenile rheumatoid arthritis, psoriatic arthritis, multiple sclerosis, immunodeficiency, allergies, asthma, psoriasis, atopic dermatitis, allergic contact dermatitis, chronic skin diseases, amyotrophic lateral sclerosis, chemotherapy-induced injury, graft-vs-host diseases, bone marrow transplant rejection, Ankylosing spondylitis, atopic eczema, Pemphigus, Behcet's disease, chronic fatigue syndrome fibromyalgia, chemotherapy-induced injury, myasthenia gravis, glomerulonephritis, allergic retinitis, systemic sclerosis, subacute cutaneous lupus erythematosus, cutaneous lupus erythematosus including chilblain lupus erythematosus, Sjogren's syndrome, autoimmune nephritis, autoimmune vasculitis, autoimmune hepatitis, autoimmune carditis, autoimmune encephalitis, autoimmune mediated hematological diseases, lc-SSc (limited cutaneous form of scleroderma), dc-SSc (diffused cutaneous form of scleroderma), autoimmune thyroiditis (AT), Grave's disease (GD), myasthenia gravis, multiple sclerosis (MS), ankylosing spondylitis, transplant rejection, immune aging, rheumatic/autoimmune diseases, mixed connective tissue disease, spondyloarthropathy, psoriasis, psoriatic arthritis, myositis, scleroderma, dermatomyositis, autoimmune vasculitis, mixed connective tissue disease, idiopathic thrombocytopenic purpura, Crohn's disease, human adjuvant disease, osteoarthritis, juvenile chronic arthritis, a spondyloarthropathy, an idiopathic inflammatory myopathy, systemic vasculitis, sarcoidosis, autoimmune hemolytic anemia, autoimmune thrombocytopenia, thyroiditis, immune-mediated renal disease, a demyelinating disease of the central or peripheral nervous system, idiopathic demyelinating polyneuropathy, Guillain-Barre syndrome, a chronic inflammatory demyelinating polyneuropathy, a hepatobiliary disease, infectious or autoimmune chronic active hepatitis, primary biliary cirrhosis, granulomatous hepatitis, sclerosing cholangitis, inflammatory bowel disease, gluten-sensitive enteropathy, Whipple's disease, an autoimmune or immune-mediated skin disease, a bullous skin disease, erythema multiforme, allergic rhinitis, atopic dermatitis, food hypersensitivity, urticaria, an immunologic disease of the lung, eosinophilic pneumonias, idiopathic pulmonary fibrosis, hypersensitivity pneumonitis, a transplantation associated disease, graft rejection or graft-versus-host-disease, psoriatic arthritis, psoriasis, dermatitis, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, antiphospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism, autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Sheehan's syndrome, autoimmune hepatitis, lymphoid interstitial pneumonitis (HIV), bronchiolitis obliterans (non-transplant) vs NSIP, Guillain-Barre' Syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, and amyotrophic lateral sclerosis (ALS). In certain embodiments, the methods of the present disclosure are applicable to inflammatory conditions including, but not limited to, asthma, multiple sclerosis (e.g., relapsing remitting multiple sclerosis and secondary progressive multiple sclerosis), arthritis (e.g., rheumatoid arthritis, osteoarthritis, and psoriatic arthritis), lupus erythematosus, and psoriasis.

In some embodiments, the systems and methods of this disclosure can be used to monitor systemic infections themselves, as may be caused by a pathogen such as a bacteria or virus. Copy number variation or even mutation detection may be used to determine how a population of pathogens are changing during the course of infection. This may be particularly important during chronic infections, such as HIV/AIDS or Hepatitis infections, whereby viruses may change life cycle state and/or mutate into more virulent forms during the course of infection.

In some embodiments, the system and methods of this disclosure can be used for monitoring transplant subjects. Generally, transplanted tissue undergoes a certain degree of rejection by the body upon transplantation. The methods of this disclosure may be used to determine or profile rejection activities of the host body, as immune cells attempt to destroy transplanted tissue. This may be useful in monitoring the status of transplanted tissue as well as altering the course of treatment or prevention of rejection.

Further, in some embodiments, the methods of the disclosure can be used to characterize the heterogeneity of an abnormal condition in a subject, the method comprising generating a genetic profile of extracellular polynucleotides in the subject, wherein the genetic profile comprises a plurality of data resulting from copy number variation and mutation analyses. In some cases, including but not limited to cancer, a disease may be heterogeneous. Disease cells may not be identical. In the example of cancer, some tumors are known to comprise different types of tumor cells, some cells in different stages of the cancer. In some embodiments, heterogeneity comprises multiple foci of disease. Again, in the example of cancer, there may be multiple tumor foci, perhaps where one or more foci are the result of metastases that have spread from a primary site.

The methods of this disclosure can be used to generate a profile, fingerprint, or set of data that is a summation of genetic information derived from different cells in a heterogeneous disease. This set of data can comprise copy number variation and mutation analyses alone or in combination.

Additionally, the systems and methods of the disclosure can be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules. In some embodiments, the systems and methods are useful to diagnose, prognose, monitor or observe a prenatal or pregnancy-related disease or condition. As used herein, the term "prenatal or pregnancy-related disease or condition" refers to any disease, disorder, or condition affecting a pregnant woman, embryo, or fetus. Prenatal or pregnancy-related conditions can also refer to any disease, disorder, or condition that is associated with or arises, either directly or indirectly, as a result of pregnancy. These diseases or conditions can include any and all birth defects, congenital conditions, or hereditary diseases or conditions. Examples of prenatal or pregnancy-related diseases include, but are not limited to, Rhesus disease, hemolytic disease of the newborn, beta-thalassemia, sex determination, determination of pregnancy, a hereditary Mendelian genetic disorder, chromosomal aberrations, a fetal chromosomal aneuploidy, fetal chromosomal trisomy, fetal chromosomal monosomy, trisomy 8, trisomy 13 (Patau Syndrom), trisomy 16, trisomy 18 (Edwards syndrome), trisomy 21 (Down syndrome), X-chromosome linked disorders, trisomy X (XXX syndrome), monosomy X (Turner syndrome), XXY syndrome, XYY syndrome, XYY syndrome, XXXY syndrome, XXYY syndrome, XYYY syndrome, XXXXX syndrome, XXXXY syndrome, XXXYY syndrome, XXYYY syndrome, Fragile X Syndrome, fetal growth restriction, cystic fibrosis, a hemoglobinopathy, fetal death, fetal alcohol syndrome, sickle cell anemia, hemophilia, Klinefelter syndrome, dup (17)(p11.2p1.2) syndrome, endometriosis, Pelizaeus-Merzbacher disease, dup(22)(q11.2q11.2) syndrome, cat eye syndrome, cri-du-chat syndrome, Wolf-Hirschhorn syndrome, Williams-Beuren syndrome, Charcot-Marie-Tooth disease, neuropathy with liability to pressure palsies, Smith-Magenis syndrome, neurofibromatosis, Alagille syndrome, Velocardiofacial syndrome, DiGeorge syndrome, steroid sulfatase deficiency, Prader-Willi syndrome, Kallmann syndrome, microphthalmia with linear skin defects, adrenal hypoplasia, glycerol kinase deficiency, Pelizaeus-Merzbacher disease, testis-determining factor on Y, azospermia (factor a), azospermia (factor b), azospermia (factor c), 1p36 deletion, phenylketonuria, Tay-Sachs disease, adrenal hyperplasia, Fanconi anemia, spinal muscular atrophy, Duchenne's muscular dystrophy, Huntington's disease, myotonic dystrophy, Robertsonian translocation, Angelman syndrome, tuberous sclerosis, ataxia telangieltasia, open spina bifida, neural tube defects, ventral wall defects, small-for-gestational-age, congenital cytomegalovirus, achondroplasia, Marfan's syndrome, congenital hypothyroidism, congenital toxoplasmosis, biotinidase deficiency, galactosemia, maple syrup urine disease, homocystinuria, medium-chain acyl Co-A dehydrogenase deficiency, structural birth defects, heart defects, abnormal limbs, club foot, anencephaly, arhinencephaly/ holoprosencephaly, hydrocephaly, anophthalmos/micropthalmos, anotia/microtia, transposition of great vessels, tetralogy of Fallot, hypoplastic left heart syndrome, coarctation of aorta, cleft palate without cleft lip, cleft lip with or without cleft palate, oesophageal atresia/stenosis with or without fistula, small intestine atresia/stenosis, anorectal atresia/stenosis, hypospadias, indeterminate sex, renal agenesis, cystic kidney, preaxial polydactyly, limb reduction defects, diaphragmatic hernia, blindness, cataracts, visual problems, hearing loss, deafness, X-linked adrenoleukodystrophy, Rett syndrome, lysosomal disorders, cerebral palsy, autism, aglossia, albinism, ocular albinism, oculocutaneous albinism, gestational diabetes, Arnold-Chiari malformation, CHARGE syndrome, congenital diaphragmatic hernia, brachydactlia, aniridia, cleft foot and hand, heterochromia, Dwarnian ear, Ehlers Danlos syndrome, epidermolysis bullosa, Gorham's disease, Hashimoto's syndrome, hydrops fetalis, hypotonia, Klippel-Feil syndrome, muscular dystrophy, osteogenesis imperfecta, progeria, Smith Lemli Opitz symdrom, chromatelopsia, X-linked lymphoproliferative disease, omphalocele, gastroschisis, pre-eclampsia, eclampsia, pre-term labor, premature birth, miscarriage, delayed intrauterine growth, ectopic pregnancy, hyperemesis gravidarum, morning sickness, or likelihood for successful induction of labor.

Further, in some embodiments, the reports are submitted and accessed electronically via the internet. In certain embodiments, analysis of sequence data occurs at a site other than the location of the subject. The report is generated and transmitted to the subject's location. Via an internet enabled computer, the subject accesses the reports reflecting his tumor burden.

The annotated information can be used by a health care provider to select other drug treatment options and/or provide information about drug treatment options to an insurance company. The method can include annotating the drug treatment options for a condition in, for example, the NCCN Clinical Practice Guidelines in Oncology or the American Society of Clinical Oncology (ASCO) clinical practice guidelines.

The drug treatment options that are stratified in a report can be annotated in the report by listing additional drug treatment options. An additional drug treatment can be an FDA-approved drug for an off-label use. A provision in the 1993 Omnibus Budget Reconciliation Act (OBRA) requires Medicare to cover off-label uses of anticancer drugs that are included in standard medical compendia. The drugs used for annotating lists can be found in CMS approved compendia, including the National Comprehensive Cancer Network (NCCN) Drugs and Biologics Compendiumm", Thomson Micromedex DrugDex®, Elsevier Gold Standard's Clinical Pharmacology compendium, and American Hospital Formulary Service—Drug Information Compendium®.

The drug treatment options can be annotated by listing an experimental drug that may be useful in treating a cancer with one or more molecular markers of a particular status. The experimental drug can be a drug for which in vitro data, in vivo data, animal model data, pre-clinical trial data, or clinical-trial data are available. The data can be published in peer-reviewed medical literature found in journals listed in the CMS Medicare Benefit Policy Manual, including, for example, American Journal of Medicine, Annals of Internal Medicine, Annals of Oncology, Annals of Surgical Oncology, Biology of Blood and Marrow Transplantation, Blood, Bone Marrow Transplantation, British Journal of Cancer, British Journal of Hematology, British Medical Journal, Cancer, Clinical Cancer Research, Drugs, European Journal of Cancer (formerly the European Journal of Cancer and Clinical Oncology), Gynecologic Oncology, International Journal of Radiation, Oncology, Biology, and Physics, The Journal of the American Medical Association, Journal of Clinical Oncology, Journal of the National Cancer Institute, Journal of the National Comprehensive Cancer Network (NCCN), Journal of Urology, Lancet, Lancet Oncology, Leukemia, The New England Journal of Medicine, and Radiation Oncology.

The drug treatment options can be annotated by providing a link on an electronic based report connecting a listed drug to scientific information regarding the drug. For example, a link can be provided to information regarding a clinical trial for a drug (clinicaltrials.gov). If the report is provided via a computer or computer website, the link can be a footnote, a hyperlink to a website, a pop-up box, or a fly-over box with information, etc. The report and the annotated information can be provided on a printed form, and the annotations can be, for example, a footnote to a reference.

The information for annotating one or more drug treatment options in a report can be provided by a commercial entity that stores scientific information. A health care provider can treat a subject, such as a cancer patient, with an experimental drug listed in the annotated information, and the health care provider can access the annotated drug treatment option, retrieve the scientific information (e.g., print a medical journal article) and submit it (e.g., a printed journal article) to an insurance company along with a request for reimbursement for providing the drug treatment. Physicians can use any of a variety of Diagnosis-related group (DRG) codes to enable reimbursement.

A drug treatment option in a report can also be annotated with information regarding other molecular components in a pathway that a drug affects (e.g., information on a drug that targets a kinase downstream of a cell-surface receptor that is a drug target). The drug treatment option can be annotated with information on drugs that target one or more other molecular pathway components. The identification and/or annotation of information related to pathways can be outsourced or subcontracted to another company.

The annotated information can be, for example, a drug name (e.g., an FDA approved drug for off-label use; a drug found in a CMS approved compendium, and/or a drug described in a scientific (medical) journal article), scientific information concerning one or more drug treatment options, one or more links to scientific information regarding one or more drugs, clinical trial information regarding one or more drugs (e.g., information from clinicaltrials.gov/), one or more links to citations for scientific information regarding drugs, etc.

The annotated information can be inserted into any location in a report. Annotated information can be inserted in multiple locations on a report. Annotated information can be inserted in a report near a section on stratified drug treatment options. Annotated information can be inserted into a report on a separate page from stratified drug treatment options. A report that does not contain stratified drug treatment options can be annotated with information.

The system can also include reports on the effects of drugs on sample (e.g. tumor cells) isolated from a subject (e.g. cancer patient). An in vitro culture using a tumor from a cancer patient can be established using various techniques. The system can also include high-throughput screening of FDA approved off-label drugs or experimental drugs using said in vitro culture and/or xenograft model. The system can also include monitoring tumor antigen for recurrence detection.

The system can provide internet enabled access of reports of a subject with cancer. The system can use a handheld DNA sequencer or a desktop DNA sequencer. The DNA sequencer is a scientific instrument used to automate the DNA sequencing process. Given a sample of DNA, a DNA sequencer is used to determine the order of the four bases: adenine, guanine, cytosine, and thymine. The order of the DNA bases is reported as a text string, called a read. Some DNA sequencers can be also considered optical instruments as they analyze light signals originating from fluorochromes attached to nucleotides.

The DNA sequencer can apply Gilbert's sequencing method based on chemical modification of DNA followed by cleavage at specific bases, or it can apply Sanger's technique which is based on dideoxynucleotide chain termination. The Sanger method became popular due to its increased efficiency and low radioactivity. The DNA sequencer can use techniques that do not require DNA amplification (polymerase chain reaction—PCR), which speeds up the sample preparation before sequencing and reduces errors. In addition, sequencing data is collected from the reactions caused by the addition of nucleotides in the complementary strand in real time. For example, the DNA sequencers can utilize a method called single-molecule real-time (SMRT), where sequencing data is produced by light (captured by a camera) emitted when a nucleotide is added to the complementary strand by enzymes containing fluorescent dyes. Alternatively, the DNA sequencers can use electronic systems based on nanopore sensing technologies.

The data is sent by the DNA sequencers over a direct connection or over the internet to a computer for processing. The data processing aspects of the system can be implemented in digital electronic circuitry, or in computer hardware, firmware, software, or in combinations of them. Data processing apparatus of the present disclosure can be implemented in a computer program product tangibly embodied in a machine-readable storage device for execution by a programmable processor; and data processing method steps of the present disclosure can be performed by a programmable processor executing a program of instructions to perform functions of the present disclosure by operating on input data and generating output. The data processing aspects of the present disclosure can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object-oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the present disclosure can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

Test Samples

Methods disclosed herein can comprise isolating one or more polynucleotides.

A polynucleotide can comprise any type of nucleic acid, such as DNA and/or RNA. For example, if a polynucleotide is DNA, it can be genomic DNA, complementary DNA (cDNA), or any other deoxyribonucleic acid. A polynucleotide can also be a cell-free nucleic acid such as cell-free DNA (cfDNA). For example, the polynucleotide can be circulating cfDNA. Circulating cfDNA may comprise DNA shed from bodily cells via apoptosis or necrosis. cfDNA shed via apoptosis or necrosis may originate from normal bodily cells. Where there is abnormal tissue growth, such as for cancer, tumor DNA may be shed. The circulating cfDNA can comprise circulating tumor DNA (ctDNA). As described herein, the methods of the present disclosure allow the skilled worker to determine whether the origin of a genetic locus (e.g., a variant at a genetic locus) is germline or somatic from cfDNA, without the need for separate sequence information from genomic DNA.

A polynucleotide can be double-stranded or single-stranded. Alternatively, a polynucleotide can comprise a combination of a double-stranded portion and a single-stranded portion.

A sample can be any biological sample isolated from a subject. For example, a sample can comprise, without limitation, bodily fluid, whole blood, platelets, serum, plasma, stool, red blood cells, white blood cells or leukocytes, endothelial cells, tissue biopsies, synovial fluid, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, fluid from nasal brushings, fluid from a pap smear, or any other bodily fluids. A bodily fluid can include saliva, blood, or serum. For example, a polynucleotide can be cell-free DNA isolated from a bodily fluid, e.g., blood or serum. A sample can also be a tumor sample, which can be obtained from a subject by various approaches, including, but not limited to, venipuncture, excretion, ejaculation, massage, biopsy, needle aspirate, lavage, scraping, surgical incision, or intervention or other approaches. A sample can be a cell-free sample (e.g., not comprising any cells).

A sample can comprise a volume of plasma containing cell free DNA molecules. A sample may comprise a volume of plasma sufficient to achieve a given read depth. A volume of sampled plasma may be at least 0.5 milliliters (mL), 1 mL, 5 mL 10 mL, 20 mL, 30 mL, or 40 mL. A volume of sampled plasma at most 0.5 mL, 1 mL, 5 mL 10 mL, 20 mL, 30 mL, or 40 mL. A volume of sampled plasma may be 5 to 20 mL. A volume of sampled plasma may be 10 ml to 20 mL.

A sample can comprise various amount of nucleic acid that contains genome equivalents. For example, a sample of about 30 ng DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources. For example, a sample can comprise germline DNA or somatic DNA. A sample can comprise nucleic acids carrying mutations. For example, a sample can comprise DNA carrying germline mutations and/or somatic mutations. A sample can also comprise DNA carrying cancer-associated mutations (e.g., cancer-associated somatic mutations). In some embodiments, a sample comprises one or more of: a single base substitution, a copy number variation, an indel, a gene fusion, a transversion, a translocation, an inversion, a deletion, aneuploidy, partial aneuploidy, polyploidy, chromosomal instability, chromosomal structure alterations, chromosome fusions, a gene truncation, a gene amplification, a gene duplication, a chromosomal lesion, a DNA lesion, abnormal changes in nucleic acid chemical modifications, abnormal changes in epigenetic patterns, abnormal changes in distributions of nucleic acid (e.g., cfDNA) fragments across genomic regions, abnormal changes in distributions of nucleic acid (e.g., cfDNA) fragment lengths, and abnormal changes in nucleic acid methylation.

Methods herein can comprise obtaining certain amount of nucleic acid molecules, e.g., cell-free nucleic acid molecules from a sample. For example, the method can comprise obtaining up to about 600 ng, up to about 500 ng, up to about 400 ng, up to about 300 ng, up to about 200 ng, up to about 100 ng, up to about 50 ng, or up to about 20 ng of cell-free nucleic acid molecules from a sample. The method can comprise obtaining at least 1 femtogram (fg), at least 10 fg, at least 100 fg, at least 1 picogram (pg), at least 10 pg, at least 100 pg, at least 1 ng, at least 10 ng, at least 100 ng, at least 150 ng, or at least 200 ng of cell-free nucleic acid molecules. The method can comprise obtaining at most 1 femtogram (fg), at most 10 fg, at most 100 fg, at most 1 picogram (pg), at most 10 pg, at most 100 pg, at most 1 ng, at most 10 ng, at most 100 ng, at most 150 ng, or at most 200 ng of cell-free nucleic acid molecules. The method can comprise obtaining 1 femtogram (fg) to 200 ng, 1 picogram (pg) to 200 ng, 1 ng to 100 ng, 10 ng to 150 ng, 10 ng to 200 ng, 10 ng to 300 ng, 10 ng to 400 ng, 10 ng to 500 ng, 10 ng to 600 ng, 10 ng to 700 ng, 10 ng to 800 ng, 10 ng to 900 ng, or 10 ng to 1000 ng of cell-free nucleic acid molecules. An amount of cell-free nucleic acid molecules may be equivalent to a number of haploid genome copies. Because a haploid genome copy has a mass of about 3.3 picograms (pg), each nanogram (ng) of cell-free nucleic molecules may be equivalent to about 300 haploid genome copies. For example, 5 ng of cell-free nucleic acid molecules may be equivalent to 1,500 genome copies.

A cell-free nucleic acid can be any extracellular nucleic acid that is not attached to a cell. A cell-free nucleic acid can be a nucleic acid circulating in blood. Alternatively, a cell-free nucleic acid can be a nucleic acid in other bodily fluid disclosed herein, e.g., urine. A cell-free nucleic acid can be a deoxyribonucleic acid ("DNA"), e.g., genomic DNA, mitochondrial DNA, or a fragment thereof. A cell-free nucleic acid can be a ribonucleic acid ("RNA"), e.g., mRNA, short-interfering RNA (siRNA), microRNA (miRNA), circulating RNA (cRNA), transfer RNA (tRNA), ribosomal RNA (rRNA), small nucleolar RNA (snoRNA), Piwi-interacting RNA (piRNA), long non-coding RNA (long ncRNA), or a fragment thereof. In some cases, a cell-free nucleic acid is a DNA/RNA hybrid. A cell-free nucleic acid can be double-stranded, single-stranded, or a hybrid thereof. A cell-free nucleic acid can be released into bodily fluid through secretion or cell death processes, e.g., cellular necrosis and apoptosis.

A cell-free nucleic acid can comprise one or more epigenetically modifications. For example, a cell-free nucleic acid can be acetylated, methylated, ubiquitylated, phosphorylated, sumoylated, ribosylated, and/or citrullinated. For example, a cell-free nucleic acid can be methylated cell-free DNA.

Cell-free DNA typically has a size distribution of about 110 to about 230 nucleotides, with a mode of about 168 nucleotides. A second, minor peak detected in assays quantifying cell-free nucleic acid molecule length has a range between 240 to 440 nucleotides. Additional higher order nucleotide peaks are present as well at longer lengths.

In some embodiments of the present disclosure, cell-free nucleic acids can be at most 1,000 nucleotides (nt) in length, at most 500 nucleotides in length, at most 400 nucleotides in length, at most 300 nucleotides in length, at most 250 nucleotides in length, at most 225 nucleotides in length, at most 200 nucleotides in length, at most 190 nucleotides in length, at most 180 nucleotides in length, at most 170 nucleotides in length, at most 160 nucleotides in length, at most 150 nucleotides in length, at most 140 nucleotides in length, at most 130 nucleotides in length, at most 120 nucleotides in length, at most 110 nucleotides in length, or at most 100 nucleotides in length.

In some embodiments of the present disclosure, cell-free nucleic acids can be at least 1,000 nucleotides in length, at least 500 nucleotides in length, at least 400 nucleotides in length, at least 300 nucleotides in length, at least 250 nucleotides in length, at least 225 nucleotides in length, at least 200 nucleotides in length, at least 190 nucleotides in length, at least 180 nucleotides in length, at least 170 nucleotides in length, at least 160 nucleotides in length, at least 150 nucleotides in length, at least 140 nucleotides in length, at least 130 nucleotides in length, at least 120 nucleotides in length, at least 110 nucleotides in length, or at least 100 nucleotides in length. Cell-free nucleic acids can be from 140 to 180 nucleotides in length.

In some embodiments of the present disclosure, cell free nucleic acids in a subject may derive from a tumor. For example cell-free DNA isolated from a subject can comprise circulating tumor DNA, (ctDNA). Next generation sequencing allows detection and measurement of rare mutations. Detection of mutations relative to germline sequence in a fraction of cell-free DNA can indicate the presence of ctDNA, thus indicating the presence of a tumor. Sequencing cell free DNA may allow detection a genetic variant that is known to indicate the presence of cancer. For example sequencing cell free DNA may allow detection of mutations in cancer related genes.

Isolation and Extraction

Cell-free polynucleotides may be fetal in origin (via fluid taken from a pregnant subject), or may be derived from tissue of the subject itself. Cell-free polynucleotides may derive from healthy tissue, from diseased tissue such as tumor tissue, or from a transplant organ.

In some embodiments, cell-free polynucleotides are derived from a blood sample or a fraction thereof. For example, a blood sample (e.g., about 10 to about 30 mls) can be taken from a subject, centrifuged to remove cells, and the resulting plasma used for cfDNA extraction.

Isolation and extraction of polynucleotides may be performed through collection of bodily fluids using a variety of techniques. In some cases, collection may comprise aspiration of a bodily fluid from a subject using a syringe. In other cases collection may comprise pipetting or direct collection of fluid into a collecting vessel.

After collection of bodily fluid, polynucleotides may be isolated and extracted using a variety of techniques utilized in the art. In some cases, cell-free DNA may be isolated, extracted and prepared using commercially available kits such as the Qiagen Qiamp® Circulating Nucleic Acid Kit protocol. In other examples, Qiagen Qubit™ dsDNA HS Assay kit protocol, Agilent™ DNA 1000 kit, or TruSeq™ Sequencing Library Preparation; Low-Throughput (LT) protocol may be used.

Generally, cell free polynucleotides may be extracted and isolated by from bodily fluids through a partitioning step in which cell-free DNAs, as found in solution, are separated from cells and other non-soluble components of the bodily fluid. Partitioning may include, but is not limited to, techniques such as centrifugation or filtration. In other cases, cells may not be partitioned from cell-free DNA first, but rather lysed. For instance, the genomic DNA of intact cells may be partitioned through selective precipitation. Sample partitioning may be combined with tagging nucleic acids with identifiers (such as identifiers comprising bar codes), or may be performed in a method without the use of an identifier. A sample can be divided into partitions such that each partition can be barcoded independently (e.g., with one unique bar code per partition), and sequencing data from the partitions can later be recombined. A sample can be divided into partitions, and the nucleic acid molecules non-uniquely tagged with respect to one another within a partition, or between partitions. In some embodiments, a sample can be divided into partitions without the use of identifiers. In one example, a cfDNA sample is divided into 4 or more partitions, wherein each partition is a spatially addressable location. Sample preparation and sequencing is performed on each spatially addressable partition, and bioinformatics can utilize the addressable location to further identify a unique molecule. In one example, nucleic acid molecules can be divided into partitions, for example, containing different types of nucleic acid molecules (e.g., double stranded nucleic acids such as DNA and/or single stranded nucleic acids such as RNA and/or single stranded DNA). Cell-free polynucleotides, including DNA, may remain soluble and may be separated from insoluble genomic DNA and extracted. Generally, after addition of buffers and other wash steps specific to different kits, DNA may be precipitated using isopropanol precipitation. Further clean up steps may be used such as silica based columns or beads (such as magnetic beads) to remove contaminants or salts. General steps may be optimized for specific applications. Non-specific bulk carrier polynucleotides, for example, may be added throughout the reaction to optimize certain aspects of the procedure such as yield.

In some embodiments, a plasma sample is treated to degrade proteinase K and DNA is precipitated with isopropanol and subsequently captured on a Qiagen column. The DNA then can be eluted (e.g., using 100 microliters (µl) of eluent such as water or Tris-EDTA (TE) elution buffer). In some embodiments, a portion of the DNA can be selected based on size (e.g., DNA of 500 nucleotides or fewer in length), for example, using Solid Phase Reversible Immobilization (SPRI) beads, such as AgenCourt®AMPure® beads. In some embodiments, the DNA can be resuspended in a smaller volume, such as 30 µl of water, and checked for size distribution of the DNA (e.g., to check for a major peak at 166 nucleotides and a minor peak at 330 nucleotides). Approximately 5 ng of DNA may be equivalent to about 1500 haploid genome equivalents ("HGE").

After extraction, samples may yield up to 1 microgram (µg) of DNA, up to 800 ng of DNA, up to 500 ng of DNA, up to 300 ng of DNA, up to 250 ng of DNA, up to 200 ng of DNA, up to 180 ng of DNA, up to 160 ng of DNA, up to 140 ng of DNA, up to 120 ng of DNA, up to 100 ng of DNA, up to 90 ng of DNA, up to 80 ng of DNA, up to 70 ng of DNA, up to 60 ng of DNA, up to 50 ng of DNA, up to 40 ng of DNA, up to 30 ng of DNA, up to 20 ng of DNA, up to 10 ng of DNA, up to 9 ng of DNA, up to 8 ng of DNA, up to 7 ng of DNA, up to 6 ng of DNA, up to 5 ng of DNA, up to 4 ng of DNA, up to 3 ng of DNA, up to 2 ng of DNA, or up to 1 ng of DNA.

After extraction, samples may yield at least 1 ng of DNA, at least 3 ng of DNA, at least 5 ng of DNA, at least 7 ng of DNA, at least 10 ng of DNA, at least 20 ng of DNA, at least 30 ng of DNA, at least 40 ng of DNA, at least 50 ng of DNA, at least 70 ng of DNA, at least 100 ng of DNA, at least 150 ng of DNA, at least 200 ng of DNA, at least 250 ng of DNA, at least 300 ng of DNA, at least 400 ng of DNA, at least 500 ng of DNA, or at least 700 ng of DNA.

One or more of the cell-free nucleic acids can be isolated from a cellular fragment in a sample. In some cases, one or more of the cell-free nucleic acids are isolated from membrane, cellular organelles, nucleosomes, exosomes, or nucleus, mitochondria, rough endoplasmic reticulum, ribosomes, smooth endoplasmic reticulum, chloroplasts, Golgi apparatus, Golgi bodies, glycoproteins, glycolipids, cisternaes, liposomes, peroxisomes, glyoxysomes, centriole, cytoskeleton, lysosomes, cilia, flagellum, contractile vacuole, vesicles, nuclear envelopes, vacuoles, microtubule, nucleoli, plasma membrane, endosomes, chromatins, or a combination thereof. One or more of the cell-free nucleic acids can be isolated from one or more exosomes. In some cases, one or more of the cell-free nucleic acids are isolated from one or more cell surface bound nucleic acids.

Purification of cell free DNA may be accomplished using any methodology, including, but not limited to, the use of commercial kits and protocols provided by companies such as Sigma Aldrich, Life Technologies, Promega, Affymetrix, IBI or the like. Kits and protocols may also be non-commercially available.

After isolation, in some cases, the cell free polynucleotides may be pre-mixed with one or more additional materials, such as one or more reagents (e.g., ligase, protease, polymerase) prior to sequencing.

Cell-free DNA can be sequenced at a read depth sufficient to detect a genetic variant at a frequency in a sample as low as 0.0005%. Cell-free DNA can be sequenced at a read depth sufficient to detect a genetic variant at a frequency in a sample as low as 0.001%. Cell-free DNA can be sequenced at a read depth sufficient to detect a genetic variant at a frequency in a sample as low as 1.0%, 0.75%, 0.5%, 0.25%, 0.1%, 0.075%, 0.05%, 0.025%, 0.01%, or 0.005%. Thus, sequencing cell free DNA allows very sensitive detection of cancer in a subject.

Methods herein can be used to detect cancer in a subject. Cell free DNA can be sequenced in subjects not known to have cancer, or suspected of having cancer to diagnose the presence of absence of a cancer. Sequencing cell free DNA provides a noninvasive method for early detection of cancer or for 'biopsy' of a known cancer. Cell free DNA can be sequenced in subjects diagnosed with cancer to provide information about the cancer. Cell free DNA can be sequenced in subjects before and after treatment for cancer to determine the efficacy of the treatment.

A subject may be suspected of having cancer or may not be suspected of having cancer. A subject may have experienced symptoms consistent with a diagnosis of cancer. A subject may not have experienced any symptoms, or may have exhibited symptoms not consistent with cancer. A subject may have been diagnosed with a cancer based on biological imaging methods. A subject may not have a cancer that is detectable by imaging methods. The imaging methods can be positron emission tomography scan, magnetic resonance imaging, X-ray, computerized axial tomography scan, ultrasound, or a combination thereof.

A subject may exhibit a cancer. Alternatively, a subject may not detectably exhibit a cancer. In some cases, a subject who does not detectably exhibit a cancer can have a cancer, but have no detectable symptoms. Subjects not known to have cancer, or suspected of having cancer, can have cancer that is not detectable using various cancer screening methods. No cancer may be detected using various imaging methods. The imaging methods may include, for example, positron emission tomography scan, magnetic resonance imaging, X-ray, computerized axial tomography scan, endoscopy, ultrasound, or a combination thereof. For a subject not known to have cancer or suspected of having cancer, tests such as tissue biopsy, bone marrow aspiration, pap tests, fecal occult blood tests, protein biomarker detection, e.g., prostate-specific antigen test, alpha-fetoprotein blood test, or CA-125 test, or a combination thereof, may indicate that a subject does not have cancer, e.g., detect no cancer for the subject. In other cases, a subject who does not detectably exhibit a cancer may not have any cancer.

The subject may be at higher risk of having cancer than a general population. The subject may have a family history of cancer. The subject may have known genetic sources of cancer risk. The subject may have been exposed to environmental conditions known to increase or cause cancer risk. The subjects can be patients whose only risk factors for cancer are age and/or gender. The subject may have no known cancer risk factors.

The subject may have been diagnosed with a cancer. The cancer may be early stage or late stage. The cancer may be metastatic or may not be metastatic. Types of cancer that a subject may have been diagnosed with include, but are not limited to: carcinomas, sarcomas, lymphomas, leukemia's, germ cell tumors and blastomas. Types of cancer that a subject may have been diagnosed with include, but are not limited to: Acute lymphoblastic leukemia (ALL), Acute myeloid leukemia, Adrenocortical carcinoma, adult acute Myeloid leukemia, adult carcinoma of unknown primary site, adult malignant Mesothelioma, AIDS-related cancers, AIDS-related lymphoma, Anal cancer, Appendix cancer, Astrocytoma, childhood cerebellar or cerebral, Basal-cell carcinoma, Bile duct cancer, Bladder cancer, Bone tumor, osteosarcoma/malignant fibrous histiocytoma, Brain cancer, Brainstem glioma, Breast cancer, Bronchial adenomas/carcinoids, Burkitt Lymphoma, Carcinoid tumor, Carcinoma of unknown primary, Central nervous system lymphoma, cerebellar astrocytoma, cerebral astrocytoma/malignant glioma, Cervical cancer, childhood acute Myeloid leukemia, childhood cancer of unknown primary site, Childhood cancers, childhood cerebral astrocytoma, childhood Mesothelioma, Chondrosarcoma, Chronic lymphocytic leukemia, Chronic myelogenous leukemia, Chronic myeloproliferative disorders, Colon cancer, Cutaneous T-cell lymphoma, Desmoplastic small round cell tumor, Endometrial cancer, endometrial Uterine cancer, Ependymoma, Epitheliod Hemangioendothelioma (EHE), Esophageal cancer, Ewing family of tumors Sarcoma, Ewing's sarcoma in the Ewing family of tumors, Extracranial germ cell tumor, Extragonadal germ cell tumor, Extrahepatic bile duct cancer, Eye cancer, intraocular melanoma, Gallbladder cancer, Gastric (stomach) cancer, Gastric carcinoid, Gastrointestinal carcinoid tumor, Gastrointestinal stromal tumor (GIST), Gestational trophoblastic tumor, Glioma of the brain stem, Glioma, Hairy cell leukemia, Head and neck cancer, Heart cancer, Hepatocellular (liver) cancer, Hodgkin lymphoma, Hypopharyngeal cancer, Hypothalamic and visual pathway glioma, Islet cell carcinoma (endocrine pancreas), Kaposi sarcoma, Kidney cancer (renal cell cancer), Laryngeal cancer, Leukaemia, acute lymphoblastic (also called acute lymphocytic leukaemia), Leukaemia, acute myeloid (also called acute myelogenous leukemia), Leukaemia, chronic lymphocytic (also called chronic lymphocytic leukemia), Leukaemias, Leukemia, chronic myelogenous (also called chronic myeloid leukemia), Leukemia, hairy cell, Lip and oral cavity cancer, Liposarcoma, Liver cancer (primary), Lung cancer, non-small cell, Lung cancer, small cell, Lymphoma (AIDS-related), Lymphomas, Macroglobulinemia, Waldenström, Male breast cancer, Malignant fibrous histiocytoma of bone/osteosarcoma, medulloblastoma, Melanoma, Merkel cell cancer, Metastatic squamous neck cancer with occult primary, Mouth cancer, Multiple endocrine neoplasia syndrome, childhood, multiple Myeloma (cancer of the bone-marrow), Multiple myeloma/plasma cell neoplasm, Mycosis fungoides, Myelodysplastic syndromes, Myelodysplastic/myeloproliferative diseases, Myelogenous leukemia, chronic, Myxoma, Nasal cavity and paranasal sinus cancer, Nasopharyngeal carcinoma, Neuroblastoma, Non-Hodgkin Lymphomas, Non-small cell lung cancer, Oligodendroglioma, Oral cancer, Oropharyngeal cancer, Osteosarcoma/malignant fibrous histiocytoma of bone, Ovarian cancer, Ovarian epithelial cancer (surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter transitional cell cancer, Retinoblastoma, Rhabdomyosarcoma, Salivary gland cancer, Sézary syndrome, Skin cancer (melanoma), Skin cancer (non-melanoma), Skin carcinoma, Merkel cell, Small cell lung cancer, Small intestine cancer, soft tissue Sarcoma, Squamous cell carcinoma, Squamous neck cancer with occult primary, metastatic, Stomach cancer, Supratentorial primitive neuroectodermal tumor, T-Cell lymphoma, cutaneous, Testicular cancer, Throat cancer, Thymoma and thymic carcinoma, Thymoma, Thyroid cancer, Transitional cell cancer of the renal pelvis and ureter, Ureter and renal pelvis, transitional cell cancer, Urethral cancer, Uterine sarcoma, Vaginal cancer, visual pathway and hypothalamic glioma, Visual pathway and hypothalamic glioma, childhood, Vulvar cancer, Waldenström macroglobulinemia, and Wilms tumor (kidney cancer).

The subject may have previously received treatment for a cancer. The subject may have received surgical treatment, radiation treatment, chemotherapy, targeted cancer therapeutics or a cancer immunotherapy. The subject may have been treated with a cancer vaccine. The subject may have been treated with an experimental cancer treatment. The subject may not have received a cancer treatment. The subject may be in remission from cancer. The subject may have previously received a treatment for cancer and not detectably exhibit any symptoms.

Genetic Analysis

Certain DNA sequencing methods use sequence capture to enrich for sequences of interest. Sequence capture typically involves the use of oligonucleotide probes that hybridize to the sequence of interest. A probe set strategy can involve tiling the probes across a region of interest. Such probes can be, e.g., about 60 to 120 bases long. The set can have a depth of about 2×, 3×, 4×, 5×, 6×, 8×, 9×, 10×, 15×, 20×, 50× or more. The effectiveness of sequence capture depends, in part, on the length of the sequence in the target molecule that is complementary (or nearly complementary) to the sequence of the probe. Enriched nucleic acid molecules can be representative of more than 5,000 bases of the human genome, more than 10,000 bases of the human genome, more than 15,000 bases of the human genome, more than 20,000 bases of the human genome, more than 25,000 bases of the human genome, more than 30,000 bases of the human genome, more than 35,000 bases of the human genome, more than 40,000 bases of the human genome, more than 45,000 bases of the human genome, more than 50,000 bases of the human genome, more than 55,000 bases of the human genome, more than 60,000 bases of the human genome, more than 65,000 bases of the human genome, more than 70,000 bases of the human genome, more than 75,000 bases of the human genome, more than 80,000 bases of the human genome, more than 85,000 bases of the human genome, more than 90,000 bases of the human genome, more than 95,000 bases of the human genome, or more than 100,000 bases of the human genome. Enriched nucleic acid molecules can be representative of no greater than 5,000 bases of the human genome, no greater than 10,000 bases of the human genome, no greater than 15,000 bases of the human genome, no greater than 20,000 bases of the human genome, no greater than 25,000 bases of the human genome, no greater than 30,000 bases of the human genome, no greater than 35,000 bases of the human genome, no greater than 40,000 bases of the human genome, no greater than 45,000 bases of the human genome, no greater than 50,000 bases of the human genome, no greater than 55,000 bases of the human genome, no greater than 60,000 bases of the human genome, no greater than 65,000 bases of the human genome, no greater than 70,000 bases of the human genome, no greater than 75,000 bases of the human genome, no greater than 80,000 bases of the human genome, no greater than 85,000 bases of the human genome, no greater than 90,000 bases of the human genome, no greater than 95,000 bases of the human genome, or no greater than 100,000 bases of the human genome. Enriched nucleic acid molecules can be representative of 5,000-100,000 bases of the human genome, 5,000-50,000 bases of the human genome, 5,000-30,000 bases of the human genome, 10,000-100,000 bases of the human genome, 10,000-50,000 bases of the human genome, or 10,000-30,000 bases of the human genome. Enriched nucleic acid molecules can be representative of various nucleic acid features, including genetic variants such as nucleotide variants (SNVs), copy number variants (CNVs), insertions or deletions (e.g., indels), nucleosome regions associated with cancer, gene fusions, and inversions.

Generally, the methods and systems provided herein are useful for preparation of cell free polynucleotide sequences to a down-stream application sequencing reaction. The sequencing method can be massively parallel sequencing, that is, simultaneously (or in rapid succession) sequencing any of at least 100, 1000, 10,000, 100,000, 1 million, 10 million, 100 million, 1 billion, or 10 billion polynucleotide molecules. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, or Nanopore platforms and any other sequencing methods known in the art.

Individual polynucleotide fragments in a genomic nucleic acid sample (e.g., genomic DNA sample) can be uniquely identified by tagging with non-unique identifiers, e.g., non-uniquely tagging the individual polynucleotide fragments.

Sequencing Panel

To improve the likelihood of detecting tumor indicating mutations, the region of DNA sequenced may comprise a panel of genes or genomic regions. Selection of a limited region for sequencing (e.g., a limited panel) can reduce the total sequencing needed (e.g., a total amount of nucleotides sequenced. A sequencing panel can target a plurality of different genes or regions to detect a single cancer, a set of cancers, or all cancers.

In some aspects, a panel targets a plurality of different genes or genomic regions is selected such that a determined proportion of subjects having a cancer exhibits a genetic variant or tumor marker in one or more different genes or genomic regions in the panel. The panel may be selected to limit a region for sequencing to a fixed number of base pairs. The panel may be selected to sequence a desired amount of DNA. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity and/or a theoretical accuracy for detecting one or more genetic variants in a sample.

Probes for detecting the panel of regions can include those for detecting hotspots regions as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models. The panel can comprise a plurality of subpanels, including subpanels for identifying tissue of origin (e.g., use of published literature to define 50-100 baits representing genes with most diverse transcription profile across tissues (not necessarily promoters)), whole genome scaffold (e.g., for identifying ultra-conservative genomic content and tiling sparsely across chromosomes with handful of probes for copy number base lining purposes), transcription start site (TSS)/CpG islands (e.g., for capturing differential methylated regions (e.g., Differentially Methylated Regions (DMRs)) in for example in promoters of tumor suppressor genes (e.g., SEPT9/VIM in colorectal cancer)). In some embodiments, markers for a tissue of origin are tissue-specific epigenetic markers.

Exemplary listings of genomic locations of interest may be found in Table 1 and Table 2. In some embodiments, genomic regions used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or 97 of the genes of Table 1. In some embodiments, genomic regions used in the methods of the present disclosure comprise at least 5, at least 10, at least 15, at least 20, at least 25, at least 30, at least 35, at least 40, at least 45, at least 50, at least 55, at least 60, at least 65, or 70 of the SNVs of Table 1. In some embodiments, genomic regions used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 1. In some embodiments, genomic regions used in the methods of the present disclosure comprise at least 1, at least 2, at least 3, at least 4, at least 5, or 6 of the fusions of Table 1. In some embodiments, genomic regions used in the methods of the present disclosure comprise at least a portion of at least 1, at least 2, or 3 of the indels of Table 1. In some embodiments, genomic regions used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or 115 of the genes of Table 2. In some embodiments, genomic regions used in the methods of the present disclosure comprise at least 5, at least 10, at least 15, at least 20, at least 25, at least 30, at least 35, at least 40, at least 45, at least 50, at least 55, at least 60, at least 65, at least 70, or 73 of the SNVs of Table 2. In some embodiments, genomic regions used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 2. In some embodiments, genomic regions used in the methods of the present disclosure comprise at least 1, at least 2, at least 3, at least 4, at least 5, or 6 of the fusions of Table 2. In some embodiments, genomic regions used in the methods of the present disclosure comprise at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 2. Each of these genomic locations of interest may be identified as a backbone region or hot-spot region for a given bait set panel. An exemplary listing of hot-spot genomic locations of interest may be found in Table 3. In some embodiments, genomic regions used in the methods of the present disclosure comprise at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 3. Each hot-spot genomic region is listed with several characteristics, including the associated gene, chromosome on which it resides, the start and stop position of the genome representing the gene's locus, the length of the gene's locus in base pairs, the exons covered by the gene, and the critical feature (e.g., type of mutation) that a given genomic region of interest may seek to capture.

TABLE 1

| | Point Mutations (SNVs) | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | CDKN2B | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | |
| RIT1 | ROS1 | SMAD4 | SMO | SRC | STK11 | | | | |
| TERT | TP53 | TSC1 | VHL | | | | | | |

TABLE 2

| | Point Mutations (SNVs) | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | DDR2 | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |

TABLE 2-continued

| | Point Mutations (SNVs) | | | | | Amplifications (CNVs) | Fusions | Indels |
|---|---|---|---|---|---|---|---|---|
| NPM1 | NRAS | NTRK1 | PDGFRA | PIK3CA | PTEN | PIK3CA | RAF1 | skipping) |
| PTPN11 | RAF1 | RB1 | RET | RHEB | RHOA | | | ATM |
| RIT1 | ROS1 | SMAD4 | SMO | MAPK1 | STK11 | | | |
| TERT | TP53 | TSC1 | VHL | MAPK3 | MTOR | | | |
| NTRK3 | | | | | | | | APC |
| | | | | | | | | ARID1A |
| | | | | | | | | BRCA1 |
| | | | | | | | | BRCA2 |
| | | | | | | | | CDH1 |
| | | | | | | | | CDKN2A |
| | | | | | | | | GATA3 |
| | | | | | | | | KIT |
| | | | | | | | | MLH1 |
| | | | | | | | | MTOR |
| | | | | | | | | NF1 |
| | | | | | | | | PDGFRA |
| | | | | | | | | PTEN |
| | | | | | | | | RB1 |
| | | | | | | | | SMAD4 |
| | | | | | | | | STK11 |
| | | | | | | | | TP53 |
| | | | | | | | | TSC1 |
| | | | | | | | | VHL |

TABLE 3

| Gene | Chromosome | Start Position | Stop Position | Length (bp) | Exons Covered | Critical Feature |
|---|---|---|---|---|---|---|
| ALK | chr2 | 29446405 | 29446655 | 250 | intron 19 | Fusion |
| ALK | chr2 | 29446062 | 29446197 | 135 | intron 20 | Fusion |
| ALK | chr2 | 29446198 | 29466404 | 206 | 20 | Fusion |
| ALK | chr2 | 29447353 | 29447473 | 120 | intron 19 | Fusion |
| ALK | chr2 | 29447614 | 29448316 | 702 | intron 19 | Fusion |
| ALK | chr2 | 29448317 | 29448441 | 124 | 19 | Fusion |
| ALK | chr2 | 29449366 | 29449777 | 411 | intron 18 | Fusion |
| ALK | chr2 | 29449778 | 29449950 | 172 | 18 | Fusion |
| BRAF | chr7 | 140453064 | 140453203 | 139 | 15 | BRAF V600 |
| CTNNB1 | chr3 | 41266007 | 41266254 | 247 | 3 | S37 |
| EGFR | chr7 | 55240528 | 55240827 | 299 | 18 and 19 | G719 and deletions |
| EGFR | chr7 | 55241603 | 55241746 | 143 | 20 | Insertions/T790M |
| EGFR | chr7 | 55242404 | 55242523 | 119 | 21 | L858R |
| ERBB2 | chr17 | 37880952 | 37881174 | 222 | 20 | Insertions |
| ESR1 | chr6 | 152419857 | 152420111 | 254 | 10 | V534, P535, L536, Y537, D538 |
| FGFR2 | chr10 | 123279482 | 123279693 | 211 | 6 | S252 |
| GATA3 | chr10 | 8111426 | 8111571 | 145 | 5 | SS/Indels |
| GATA3 | chr10 | 8115692 | 8116002 | 310 | 6 | SS/Indels |
| GNAS | chr20 | 57484395 | 57484488 | 93 | 8 | R844 |
| IDH1 | chr2 | 209113083 | 209113394 | 311 | 4 | R132 |
| IDH2 | chr15 | 90631809 | 90631989 | 180 | 4 | R140, R172 |
| KIT | chr4 | 55524171 | 55524258 | 87 | 1 | |
| KIT | chr4 | 55561667 | 55561957 | 290 | 2 | |
| KIT | chr4 | 55564439 | 55564741 | 302 | 3 | |
| KIT | chr4 | 55565785 | 55565942 | 157 | 4 | |
| KIT | chr4 | 55569879 | 55570068 | 189 | 5 | |
| KIT | chr4 | 55573253 | 55573463 | 210 | 6 | |
| KIT | chr4 | 55575579 | 55575719 | 140 | 7 | |
| KIT | chr4 | 55589739 | 55589874 | 135 | 8 | |
| KIT | chr4 | 55592012 | 55592226 | 214 | 9 | |
| KIT | chr4 | 55593373 | 55593718 | 345 | 10 and 11 | 557, 559, 560, 576 |
| KIT | chr4 | 55593978 | 55594297 | 319 | 12 and 13 | V654 |
| KIT | chr4 | 55595490 | 55595661 | 171 | 14 | T670, S709 |
| KIT | chr4 | 55597483 | 55597595 | 112 | 15 | D716 |
| KIT | chr4 | 55598026 | 55598174 | 148 | 16 | L783 |
| KIT | chr4 | 55599225 | 55599368 | 143 | 17 | C809, R815, D816, L818, D820, S821F, N822, Y823 |
| KIT | chr4 | 55602653 | 55602785 | 132 | 18 | A829P |
| KIT | chr4 | 55602876 | 55602996 | 120 | 19 | |
| KIT | chr4 | 55603330 | 55603456 | 126 | 20 | |
| KIT | chr4 | 55604584 | 55604733 | 149 | 21 | |
| KRAS | chr12 | 25378537 | 25378717 | 180 | 4 | A146 |
| KRAS | chr12 | 25380157 | 25380356 | 199 | 3 | Q61 |

TABLE 3-continued

| Gene | Chromosome | Start Position | Stop Position | Length (bp) | Exons Covered | Critical Feature |
|---|---|---|---|---|---|---|
| KRAS | chr12 | 25398197 | 25398328 | 131 | 2 | G12/G13 |
| MET | chr7 | 116411535 | 116412255 | 720 | 13, 14, intron 13, intron 14 | MET exon 14 SS |
| NRAS | chr1 | 115256410 | 115256609 | 199 | 3 | Q61 |
| NRAS | chr1 | 115258660 | 115258791 | 131 | 2 | G12/G13 |
| PIK3CA | chr3 | 178935987 | 178936132 | 145 | 10 | E545K |
| PIK3CA | chr3 | 178951871 | 178952162 | 291 | 21 | H1047R |
| PTEN | chr10 | 89692759 | 89693018 | 259 | 5 | R130 |
| SMAD4 | chr18 | 48604616 | 48604849 | 233 | 12 | D537 |
| TERT | chr5 | 1294841 | 1295512 | 671 | promoter | chr5: 1295228 |
| TP53 | chr17 | 7573916 | 7574043 | 127 | 11 | Q331, R337, R342 |
| TP53 | chr17 | 7577008 | 7577165 | 157 | 8 | R273 |
| TP53 | chr17 | 7577488 | 7577618 | 130 | 7 | R248 |
| TP53 | chr17 | 7578127 | 7578299 | 172 | 6 | R213/Y220 |
| TP53 | chr17 | 7578360 | 7578564 | 204 | 5 | R175/Deletions |
| TP53 | chr17 | 7579301 | 7579600 | 299 | 4 | |
| | | | | 12574 (total target region) | | |
| | | | | 16330 (total probe coverage) | | |

In some embodiments, the one or more regions in the panel comprise one or more loci from one or a plurality of genes for detecting residual cancer after surgery. This detection can be earlier than is possible for existing methods of cancer detection. In some embodiments, the one or more regions in the panel comprise one or more loci from one or a plurality of genes for detecting cancer in a high-risk patient population. For example, smokers have much higher rates of lung cancer than the general population. Moreover, smokers can develop other lung conditions that make cancer detection more difficult, such as the development of irregular nodules in the lungs. In some embodiments, the methods described herein detect cancer in high risk patients earlier than is possible for existing methods of cancer detection.

A region may be selected for inclusion in a sequencing panel based on a number of subjects with a cancer that have a tumor marker in that gene or region. A region may be selected for inclusion in a sequencing panel based on prevalence of subjects with a cancer and a tumor marker present in that gene. Presence of a tumor marker in a region may be indicative of a subject having cancer.

In some instances, the panel may be selected using information from one or more databases. The information regarding a cancer may be derived from cancer tumor biopsies or cfDNA assays. A database may comprise information describing a population of sequenced tumor samples. A database may comprise information about mRNA expression in tumor samples. A databased may comprise information about regulatory elements in tumor samples. The information relating to the sequenced tumor samples may include the frequency various genetic variants and describe the genes or regions in which the genetic variants occur. The genetic variants may be tumor markers. A non-limiting example of such a database is COSMIC. COSMIC is a catalogue of somatic mutations found in various cancers. For a particular cancer, COSMIC ranks genes based on frequency of mutation. A gene may be selected for inclusion in a panel by having a high frequency of mutation within a given gene. For instance, COSMIC indicates that 33% of a population of sequenced breast cancer samples have a mutation in TP53 and 22% of a population of sampled breast cancers have a mutation in KRAS. Other ranked genes, including APC, have mutations found only in about 4% of a population of sequenced breast cancer samples. TP53 and KRAS may be included in a sequencing panel based on having relatively high frequency among sampled breast cancers (compared to APC, for example, which occurs at a frequency of about 4%). COSMIC is provided as a non-limiting example, however, any database or set of information may be used that associates a cancer with tumor marker located in a gene or genetic region. In another example, as provided by COSMIC, of 1156 biliary tract cancer samples, 380 samples (33%) carried mutations in TP53. Several other genes, such as APC, have mutations in 4-8% of all samples. Thus, TP53 may be selected for inclusion in the panel based on a relatively high frequency in a population of biliary tract cancer samples.

A gene or region may be selected for a panel where the frequency of a tumor marker is significantly greater in sampled tumor tissue or circulating tumor DNA than found in a given background population. A combination of regions may be selected for inclusion of a panel such that at least a majority of subjects having a cancer will have a tumor marker present in at least one of the regions or genes in the panel. The combination of regions may be selected based on data indicating that, for a particular cancer or set of cancers, a majority of subjects have one or more tumor markers in one or more of the selected regions. For example, to detect cancer 1, a panel comprising regions A, B, C, and/or D may be selected based on data indicating that 90% of subjects with cancer 1 have a tumor marker in regions A, B, C, and/or D of the panel. Alternately, tumor markers may be shown to occur independently in two or more regions in subjects having a cancer such that, combined, a tumor marker in the two or more regions is present in a majority of a population of subjects having a cancer. For example, to detect cancer 2, a panel comprising regions X, Y, and Z may be selected based on data indicating that 90% of subjects have a tumor marker in one or more regions, and in 30% of such subjects a tumor marker is detected only in region X, while tumor markers are detected only in regions Y and/or Z for the remainder of the subjects for whom a tumor marker was detected. Tumor markers present in one or more regions previously shown to be associated with one or more cancers may be indicative of or predictive of a subject having cancer if a tumor marker is detected in one or more of those regions 50% or more of the time. Computational approaches such as models employing conditional probabilities of detecting cancer given a known cancer frequency for a set of tumor markers within one or more regions may be used to predict which regions, alone or in combination, may be predictive of cancer. Other approaches for panel selection involve the use of databases describing information from studies employing comprehensive genomic profiling of tumors with large panels and/or whole genome sequencing (WGS, RNA-seq, Chip-seq, bisulfate sequencing, ATAC-seq, and others). Information gleaned from literature may also describe pathways commonly affected and mutated in certain cancers. Panel selection may be further informed by the use of ontologies describing genetic information.

Genes included in the panel for sequencing can include the fully transcribed region, the promoter region, enhancer regions, regulatory elements, and/or downstream sequence. To further increase the likelihood of detecting tumor indicating mutations only exons may be included in the panel. The panel can comprise all exons of a selected gene, or only one or more of the exons of a selected gene. The panel may comprise of exons from each of a plurality of different genes. The panel may comprise at least one exon from each of the plurality of different genes.

In some aspects, a panel of exons from each of a plurality of different genes is selected such that a determined proportion of subjects having a cancer exhibit a genetic variant in at least one exon in the panel of exons.

At least one full exon from each different gene in a panel of genes may be sequenced. The sequenced panel may comprise exons from a plurality of genes. The panel may comprise exons from 2 to 100 different genes, from 2 to 70 genes, from 2 to 50 genes, from 2 to 30 genes, from 2 to 15 genes, or from 2 to 10 genes.

A selected panel may comprise a varying number of exons. The panel may comprise from 2 to 3000 exons. The panel may comprise from 2 to 1000 exons. The panel may comprise from 2 to 500 exons. The panel may comprise from 2 to 100 exons. The panel may comprise from 2 to 50 exons. The panel may comprise no more than 300 exons. The panel may comprise no more than 200 exons. The panel may comprise no more than 100 exons. The panel may comprise no more than 50 exons. The panel may comprise no more than 40 exons. The panel may comprise no more than 30 exons. The panel may comprise no more than 25 exons. The panel may comprise no more than 20 exons. The panel may comprise no more than 15 exons. The panel may comprise no more than 10 exons. The panel may comprise no more than 9 exons. The panel may comprise no more than 8 exons. The panel may comprise no more than 7 exons.

The panel may comprise one or more exons from a plurality of different genes. The panel may comprise one or more exons from each of a proportion of the plurality of different genes. The panel may comprise at least two exons from each of at least 25%, 50%, 75% or 90% of the different genes. The panel may comprise at least three exons from each of at least 25%, 50%, 75% or 90% of the different genes. The panel may comprise at least four exons from each of at least 25%, 50%, 75% or 90% of the different genes.

The sizes of the sequencing panel may vary. A sequencing panel may be made larger or smaller (in terms of nucleotide size) depending on several factors including, for example, the total amount of nucleotides sequenced or a number of unique molecules sequenced for a particular region in the panel. The sequencing panel can be sized 5 kb to 50 kb. The sequencing panel can be 10 kb to 30 kb in size. The sequencing panel can be 12 kb to 20 kb in size. The sequencing panel can be 12 kb to 60 kb in size. The sequencing panel can be at least 10 kb, 12 kb, 15 kb, 20 kb, 25 kb, 30 kb, 35 kb, 40 kb, 45 kb, 50 kb, 60 kb, 70 kb, 80 kb, 90 kb, 100 kb, 110 kb, 120 kb, 130 kb, 140 kb, or 150 kb in size. The sequencing panel may be less than 100 kb, 90 kb, 80 kb, 70 kb, 60 kb, or 50 kb in size.

The panel selected for sequencing can comprise at least 1, 5, 10, 15, 20, 25, 30, 40, 50, 60, 80, or 100 regions. In some cases, the regions in the panel are selected that the size of the regions are relatively small. In some cases, the regions in the panel have a size of about 10 kb or less, about 8 kb or less, about 6 kb or less, about 5 kb or less, about 4 kb or less, about 3 kb or less, about 2.5 kb or less, about 2 kb or less, about 1.5 kb or less, or about 1 kb or less or less. In some cases, the regions in the panel have a size from about 0.5 kb to about 10 kb, from about 0.5 kb to about 6 kb, from about 1 kb to about 11 kb, from about 1 kb to about 15 kb, from about 1 kb to about 20 kb, from about 0.1 kb to about 10 kb, or from about 0.2 kb to about 1 kb. For example, the regions in the panel can have a size from about 0.1 kb to about 5 kb.

The panel selected herein can allow for deep sequencing that is sufficient to detect low-frequency genetic variants (e.g., in cell-free nucleic acid molecules obtained from a sample). An amount of genetic variants in a sample may be referred to in terms of the minor allele frequency for a given genetic variant. The minor allele frequency may refer to the frequency at which minor alleles (e.g., not the most common allele) occurs in a given population of nucleic acids, such as a sample. Genetic variants at a low minor allele frequency may have a relatively low frequency of presence in a sample. In some cases, the panel allows for detection of genetic variants at a minor allele frequency of at least 0.0001%, 0.001%, 0.005%, 0.01%, 0.05%, 0.1%, or 0.5%. The panel can allow for detection of genetic variants at a minor allele frequency of 0.001% or greater. The panel can allow for detection of genetic variants at a minor allele frequency of 0.01% or greater. The panel can allow for detection of genetic variant present in a sample at a frequency of as low as 0.0001%, 0.001%, 0.005%, 0.01%, 0.025%, 0.05%, 0.075%, 0.1%, 0.25%, 0.5%, 0.75%, or 1.0%. The panel can allow for detection of tumor markers present in a sample at a frequency of at least 0.0001%, 0.001%, 0.005%, 0.01%, 0.025%, 0.05%, 0.075%, 0.1%, 0.25%, 0.5%, 0.75%, or 1.0%. The panel can allow for detection of tumor markers at a frequency in a sample as low as 1.0%. The panel can allow for detection of tumor markers at a frequency in a sample as low as 0.75%. The panel can allow for detection of tumor markers at a frequency in a sample as low as 0.5%. The panel can allow for detection of tumor markers at a frequency in a sample as low as 0.25%. The panel can allow for detection of tumor markers at a frequency in a sample as low as 0.1%. The panel can allow for detection of tumor markers at a frequency in a sample as low as 0.075%. The panel can allow for detection of tumor markers at a frequency in a sample as low as 0.05%. The panel can allow for detection of tumor markers at a frequency in a sample as low as 0.025%. The panel can allow for detection of tumor markers at a frequency in a sample as low as 0.01%. The panel can allow for detection of tumor markers at a frequency in a sample as low as 0.005%. The panel can allow for detection of tumor markers at a frequency in a sample as low as 0.001%. The panel can allow for detection of tumor markers at a frequency in a sample as low as 0.0001%. The panel can allow for detection of tumor markers in sequenced cfDNA at a frequency in a sample as low as 1.0% to 0.0001%. The panel can allow for detection of tumor markers in sequenced cfDNA at a frequency in a sample as low as 0.01% to 0.0001%.

A genetic variant can be exhibited in a percentage of a population of subjects who have a disease (e.g., cancer). In some cases, at least 1%, 2%, 3%, 5%, 10%, 20%, 30%, 40%, 50%, 60%, 70%, 80%, 90%, 95%, or 99% of a population having the cancer exhibit one or more genetic variants in at least one of the regions in the panel. For example, at least 80% of a population having the cancer may exhibit one or more genetic variants in at least one of the regions in the panel.

The panel can comprise one or more regions from each of one or more genes. In some cases, the panel can comprise one or more regions from each of at least 1, 2, 3, 4, 5, 6, 7, 8, 9, 10, 15, 20, 25, 30, 40, 50, or 80 genes. In some cases, the panel can comprise one or more regions from each of at most 1, 2, 3, 4, 5, 6, 7, 8, 9, 10, 15, 20, 25, 30, 40, 50, or 80 genes. In some cases, the panel can comprise one or more regions from each of from about 1 to about 80, from 1 to about 50, from about 3 to about 40, from 5 to about 30, from 10 to about 20 different genes.

The regions in the panel can be selected so that one or more epigenetically modified regions are detected. The one or more epigenetically modified regions can be acetylated, methylated, ubiquitylated, phosphorylated, sumoylated, ribosylated, and/or citrullinated. For example, the regions in the panel can be selected so that one or more methylated regions are detected.

The regions in the panel can be selected so that they comprise sequences differentially transcribed across one or more tissues. In some cases, the regions can comprise sequences transcribed in certain tissues at a higher level compared to other tissues. For example, the regions can comprise sequences transcribed in certain tissues but not in other tissues.

The regions in the panel can comprise coding and/or non-coding sequences. For example, the regions in the panel can comprise one or more sequences in exons, introns, promoters, 3' untranslated regions, 5' untranslated regions, regulatory elements, transcription start sites, and/or splice sites. In some cases, the regions in the panel can comprise other non-coding sequences, including pseudogenes, repeat sequences, transposons, viral elements, and telomeres. In some cases, the regions in the panel can comprise sequences in non-coding RNA, e.g., ribosomal RNA, transfer RNA, Piwi-interacting RNA, and microRNA.

The regions in the panel can be selected to detect (diagnose) a cancer with a desired level of sensitivity (e.g., through the detection of one or more genetic variants). For example, the regions in the panel can be selected to detect the cancer (e.g., through the detection of one or more genetic variants) with a sensitivity of at least 50%, 55%, 60%, 65%, 70%, 75%, 80%, 85%, 90%, 95%, 96%, 97%, 98%, 99%, 99.5%, or 99.9%. The regions in the panel can be selected to detect the cancer with a sensitivity of 100%.

The regions in the panel can be selected to detect (diagnose) a cancer with a desired level of specificity (e.g., through the detection of one or more genetic variants). For example, the regions in the panel can be selected to detect cancer (e.g., through the detection of one or more genetic variants) with a specificity of at least 50%, 55%, 60%, 65%, 70%, 75%, 80%, 85%, 90%, 95%, 96%, 97%, 98%, 99%, 99.5%, or 99.9%. The regions in the panel can be selected to detect the one or more genetic variant with a specificity of 100%.

The regions in the panel can be selected to detect (diagnose) a cancer with a desired positive predictive value. Positive predictive value can be increased by increasing sensitivity (e.g., chance of an actual positive being detected) and/or specificity (e.g., chance of not mistaking an actual negative for a positive). As a non-limiting example, regions in the panel can be selected to detect the one or more genetic variant with a positive predictive value of at least 50%, 55%, 60%, 65%, 70%, 75%, 80%, 85%, 90%, 95%, 96%, 97%, 98%, 99%, 99.5%, or 99.9%. The regions in the panel can be selected to detect the one or more genetic variant with a positive predictive value of 100%.

The regions in the panel can be selected to detect (diagnose) a cancer with a desired accuracy. As used herein, the term "accuracy" may refer to the ability of a test to discriminate between a disease condition (e.g., cancer) and health. Accuracy may be can be quantified using measures such as sensitivity and specificity, predictive values, likelihood ratios, the area under the ROC curve, Youden's index and/or diagnostic odds ratio.

Accuracy may presented as a percentage, which refers to a ratio between the number of tests giving a correct result and the total number of tests performed. The regions in the panel can be selected to detect cancer with an accuracy of at least 50%, 55%, 60%, 65%, 70%, 75%, 80%, 85%, 90%, 95%, 96%, 97%, 98%, 99%, 99.5%, or 99.9%. The regions in the panel can be selected to detect cancer with an accuracy of 100%.

A panel may be selected to be highly sensitive and detect low frequency genetic variants. For instance, a panel may be selected such that a genetic variant or tumor marker present in a sample at a frequency as low as 0.01%, 0.05%, or 0.001% may be detected at a sensitivity of at least 50%, 55%, 60%, 65%, 70%, 75%, 80%, 85%, 90%, 95%, 96%, 97%, 98%, 99%, 99.5%, or 99.9%. Regions in a panel may be selected to detect a tumor marker present at a frequency of 1% or less in a sample with a sensitivity of 70% or greater. A panel may be selected to detect a tumor marker at a frequency in a sample as low as 0.1% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.01% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.001% with a sensitivity of at least 50%, 55%, 60%, 65%, 70%, 75%, 80%, 85%, 90%, 95%, 96%, 97%, 98%, 99%, 99.5%, or 99.9%.

A panel may be selected to be highly specific and detect low frequency genetic variants. For instance, a panel may be selected such that a genetic variant or tumor marker present in a sample at a frequency as low as 0.01%, 0.05%, or 0.001% may be detected at a specificity of at least 50%, 55%, 60%, 65%, 70%, 75%, 80%, 85%, 90%, 95%, 96%, 97%, 98%, 99%, 99.5%, or 99.9%. Regions in a panel may be selected to detect a tumor marker present at a frequency of 1% or less in a sample with a specificity of 70% or greater. A panel may be selected to detect a tumor marker at a frequency in a sample as low as 0.1% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with a specificity of at least 70%, 75%, 80%, 85%, 90%, 95%, 96%, 97%, 98%, 99%, 99.5%, or 99.9%.

A panel may be selected to be highly accurate and detect low frequency genetic variants. A panel may be selected such that a genetic variant or tumor marker present in a sample at a frequency as low as 0.01%, 0.05%, or 0.001% may be detected at an accuracy of at least 70%, 75%, 80%, 85%, 90%, 95%, 96%, 97%, 98%, 99%, 99.5%, or 99.9%. Regions in a panel may be selected to detect a tumor marker present at a frequency of 1% or less in a sample with an accuracy of 70% or greater. A panel may be selected to detect a tumor marker at a frequency in a sample as low as 0.1% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with an accuracy of at least 70%, 75%, 80%, 85%, 90%, 95%, 96%, 97%, 98%, 99%, 99.5%, or 99.9%.

A panel may be selected to be highly predictive and detect low frequency genetic variants. A panel may be selected such that a genetic variant or tumor marker present in a sample at a frequency as low as 0.01%, 0.05%, or 0.001% may have a positive predictive value of at least 70%, 75%, 80%, 85%, 90%, 95%, 96%, 97%, 98%, 99%, 99.5%, or 99.9%.

The concentration of probes or baits used in the panel may be increased (2 to 6 ng/μL) to capture more nucleic acid molecule within a sample. The concentration of probes or baits used in the panel may be at least 2 ng/μL, 3 ng/μL, 4 ng/μL, 5 ng/μL, 6 ng/μL, or greater. The concentration of probes may be about 2 ng/μL to about 3 ng/μL, about 2 ng/μL to about 4 ng/μL, about 2 ng/μL to about 5 ng/μL, about 2 ng/μL to about 6 ng/μL. The concentration of probes or baits used in the panel may be 2 ng/μL or more to 6 ng/μL or less. In some instances this may allow for more molecules within a biological to be analyzed thereby enabling lower frequency alleles to be detected.

Sequencing Depth

DNA enriched from a sample of cfDNA molecules may be sequenced at a variety of read depths to detect low frequency genetic variants in a sample. For a given position, read depth may refer to a number of all reads from all molecules from a sample that map to a position, including original molecules and molecules generated by amplifying original molecules. Thus, for example, a read depth of 50,000 reads can refer to the number of reads from 5,000 molecules, with 10 reads per molecule. Original molecules mapping to a position may be unique and non-redundant (e.g., non-amplified, sample cfDNA).

To assess read depth of sample molecules at a given position, sample molecules may be tracked. Molecular tracking techniques may comprise various techniques for labeling DNA molecules, such as barcode tagging, to uniquely identify DNA molecules in a sample. For example, one or more unique barcode sequences may be attached to one or more ends of a sample cfDNA molecule. In determining read depth at a given position, the number of distinct barcode tagged cfDNA molecules which map to that position can be indicative of the read depth for that position. In another example, both ends of sample cfDNA molecules may be tagged with one of eight barcode sequences. The read depth at a given position may be determined by quantifying the number of original cfDNA molecules at a given position, for instance, by collapsing reads that are redundant from amplification and identifying unique molecules based on the barcode tags and endogenous sequence information.

The DNA may be sequenced to a read depth of at least 3,000 reads per base, at least 4,000 reads per base, at least 5,000 reads per base, at least 6,000 reads per base, at least 7,000 reads per base, at least 8,000 reads per base, at least 9,000 reads per base, at least 10,000 reads per base, at least 15,000 reads per base, at least 20,000 reads per base, at least 25,000 reads per base, at least 30,000 reads per base, at least 40,000 reads per base, at least 50,000 reads per base, at least 60,000 reads per base, at least 70,000 reads per base, at least 80,000 reads per base, at least 90,000 reads per base, at least 100,000 reads per base, at least 110,000 reads per base, at least 120,000 reads per base, at least 130,000 reads per base, at least 140,000 reads per base, at least 150,000 reads per base, at least 160,000 reads per base, at least 170,000 reads per base, at least 180,000 reads per base, at least 190,000 reads per base, at least 200,000 reads per base, at least 250,000 reads per base, at least 500,000 reads per base, at least 1,000,000 reads per base, or at least 2,000,000 reads per base. The DNA may be sequenced to a read depth of about 3,000 reads per base, about 4,000 reads per base, about 5,000 reads per base, about 6,000 reads per base, about 7,000 reads per base, about 8,000 reads per base, about 9,000 reads per base, about 10,000 reads per base, about 15,000 reads per base, about 20,000 reads per base, about 25,000 reads per base, about 30,000 reads per base, about 40,000 reads per base, about 50,000 reads per base, about 60,000 reads per base, about 70,000 reads per base, about 80,000 reads per base, about 90,000 reads per base, about 100,000 reads per base, about 110,000 reads per base, about 120,000 reads per base, about 130,000 reads per base, about 140,000 reads per base, about 150,000 reads per base, about 160,000 reads per base, about 170,000 reads per base, about 180,000 reads per base, about 190,000 reads per base, about 200,000 reads per base, about 250,000 reads per base, about 500,000 reads per base, about 1,000,000 reads per base, or about 2,000,000 reads per base. The DNA can be sequenced to a read depth from about 10,000 to about 30,000 reads per base, 10,000 to about 50,000 reads per base, 10,000 to about 5,000,000 reads per base, 50,000 to about 3,000,000 reads per base, 100,000 to about 2,000,000 reads per base, or about 500,000 to about 1,000,000 reads per base. In some embodiments, DNA can be sequenced to any of the above read depths on a panel size selected from: less than 70,000 bases, less than 65,000 bases, less than 60,000 bases, less than 55,000 bases, less than 50,000 bases, less than 45,000 bases, less than 40,000 bases, less than 35,000 bases, less than 30,000 bases, less than 25,000 bases, less than 20,000 bases, less than 15,000 bases, less than 10,000 bases, less than 5,000 bases, and less than 1,000 bases. For example, the total number of reads for a panel can be as low as 600,000 (3,000 reads per base for 1,000 bases) and as high as $1.4 \times 10^{11}$ (2,000,000 reads per base for 70,000 bases). In some embodiments, DNA can be sequenced to any of the above read depths on a panel size selected from: 5,000 bases to 70,000 bases, 5,000 bases to 60,000 bases, 10,000 bases to 70,000 bases, or 10,000 bases to 70,000 bases.

Read coverage can include reads from one or both strands of a nucleic acid molecule. For example, read coverage may include reads from both strands of at least 5,000, at least 10,000, at least 15,000, at least 20,000, at least 25,000, at least 30,000, at least 35,000, at least 40,000, at least 45,000, or at least 50,000 DNA molecules from the sample mapping to each nucleotide in the of the panel.

A panel may be selected to optimize for a desired read depth given a fixed amount of base reads.

Tagging

In some embodiments of the present disclosure, a nucleic acid library is prepared prior to sequencing. For example, individual polynucleotide fragments in a genomic nucleic acid sample (e.g., genomic DNA sample) can be uniquely identified by tagging with non-unique identifiers, e.g., non-uniquely tagging the individual polynucleotide fragments. In some embodiments, nucleic acid molecules are non-uniquely tagged with respect to one another.

Polynucleotides disclosed herein can be tagged. For example, double-stranded polynucleotides can be tagged with duplex tags, tags that differently label the complementary strands (i.e., the "Watson" and "Crick" strands) of a double-stranded molecule. In some cases the duplex tags are polynucleotides having complementary and non-complementary portions.

Tags can be any types of molecules attached to a polynucleotide, including, but not limited to, nucleic acids, chemical compounds, florescent probes, or radioactive probes. Tags can also be oligonucleotides (e.g., DNA or RNA). Tags can comprise known sequences, unknown sequences, or both. A tag can comprise random sequences, pre-determined sequences, or both. A tag can be double-stranded or single-stranded. A double-stranded tag can be a duplex tag. A double-stranded tag can comprise two complementary strands. Alternatively, a double-stranded tag can comprise a hybridized portion and a non-hybridized portion. The double-stranded tag can be Y-shaped, e.g., the hybridized portion is at one end of the tag and the non-hybridized portion is at the opposite end of the tag. One such example is the "Y adapters" used in Illumina sequencing. Other examples include hairpin shaped adapters or bubble shaped adapters. Bubble shaped adapters have non-complementary sequences flanked on both sides by complementary sequences. In some embodiments, a Y-shaped adaptor comprises a barcode 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides in length. In some combinations. This can be combined with blunt end repair and ligation.

The number of different tags may be greater than an estimated or predetermined number of molecules in the sample. For example, for unique tagging, at least two times as many different tags may be used as the estimated or predetermined number of molecules in the sample.

The number of different identifying tags used to tag molecules in a collection can range, for example, between any of 2, 3, 4, 5, 6, 7, 8, 9, 10, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 at the low end of the range, and any of 50, 100, 500, 1000, 5000 and 10,000 at the high end of the range. The number of identifying tags used to tag molecules in a collection can be at least 2, 3, 4, 5, 6, 7, 8, 9, 10, 15, 20, 25, 30, 35, 40, 45, 50, 55, 60 or more. So, for example, a collection of from 100 billion to 1 trillion molecules can be tagged with from 4 to 100 different identifying tags. A collection of from 100 billion to 1 trillion molecules may be tagged with from 8 to 10,000 different identifying tags. A collection of from 100 billion to 1 trillion molecules may be tagged with from 16 to 10,000 different identifying tags. A collection of from 100 billion to 1 trillion molecules may be tagged with from 16 to 5,000 different identifying tags. A collection of from 100 billion to 1 trillion molecules may be tagged with from 16 to 1,000 different identifying tags.

A collection of molecules can be considered to be "non-uniquely tagged" if there are more molecules in the collection than tags. A collection of molecules can be considered to be non-uniquely tagged if each of at least 1%, at least 5%, at least 10%, at least 15%, at least 20%, at least 25%, at least 30%, at least 35%, at least 40%, at least 45%, or at least or about 50% of the molecules in the collection bears an identifying tag that is shared by at least one other molecule in the collection ("non-unique tag" or "non-unique identifier"). An identifier can comprise a single barcode or two barcodes. A population of nucleic acid molecules can be non-uniquely tagged by tagging the nucleic acid molecules with fewer tags than the total number of nucleic acid molecules in the population. For a non-uniquely tagged population, no more than 1%, 5%, 10%, 15%, 20%, 25%, 30%, 35%, 40%, 45%, or 50% of the molecules may be uniquely tagged. In some embodiments, nucleic acid molecules are identified by a combination of non-unique tags and the start and stop positions or sequences from sequence reads. In some embodiments, the number of nucleic acid molecules being sequenced is less than or equal to the number of combinations of identifiers and start and stop positions or sequences.

In some instances, the tags herein comprise molecular barcodes. Such molecular barcodes can be used to differentiate polynucleotides in a sample. Molecular barcodes can be different from one another. For example, molecular barcodes can have a difference between them that can be characterized by a predetermined edit distance or a Hamming distance. In some instances, the molecular barcodes herein have a minimum edit distance of 1, 2, 3, 4, 5, 6, 7, 8, 9, or 10. To further improve efficiency of conversion (e.g., tagging) of untagged molecular to tagged molecules, one utilizes short tags. For example, a library adapter tag can be up to 65, 60, 55, 50, 45, 40, or 35 nucleotide bases in length. A collection of such short library barcodes can include a number of different molecular barcodes, e.g., at least 2, 4, 6, 8, 10, 12, 14, 16, 18 or 20 different barcodes with a minimum edit distance of 1, 2, 3 or more.

Thus, a collection of molecules can include one or more tags. In some instances, some molecules in a collection can include an identifying tag ("identifier") such as a molecular barcode that is not shared by any other molecule in the collection. For example, in some instances of a collection of molecules, 100% or at least 50%, 60%, 70%, 80%, 90%, 95%, 97%, 98%, or 99% of the molecules in the collection can include an identifier or molecular barcode that is not shared by any other molecule in the collection. As used herein, a collection of molecules is considered to be "uniquely tagged" if each of at least 95% of the molecules in the collection bears an identifier that is not shared by any other molecule in the collection ("unique tag" or "unique identifier"). In some embodiments, nucleic acid molecules are uniquely tagged with respect to one another. A collection of molecules is considered to be "non-uniquely tagged" if each of at least 1%, 5%, 10%, 15%, 20%, 25%, 30%, 35%, 40%, 45%, or 50% of the molecules in the collection bears an identifying tag or molecular barcode that is shared by at least one other molecule in the collection ("non-unique tag" or "non-unique identifier"). In some embodiments, nucleic acid molecules are non-uniquely tagged with respect to one another. Accordingly, in a non-uniquely tagged population no more than 1% of the molecules are uniquely tagged. For example, in a non-uniquely tagged population, no more than 1%, 5%, 10%, 15%, 20%, 25%, 30%, 35%, 40%, 45%, or 50% of the molecules can be uniquely tagged.

A number of different tags can be used based on the estimated number of molecules in a sample. In some tagging methods, the number of different tags can be at least the same as the estimated number of molecules in the sample. In other tagging methods, the number of different tags can be at least two, three, four, five, six, seven, eight, nine, ten, one hundred or one thousand times as many as the estimated number of molecules in the sample. In unique tagging, at least two times (or more) as many different tags can be used as the estimated number of molecules in the sample.

The polynucleotides fragments (prior to tagging) can comprise sequences of any length. For example, polynucleotide fragments (prior to tagging) can comprise at least 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 400, 500, 600, 700, 800, 900, 1000, 1100, 1200, 1300, 1400, 1500, 1600, 1700, 1800, 1900, 2000 or more nucleotides in length. The polynucleotide fragment can be about the average length of cell-free DNA. For example, the polynucleotide fragments can comprise about 160 bases in length. The polynucleotide fragment can also be fragmented from a larger fragment into smaller fragments about 160 bases in length.

Improvements in sequencing can be achieved as long as at least some of the duplicate or cognate polynucleotides bear unique identifiers with respect to each other, that is, bear different tags. However, in certain embodiments, the number of tags used is selected so that there is at least a 95% chance that all duplicate molecules starting at any one position bear unique identifiers. For example, in a sample comprising about 10,000 haploid human genome equivalents of fragmented genomic DNA, e.g., cfDNA, z is expected to be between 2 and 8. Such a population can be tagged with between about 10 and 100 different identifiers, for example, about 2 identifiers, about 4 identifiers, about 9 identifiers, about 16 identifiers, about 25 identifiers, about 36 different identifiers, about 49 different identifiers, about 64 different identifiers, about 81 different identifiers, or about 100 different identifiers.

Nucleic acid barcodes having identifiable sequences, including molecular barcodes, can be used for tagging. For example, a plurality of DNA barcodes can comprise various numbers of sequences of nucleotides. A plurality of DNA barcodes having 2, 3, 4, 5, 6, 7, 8, 9, 10, 11, 12, 13, 14, 15, 16, 17, 18, 19, 20, 21, 22, 23, 24, 25, 26, 27, 28, 29, 30 or more identifiable sequences of nucleotides can be used. When attached to only one end of a polynucleotide, the plurality of DNA barcodes can produce 2, 3, 4, 5, 6, 7, 8, 9, 10, 11, 12, 13, 14, 15, 16, 17, 18, 19, 20, 21, 22, 23, 24, 25, 26, 27, 28, 29, 30 or more different identifiers. Alternatively, when attached to both ends of a polynucleotide, the plurality DNA barcodes can produce 4, 9, 16, 25, 36, 49, 64, 81, 100, 121, 144, 169, 196, 225, 256, 289, 324, 361, 400 or more different identifiers (which is the 2 of when the DNA barcode is attached to only 1 end of a polynucleotide). In one example, a plurality of DNA barcodes having 6, 7, 8, 9 or 10 identifiable sequences of nucleotides can be used. When attached to both ends of a polynucleotide, they produce 36, 49, 64, 81 or 100 possible different identifiers, respectively. In a particular example, the plurality of DNA barcodes can comprise 8 identifiable sequences of nucleotides. When attached to only one end of a polynucleotide, the plurality of DNA barcodes can produce 8 different identifiers. Alternatively, when attached to both ends of a polynucleotide, the plurality of DNA barcodes can produce 64 different identifiers. Samples tagged in such a way can be those with a range of about 10 ng to any of about 200 ng, about 1 μg, about 10 μg of fragmented polynucleotides, e.g., genomic DNA, e.g., cfDNA.

A polynucleotide can be uniquely identified in various ways. A polynucleotide can be uniquely identified by a unique barcode. For example, any two polynucleotides in a sample are attached two different barcodes. A barcode may be a DNA barcode or an RNA barcode. For example, a barcode may be a DNA barcode.

Alternatively, a polynucleotide can be uniquely identified by the combination of a barcode and one or more endogenous sequences of the polynucleotide. The barcode may be a non-unique tag or a unique tag. In some cases, the barcode is a non-unique tag. For example, any two polynucleotides in a sample can be attached to barcodes comprising the same barcode, but the two polynucleotides can still be identified by different endogenous sequences. The two polynucleotides may be identified by information in the different endogenous sequences. Such information includes the sequence of the endogenous sequences or a portion thereof, the length of the endogenous sequences, the location of the endogenous sequences, one or more epigenetic modification of the endogenous sequences, or any other feature of the endogenous sequences. In some embodiments, polynucleotides can be identified by an identifier (comprising one barcode or comprising two barcodes) in combination with start and stop sequences from the sequence read.

A combination of non-unique tags and endogenous sequence information may be used to unambiguously detect nucleic acid molecules. For instance, non-uniquely tagged nucleic acid molecules from a sample ("parent polynucleotides") may be amplified to generate progeny polynucleotides. The parent and progeny polynucleotides may then be sequenced to produce sequence reads. To reduce error, sequence reads may be collapsed to generate a set of consensus sequences. To generate consensus sequences, sequence reads may be collapsed based on sequence information in the non-unique tag and endogenous sequence information, including sequence information at a beginning region of a sequence read, sequence information at an end region of a sequence read, and a length of a sequence read. In some embodiments, a consensus sequence is generated by circular sequencing, in which the same nucleic acid strand is sequenced multiple times in a rolling circle to obtain the consensus sequence. A consensus sequence can be determined on a molecule-by-molecule basis (wherein a consensus sequence is determined over a stretch of bases) or a base-by-base basis (wherein a consensus nucleotide is determined for a base at a given position). In some embodiments, a probabilistic model is constructed to model amplification and sequencing error profiles and used to estimate probabilities of true nucleotide in each position of the molecule. In some embodiments, the probabilistic model parameter estimates are updated based on the error profiles observed in the individual sample or batch of samples being process together or a reference set of samples. In some embodiments, a consensus sequence is determined using barcodes that tag individual cfNA (e.g., cfDNA) molecules from a subject.

An endogenous sequence can be on an end of a polynucleotide. For example, the endogenous sequence can be adjacent (e.g., base in between) to the attached barcode. In some instances the endogenous sequence can be at least 2, 4, 6, 8, 10, 20, 30, 40, 50, 60, 70, 80, 90, or 100 bases in length. The endogenous sequence can be a terminal sequence of the fragment/polynucleotides to be analyzed.

The endogenous sequence may be the length of the sequence. For example, a plurality of barcodes comprising 8 different barcodes can be attached to both ends of each polynucleotide in a sample. Each polynucleotide in the sample can be identified by the combination of the barcodes and about 10 base pair endogenous sequence on an end of the polynucleotide. Without being bound by theory, the endogenous sequence of a polynucleotide can also be the entire polynucleotide sequence.

Also disclosed herein are compositions of tagged poly-nucleotides. The tagged polynucleotide can be single-stranded. Alternatively, the tagged polynucleotide can be double-stranded (e.g., duplex-tagged polynucleotides). Accordingly, this disclosure also provides compositions of duplex-tagged polynucleotides. The polynucleotides can comprise any types of nucleic acids (DNA and/or RNA). The polynucleotides comprise any types of DNA disclosed herein. For example, the polynucleotides can comprise DNA, e.g., fragmented DNA or cfDNA. A set of polynucle-otides in the composition that map to a mappable base position in a genome can be non-uniquely tagged, that is, the number of different identifiers can be at least 2 and fewer than the number of polynucleotides that map to the map-pable base position. The number of different identifiers can also be at least 3, 4, 5, 6, 7, 8, 9, 10, 11, 12, 13, 14, 15, 16, 17, 18, 19, 20, 21, 22, 23, 24, 25 and fewer than the number of polynucleotides that map to the mappable base position.

In some instances, as a composition goes from about 1 ng to about 10 μg or higher, a larger set of different molecular barcodes can be used. For example, between 5 and 100 different library adaptors can be used to tag polynucleotides in a cfDNA sample.

The molecular barcodes can be assigned to any types of polynucleotides disclosed in this disclosure. For example, the molecular barcodes can be assigned to cell-free poly-nucleotides (e.g., cfDNA). Often, an identifier disclosed herein can be a barcode oligonucleotide that is used to tag the polynucleotide. The barcode identifier may be a nucleic acid oligonucleotide (e.g., a DNA oligonucleotide). The barcode identifier can be single-stranded. Alternatively, the barcode identifier can be double-stranded. The barcode identifier can be attached to polynucleotides using any method disclosed herein. For example, the barcode identifier can be attached to the polynucleotide by ligation using an enzyme. The barcode identifier can also be incorporated into the polynucleotide through PCR. In other cases, the reaction may comprise addition of a metal isotope, either directly to the analyte or by a probe labeled with the isotope. Generally, assignment of unique or non-unique identifiers or molecular barcodes in reactions of this disclosure may follow methods and systems described by, for example, U.S. patent appli-cations 2001/0053519, 2003/0152490, 2011/0160078 and U.S. Pat. No. 6,582,908, each of which is entirely incorpo-rated herein by reference.

Identifiers or molecular barcodes used herein may be completely endogenous whereby circular ligation of indi-vidual fragments may be performed followed by random shearing or targeted amplification. In this case, the combi-nation of a new start and stop point of the molecule and the original intramolecular ligation point can form a specific identifier.

Identifiers or molecular barcodes used herein can com-prise any types of oligonucleotides. In some cases, identi-fiers may be predetermined, random, or semi-random sequence oligonucleotides. Identifiers can be barcodes. For example, a plurality of barcodes may be used such that barcodes are not necessarily unique to one another in the plurality. Alternatively, a plurality of barcodes may be used such that each barcode is unique to any other barcode in the plurality. The barcodes can comprise specific sequences (e.g., predetermined sequences) that can be individually tracked. Further, barcodes may be attached (e.g., by ligation) to individual molecules such that the combination of the barcode and the sequence it may be ligated to creates a specific sequence that may be individually tracked. As described herein, detection of barcodes in combination with sequence data of beginning (start) and/or end (stop) portions of sequence reads can allow assignment of a unique identity to a particular molecule. The length or number of base pairs of an individual sequence read may also be used to assign a unique identity to such a molecule. As described herein, fragments from a single strand of nucleic acid having been assigned a unique identity, may thereby permit subsequent identification of fragments from the parent strand. In this way the polynucleotides in the sample can be uniquely or substantially uniquely tagged. A duplex tag can include a degenerate or semi-degenerate nucleotide sequence, e.g., a random degenerate sequence. The nucleotide sequence can comprise any number of nucleotides. For example, the nucleotide sequence can comprise 1 (if using a non-natural nucleotide), 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides. In a particular example, the sequence can comprise 7 nucleotides. In another example, the sequence can comprise 8 nucleotides. The sequence can also comprise 9 nucleotides. The sequence can comprise 10 nucleotides.

A barcode can comprise contiguous or non-contiguous sequences. A barcode that comprises at least 1, 2, 3, 4, 5 or more nucleotides is a contiguous sequence or non-contigu-ous sequence. if the 4 nucleotides are uninterrupted by any other nucleotide. For example, if a barcode comprises the sequence TTGC, a barcode is contiguous if the barcode is TTGC. On the other hand, a barcode is non-contiguous if the barcode is TTXGC, where X is a nucleic acid base.

An identifier or molecular barcode can have an n-mer sequence which may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides in length. A tag herein can comprise any range of nucleotides in length. For example, the sequence can be between 2 to 100, 10 to 90, 20 to 80, 30 to 70, 40 to 60, or about 50 nucleotides in length. A population of barcodes can comprise barcodes of the same length or of different lengths.

The tag can comprise a double-stranded fixed reference sequence downstream of the identifier or molecular barcode. Alternatively, the tag can comprise a double-stranded fixed reference sequence upstream or downstream of the identifier or molecular barcode. Each strand of a double-stranded fixed reference sequence can be, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides in length.

Tagging disclosed herein can be performed using any method. A polynucleotide can be tagged with an adaptor by hybridization. For example, the adaptor can have a nucleo-tide sequence that is complementary to at least a portion of a sequence of the polynucleotide. As an alternative, a polynucleotide can be tagged with an adaptor by ligation.

The barcodes or tags can be attached using a variety of techniques. Attachment can be performed by methods including, for example, ligation (blunt-end or sticky-end) or annealing-optimized molecular-inversion probes. For example, tagging can comprise using one or more enzymes. The enzyme can be a ligase. The ligase can be a DNA ligase. For example, the DNA ligase can be a T4 DNA ligase, *E. coli* DNA ligase, and/or mammalian ligase. The mammalian ligase can be DNA ligase I, DNA ligase III, or DNA ligase IV. The ligase can also be a thermostable ligase. Tags can be ligated to a blunt-end of a polynucleotide (blunt-end ligation). Alternatively, tags can be ligated to a sticky end of a polynucleotide (sticky-end ligation). Efficiency of ligation can be increased by optimizing various conditions. Efficiency of ligation can be increased by optimizing the reaction time of ligation. For example, the reaction time of ligation can be less than 1, 2, 3, 4, 5, 6, 7, 8, 9, 10, 11, 12, 13, 14, 15, 16, 17, 18, 19, or 20 hours. In a particular example, reaction time of ligation is less than 20 hours. Efficiency of ligation can be increased by optimizing the ligase concentration in the reaction. For example, the ligase concentration can be at least 10, 50, 100, 150, 200, 250, 300, 400, 500, or 600 units/microliter. Efficiency can also be optimized by adding or varying the concentration of an enzyme suitable for ligation, enzyme cofactors or other additives, and/or optimizing a temperature of a solution having the enzyme. Efficiency can also be optimized by varying the addition order of various components of the reaction. The end of tag sequence can comprise dinucleotide to increase ligation efficiency. When the tag comprises a non-complementary portion (e.g., Y-shaped adaptor), the sequence on the complementary portion of the tag adaptor can comprise one or more selected sequences that promote ligation efficiency. Such sequences are located at the terminal end of the tag. Such sequences can comprise 1, 2, 3, 4, 5, or 6 terminal bases. Reaction solution with high viscosity (e.g., a low Reynolds number) can also be used to increase ligation efficiency. For example, solution can have a Reynolds number less than 3000, 2000, 1000, 900, 800, 700, 600, 500, 400, 300, 200, 100, 50, 25, or 10. It is also contemplated that roughly unified distribution of fragments (e.g., tight standard deviation) can be used to increase ligation efficiency. For example, the variation in fragment sizes can vary by less than 20%, 15%, 10%, 5%, or 1%. Tagging can also comprise primer extension, for example, by polymerase chain reaction (PCR). Tagging can also comprise any of ligation-based PCR, multiplex PCR, single strand ligation, or single strand circularization. Efficiency of tagging (e.g., by ligation) can be increased to an efficiency of tagging molecules (conversion efficiency) of at least 20%, at least 30%, at least 40%, at least 50%, at least 60%, at least 70%, at least 80%, at least 90%, at least 95%, or at least 98%.

A ligation reaction may be performed in which parent polynucleotides in a sample are admixed with a reaction mixture comprising y different barcode oligonucleotides, wherein y=a square root of n. The ligation can result in the random attachment of barcode oligonucleotides to parent polynucleotides in the sample. The reaction mixture can then be incubated under ligation conditions sufficient to effect ligation of barcode oligonucleotides to parent polynucleotides of the sample. In some embodiments, random barcodes selected from the y different barcode oligonucleotides are ligated to both ends of parent polynucleotides. Random ligation of the y barcodes to one or both ends of the parent polynucleotides can result in production of $y^2$ unique identifiers. For example, a sample comprising about 10,000 haploid human genome equivalents of cfDNA can be tagged with about 36 unique identifiers. The unique identifiers can comprise six unique DNA barcodes. Ligation of 6 unique barcodes to both ends of a polynucleotide can result in 36 possible unique identifiers produced.

In some embodiments, a sample comprising about 10,000 haploid human genome equivalents of DNA is tagged with a number of unique identifiers produced by ligation of a set of unique barcodes to both ends of parent polynucleotides. For example, 64 unique identifiers can be produced by ligation of 8 unique barcodes to both ends of parent polynucleotides. Likewise, 100 unique identifiers can be produced by ligation of 10 unique barcodes to both ends of parent polynucleotides, 225 unique identifiers can be produced by ligation of 15 unique barcodes to both ends of parent polynucleotides, 400 unique identifiers can be produced by ligation of 20 unique barcodes to both ends of parent polynucleotides, 625 unique identifiers can be produced by ligation of 25 unique barcodes to both ends of parent polynucleotides, 900 unique identifiers can be produced by ligation of 30 unique barcodes to both ends of parent polynucleotides, 1225 unique identifiers can be produced by ligation of 35 unique barcodes to both ends of parent polynucleotides, 1600 unique identifiers can be produced by ligation of 40 unique barcodes to both ends of parent polynucleotides, 2025 unique identifiers can be produced by ligation of 45 unique barcodes to both ends of parent polynucleotides, and 2500 unique identifiers can be produced by ligation of 50 unique barcodes to both ends of parent polynucleotides. The ligation efficiency of the reaction can be over 10%, over 20%, over 30%, over 40%, over 50%, over 60%, over 70%, over 80%, or over 90%. The ligation conditions can comprise use of bi-directional adaptors that can bind either end of the fragment and still be amplifiable. The ligation conditions can comprise sticky-end ligation adapters each having an overhang of at least one nucleotide base. In some instances, the ligation conditions can comprise adapters having different base overhangs to increase ligation efficiency. As a non-limiting example, the ligation conditions may comprise adapters with single-base cytosine (C) overhangs (i.e., C-tailed adaptors), single-base thymine (T) overhangs (T-tailed adaptors), single-base adenine (A) overhangs (A-tailed adaptors), and/or single-base guanine (G) overhangs (G-tailed adaptors). The ligation conditions can comprise blunt end ligation, as opposed to tailing. The ligation conditions can comprise careful titration of an amount of adapter and/or barcode oligonucleotides. The ligation conditions can comprise the use of over 2×, over 5×, over 10×, over 20×, over 40×, over 60×, over 80×, (e.g., ~100×) molar excess of adapter and/or barcode oligonucleotides as compared to an amount of parent polynucleotide fragments in the reaction mixture. The ligation conditions can comprise use of a T4 DNA ligase (e.g., NEBNExt Ultra Ligation Module). In an example, 18 microliters of ligase master mix is used with 90 microliter ligation (18 parts of the 90) and ligation enhancer. Accordingly, tagging parent polynucleotides with n unique identifiers can comprise use of a number y different barcodes, wherein y=a square root of n. Samples tagged in such a way can be those with a range of about 10 ng to any of about 100 ng, about 200 ng, about 300 ng, about 400 ng, about 500 ng, about 1 or about 10 μg of fragmented polynucleotides, e.g., genomic DNA, e.g. cfDNA. The number y of barcodes used to identify parent polynucleotides in a sample can depend on the amount of nucleic acid in the sample.

One method of increasing conversion efficiency involves using a ligase engineered for optimal reactivity on single-stranded DNA, such as a ThermoPhage single-stranded DNA (ssDNA) ligase derivative. Such ligases bypass traditional steps in library preparation of end-repair and A-tailing that can have poor efficiencies and/or accumulated losses due to intermediate cleanup steps, and allows for twice the probability that either the sense or anti-sense starting polynucleotide will be converted into an appropriately tagged polynucleotide. It also converts double-stranded polynucleotides that may possess overhangs that may not be sufficiently blunt-ended by the typical end-repair reaction. Optimal reactions conditions for this ssDNA reaction are: 1× reaction buffer (50 millimolar (mM) MOPS (pH 7.5), 1 mM DTT, 5 mM MgCl2, 10 mM KCl). With 50 mM ATP, 25 mg/ml BSA, 2.5 mM MnCl2, 200 pmol 85 nt ssDNA oligomer and 5 U ssDNA ligase incubated at 65° C. for 1 hour. Subsequent amplification using PCR can further convert the tagged single-stranded library to a double-stranded library and yield an overall conversion efficiency of well above 20%. Other methods of increasing conversion rate, e.g., to above 10%, include, for example, any of the following, alone or in combination: annealing-optimized molecular-inversion probes, blunt-end ligation with a well-controlled polynucleotide size range, selection of a high-efficiency polymerase, sticky-end ligation or an upfront multiplex amplification step with or without the use of fusion primers, optimization of end bases in a target sequence, optimization of reaction conditions (including reaction time), and the introduction of one or more steps to clean up a reaction (e.g., of unwanted nucleic acid fragments) during the ligation, and optimization of temperature of buffer conditions. Sticky end ligation may be performed using multiple-nucleotide overhangs. Sticky end ligation may be performed using single-nucleotide overhangs comprising an A, T, C, or G bases.

The present disclosure also provides compositions of tagged polynucleotides. The polynucleotides can comprise fragmented DNA, e.g. cfDNA. A set of polynucleotides in the composition that map to a mappable base position in a genome can be non-uniquely tagged, that is, the number of different identifiers can be at least at least 2 and fewer than the number of polynucleotides that map to the mappable base position. A composition of between about 10 ng to about 10 μg (e.g., any of about 10 ng-1 μg, about 10 ng-100 ng, about 100 ng-10 μg, about 100 ng-1 μg, about 1 μg-10 μg) can bear between any of 2, 5, 10, 50 or 100 to any of 100, 1000, 10,000 or 100,000 different identifiers. For example, between 5 and 100 different identifiers can be used to tag the polynucleotides in such a composition.
Sequencing Tagged polynucleotides can be sequenced to generate sequence reads. For example, a tagged duplex polynucleotide can be sequenced. Sequence reads can be generated from only one strand of a tagged duplex polynucleotide. Alternatively, both strands of a tagged duplex polynucleotide can generate sequence reads. The two strands of the tagged duplex polynucleotide can comprise the same tags. Alternatively, the two strands of the tagged duplex polynucleotide can comprise different tags. When the two strands of the tagged duplex polynucleotide are differently tagged, sequence reads generated from one strand (e.g., a Watson strand) can be distinguished from sequence reads generated from the other strands (e.g., a Crick strand). Sequencing can involve generating multiple sequence reads for each molecule. This occurs, for example, as a result the amplification of individual polynucleotide strands during the sequencing process, e.g., by PCR.

Methods disclosed herein can comprise amplifying of polynucleotides. Amplification can be performed before tagging, after tagging, or both. Polynucleotides amplification can result in the incorporation of nucleotides into a nucleic acid molecule or primer thereby forming a new nucleic acid molecule complementary to a template nucleic acid. The newly formed polynucleotide molecule and its template can be used as templates to synthesize additional polynucleotides. The polynucleotides being amplified can be any nucleic acids, for example, deoxyribonucleic acids, including genomic DNAs, cDNAs (complementary DNA), cfDNAs, and circulating tumor DNAs (ctDNAs). The polynucleotides being amplified can also be RNAs. As used herein, one amplification reaction may comprise many rounds of DNA replication. DNA amplification reactions can include, for example, polymerase chain reaction (PCR). One PCR reaction may comprise 2-100 "cycles" of denaturation, annealing, and synthesis of a DNA molecule. For example, 2-7, 5-10, 6-11, 7-12, 8-13, 9-14, 10-15, 11-16, 12-17, 13-18, 14-19, or 15-20 cycles can be performed during the amplification step. The condition of the PCR can be optimized based on the GC content of the sequences, including the primers. Amplification primers can be chosen to select for a target sequence of interest. Primers can be designed to optimize or maximize conversion efficiency. In some embodiments, primers contain a short sequence between the primers so as to pull out a small region of interest. In some embodiments, primers target nucleosomal regions so that the primers hybridize to areas where nucleosomes are present, as opposed to areas between nucleosomes, because internucleosomal areas are more highly cleaved and therefore less likely to be present as targets.

In some embodiments, regions of the genome are targeted that are differentially protected by nucleosomes and other regulatory mechanisms in cancer cells, the tumor microenvironment, or immune system components (granulocytes, tumor infiltrating lymphocytes, etc). In some embodiments, other regions are targeted that are stable and/or not differentially regulated in tumor cells. Within these regions, differences in coverage, cleavage sites, fragment length, sequence content, sequence content at fragment endpoints, or sequence content of the nearby genomic context can be used to infer the presence or absence of a certain classification of cancer cells (e.g., EGFR mutant, KRAS mutant, ERBb2 amplified, or PD-1 expression cancers), or type of cancer (e.g., lung adenocarcinoma, breast, or colorectal cancer). Such targeting can also enhance the sensitivity and/or specificity of the assay by enhancing coverage at certain sites or the probability of capture. These principles apply to methods of targeting including, but not limited to, ligation plus hybrid capture-based enrichment, amplification-based enrichment, rolling circle-based enrichment with sequence/genomic location specific initiation primers, and other methods. The regions that can be targeted with such methods and subsequent analysis include, but are not limited to, intronic regions, exonic regions, promoter regions, TSS regions, distant regulatory elements, enhancer regions, and super-enhancer regions and/or junctions of the preceding. These methods can also be used to infer the tissue of origin of the tumor and/or a measure of tumor burden in combination with other techniques described herein for determining variants (e.g., germline or somatic variants) contained within the sample. For example, germline variants can determine predisposition for certain types of cancer, while somatic variants can correlate to certain types of cancer specifically based on the affected genes, pathways and percentages of the variants. This information can then be used in combination with epigenetic signatures relating to regulatory mechanisms and/or chemical modifications such as, for example, methylation, hydroxymethylation, acetylation, and/or RNA. The nucleic acid library can involve combined analysis of DNA, DNA modifications and RNA to enhance sensitivity and specificity to the detection of cancer, type of cancer, molecular pathways activated in the specific disease, tissue of origin as well as a measure that corresponds to tumor burden. Approaches for analyzing each of the above have been outlined elsewhere and can be combined for analysis of a single or multiple samples from the same patient, whereby the sample can be derived from various bodily specimens.

Nucleic acid amplification techniques can be used with the assays described herein. Some amplification techniques are the PCR methodologies which can include, but are not limited to, solution PCR and in situ PCR. For example, amplification may comprise PCR-based amplification. Alternatively, amplification may comprise non PCR-based amplification. Amplification of the template nucleic acid may comprise use of one or more polymerases. For example, the polymerase may be a DNA polymerase or an RNA polymerase. In some cases, high fidelity amplification is performed such as with the use of high fidelity polymerase (e.g., Phusion® High-Fidelity DNA Polymerase) or PCR protocols. In some cases, the polymerase may be a high fidelity polymerase. For example, the polymerase may be KAPA HiFi DNA polymerase. The polymerase may also be Phusion DNA polymerase or an Ultra II polymerase. The polymerase may be used under reaction conditions that reduce or minimize amplification biases, e.g., due to fragment length and/or GC content.

Amplification of a single strand of a polynucleotide by PCR will generate copies both of that strand and its complement. During sequencing, both the strand and its complement will generate sequence reads. However, sequence reads generated from the complement of, for example, the Watson strand, can be identified as such because they bear the complement of the portion of the duplex tag that tagged the original Watson strand. In contrast, a sequence read generated from a Crick strand or its amplification product will bear the portion of the duplex tag that tagged the original Crick strand. In this way, a sequence read generated from an amplified product of a complement of the Watson strand can be distinguished from a complement sequence read generated from an amplification product of the Crick strand of the original molecule.

Amplification, such as PCR amplification, is typically performed in rounds. Exemplary rounds of amplification include 1, 2, 3, 4, 5, 6, 7, 8, 9, 10, 11, 12, 13, 14, 15, 16, 17, 18, 19, 20, 25, 30, or more rounds of amplification. Amplification conditions can be optimized, for example, for buffer conditions and polymerase type and conditions. The amplification also can be modified to reduce bias in the sample processing, for example, by reducing non-specific amplification bias, GC content bias, and size bias.

In some embodiments, sequences can be enriched prior to sequencing. Enrichment can be performed for specific target regions or nonspecifically. In some embodiments, targeted genomic regions of interest may be enriched with capture probes ("baits") selected for one or more bait set panels using a differential tiling and capture scheme. A differential tiling and capture scheme uses bait sets of different relative concentrations to differentially tile (e.g., at different "resolutions") across genomic regions associated with baits, subject to a set of constraints (e.g., sequencer constraints such as sequencing load, utility of each bait, etc.), and capture them at a desired level for downstream sequencing. These targeted genomic regions of interest may include single-nucleotide variants (SNVs) and indels (i.e., insertions or deletions). The targeted genomic regions of interest may comprise backbone genomic regions of interest ("backbone regions") or hot-spot genomic regions of interest ("hot-spot regions" or "hotspot regions" or "hot-spots" or "hotspots"). While "hotpots" can refer to particular loci associated with sequence variants, "backbone" regions can refer to larger genomic regions, each of which can have one or more potential sequence variants. For example, a backbone region can be a region containing one or more cancer-associated mutations, while a hotspot can be a locus with a particular mutation associated with recurring cancer or a locus with a particular recurring mutation associated with cancer. Both backbone and hot-spot genomic regions of interest may comprise tumor-relevant marker genes commonly included in liquid biopsy assays (e.g., BRAF, BRCA 1/2, EGFR, KRAS, PIK3CA, ROS1, TP53, and others), for which one or more variants may be expected to be seen in subjects with cancer. In some embodiments, biotin-labeled beads with probes to one or more regions of interest can be used to capture target sequences, optionally followed by amplification of those regions, to enrich for the regions of interest.

The amount of sequencing data that can be obtained from a sample is finite, and constrained by such factors as the quality of nucleic acid templates, number of target sequences, scarcity of specific sequences, limitations in sequencing techniques, and practical considerations such as time and expense. Thus, a "read budget" is a way to conceptualize the amount of genetic information that can be extracted from a sample. A per-sample read budget can be selected that identifies the total number of base reads to be allocated to a test sample comprising a predetermined amount of DNA in a sequencing experiment. The read budget can be based on total reads produced, e.g., including redundant reads produced through amplification. Alternatively, it can be based on number of unique molecules detected in the sample. In certain embodiments read budget can reflect the amount of double-stranded support for a call at a locus. That is, the percentage of loci for which reads from both strands of a DNA molecule are detected.

Factors of a read budget include read depth and panel length. For example, a read budget of 3,000,000,000 reads can be allocated as 150,000 bases at an average read depth of 20,000 reads/base. Read depth can refer to number of molecules producing a read at a locus. In the present disclosure, the reads at each base can be allocated between bases in the backbone region of the panel, at a first average read depth and bases in the hotspot region of the panel, at a deeper read depth. In some embodiments, a sample is sequenced to a read depth determined by the amount of nucleic acid present in a sample. In some embodiments, a sample is sequenced to a set read depth, such that samples comprising different amounts of nucleic acid are sequenced to the same read depth. For example, a sample comprising 300 ng of nucleic acids can be sequenced to a read depth $\frac{1}{10}$ that of a sample comprising 30 ng of nucleic acids. In some embodiments, nucleic acids from two or more different subjects can be added together at a ratio based on the amount of nucleic acids obtained from each of the subjects.

By way of non-limiting example, if a read budget consists of 100,000 read counts for a given sample, those 100,000 read counts will be divided between reads of backbone regions and reads of hotspot regions. Allocating a large number of those reads (e.g., 90,000 reads) to backbone regions will result in a small number of reads (e.g., the remaining 10,000 reads) being allocated to hotspot regions. Conversely, allocating a large number of reads (e.g., 90,000 reads) to hotspot regions will result in a small number of reads (e.g., the remaining 10,000 reads) being allocated to backbone regions. Thus, a skilled worker can allocate a read budget to provide desired levels of sensitivity and specificity. In certain embodiments, the read budget can be between 100,000,000 reads and 100,000,000,000 reads, e.g., between 500,000,000 reads and 50,000,000,000 reads, or between about 1,000,000,000 reads and 5,000,000,000 reads across, for example, 20,000 bases to 100,000 bases.

All polynucleotides (e.g., amplified polynucleotides) can be submitted to a sequencing device for sequencing. Alternatively, a sampling, or subset, of all of the amplified polynucleotides is submitted to a sequencing device for sequencing. With respect to any original double-stranded polynucleotide there can be three results with respect to sequencing. First, sequence reads can be generated from both complementary strands of the original molecule (that is, from both the Watson strand and from the Crick strand). Second, sequence reads can be generated from only one of the two complementary strands (that is, either from the Watson strand or from the Crick strand, but not both). Third, no sequence read may be generated from either of the two complementary strands. Consequently, counting unique sequence reads mapping to a genetic locus will underestimate the number of double-stranded polynucleotides in the original sample mapping to the locus. Described herein are methods of estimating the unseen and uncounted polynucleotides.

The sequencing method can be massively parallel sequencing, that is, simultaneously (or in rapid succession) sequencing any of at least 100, 1000, 10,000, 100,000, 1 million, 10 million, 100 million, or 1 billion polynucleotide molecules.

Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, or Nanopore platforms and any other sequencing methods known in the art.

The method can comprise sequencing at least 1 million, 10 million, 100 million, 500 million, 1 billion, 1.1 billion, 1.2 billion, 1.5 billion, 2 billion, 2.5 billion, 3 billion, 3.5 billion, 4 billion, 4.5 billion, 5 billion, 5.5 billion, 6 billion, 6.5 billion, 7 billion, 8 billion, 9 billion or 10 billion base pairs. In some cases, the methods can comprise sequencing from about 1 billion to about 7 billion, from about 1.1 billion to about 6.8 billion, from about 1.2 billion, to about 6.5 billion, from about 1.1 billion to about 6.4 billion, from about 1.5 billion to about 7 billion, from about 2 billion to about 6 billion, from about 2.5 billion to about 5.5 billion, from about 3 billion to about 5 billion base pairs. For example, the methods can comprise sequencing from about 1.2 billion, to about 6.5 billion base pairs.

Tumor Markers

A tumor marker is a genetic variant associated with one or more cancers. Tumor markers may be determined using any of several resources or methods. A tumor marker may have been previously discovered or may be discovered de novo using experimental or epidemiological techniques. Detection of a tumor marker may be indicative of cancer when the tumor marker is highly correlated a cancer. Detection of a tumor marker may be indicative of cancer when a tumor marker in a region or gene occur with a frequency that is greater than a frequency for a given background population or dataset.

Publicly available resources such as scientific literature and databases may describe in detail genetic variants found to be associated with cancer. Scientific literature may describe experiments or genome-wide association studies (GWAS) associating one or more genetic variants with cancer. Databases may aggregate information gleaned from sources such as scientific literature to provide a more comprehensive resource for determining one or more tumor markers. Non-limiting examples of databases include FANTOM, GTex, GEO, Body Atlas, INSiGHT, OMIM (Online Mendelian Inheritance in Man, omim.org), cBioPortal (cbio-portal.org), CIViC (Clinical Interpretations of Variants in Cancer, civic.genome.wustl.edu), DOCM (Database of Curated Mutations, docm.genome.wustl.edu), and ICGC Data Portal (dcc.icgc.org). In a further example, the COSMIC (Catalogue of Somatic Mutations in Cancer) database allows for searching of tumor markers by cancer, gene, or mutation type. Tumor markers may also be determined de novo by conducting experiments such as case control or association (e.g., genome-wide association studies) studies.

One or more tumor markers may be detected in the sequencing panel. A tumor marker may be one or more genetic variants associated with cancer. Tumor markers can be selected from single nucleotide variants (SNVs), copy number variants (CNVs), insertions or deletions (e.g., indels), gene fusions and inversions. Tumor markers may affect the level of a protein. Tumor markers may be in a promoter or enhancer, and may alter the transcription of a gene. The tumor markers may affect the transcription and/or translation efficacy of a gene. The tumor markers may affect the stability of a transcribed mRNA. The tumor marker may result in a change to the amino acid sequence of a translated protein. The tumor marker may affect splicing, may change the amino acid coded by a particular codon, may result in a frameshift, or may result in a premature stop codon. The tumor marker may result in a conservative substitution of an amino acid. One or more tumor markers may result in a conservative substitution of an amino acid. One or more tumor markers may result in a nonconservative substitution of an amino acid.

One or more of the tumor markers may be a driver mutation. A driver mutation is a mutation that gives a selective advantage to a tumor cell in its microenvironment, through either increasing its survival or reproduction. None of the tumor markers may be a driver mutation. One or more of the tumor markers may be a passenger mutation. A passenger mutation is a mutation that has no effect on the fitness of a tumor cell but may be associated with a clonal expansion because it occurs in the same genome with a driver mutation.

The frequency of a tumor marker may be as low as 0.001%. The frequency of a tumor marker may be as low as 0.005%. The frequency of a tumor marker may be as low as 0.01%. The frequency of a tumor marker may be as low as 0.02%. The frequency of a tumor marker may be as low as 0.03%. The frequency of a tumor marker may be as low as 0.05%. The frequency of a tumor marker may be as low as 0.1%. The frequency of a tumor marker may be as low as 1%.

No single tumor marker may be present in more than 50%, of subjects having the cancer. No single tumor marker may be present in more than 40%, of subjects having the cancer. No single tumor marker may be present in more than 30%, of subjects having the cancer. No single tumor marker may be present in more than 20%, of subjects having the cancer. No single tumor marker may be present in more than 10%, of subjects having the cancer. No single tumor marker may be present in more than 5%, of subjects having the cancer. A single tumor marker may be present in 0.001% to 50% of subjects having cancer. A single tumor marker may be present in 0.01% to 50% of subjects having cancer. A single tumor marker may be present in 0.01% to 30% of subjects having cancer. A single tumor marker may be present in 0.01% to 20% of subjects having cancer. A single tumor marker may be present in 0.01% to 10% of subjects having cancer. A single tumor marker may be present in 0.1% to 10% of subjects having cancer. A single tumor marker may be present in 0.1% to 5% of subjects having cancer.

Detection of a tumor marker may indicate the presence of one or more cancers. Detection may indicate presence of a cancer selected from the group comprising ovarian cancer, pancreatic cancer, breast cancer, colorectal cancer, non-small cell lung carcinoma (e.g., squamous cell carcinoma, or adenocarcinoma) or any other cancer. Detection may indicate the presence of any cancer selected from the group comprising ovarian cancer, pancreatic cancer, breast cancer, colorectal cancer, non-small cell lung carcinoma (squamous cell or adenocarcinoma) or any other cancer. Detection may indicate the presence of any of a plurality of cancers selected from the group comprising ovarian cancer, pancreatic cancer, breast cancer, colorectal cancer and non-small cell lung carcinoma (squamous cell or adenocarcinoma), or any other cancer. Detection may indicate presence of one or more of any of the cancers mentioned in this application.

One or more cancers may exhibit a tumor marker in at least one exon in the panel. One or more cancers selected from the group comprising ovarian cancer, pancreatic cancer, breast cancer, colorectal cancer, non-small cell lung carcinoma (squamous cell or adenocarcinoma), or any other cancer, each exhibit a tumor marker in at least one exon in the panel. Each of at least 3 of the cancers may exhibit a tumor marker in at least one exon in the panel. Each of at least 4 of the cancers may exhibit a tumor marker in at least one exon in the panel. Each of at least 5 of the cancers may exhibit a tumor marker in at least one exon in the panel. Each of at least 8 of the cancers may exhibit a tumor marker in at least one exon in the panel. Each of at least 10 of the cancers may exhibit a tumor marker in at least one exon in the panel. All of the cancers may exhibit a tumor marker in at least one exon in the panel.

If a subject has a cancer, the subject may exhibit a tumor marker in at least one exon or gene in the panel. At least 85% of subjects having a cancer may exhibit a tumor marker in at least one exon or gene in the panel. At least 90%, of subjects having a cancer may exhibit a tumor marker in at least one exon or gene in the panel. At least 92% of subjects having a cancer may exhibit a tumor marker in at least one exon or gene in the panel. At least 95% of subjects having a cancer may exhibit a tumor marker in at least one exon or gene in the panel. At least 96% of subjects having a cancer may exhibit a tumor marker in at least one exon or gene in the panel. At least 97% of subjects having a cancer may exhibit a tumor marker in at least one exon or gene in the panel. At least 98% of subjects having a cancer may exhibit a tumor marker in at least one exon or gene in the panel. At least 99% of subjects having a cancer may exhibit a tumor marker in at least one exon or gene in the panel. At least 99.5% of subjects having a cancer may exhibit a tumor marker in at least one exon or gene in the panel.

If a subject has a cancer, the subject may exhibit a tumor marker in at least one region in the panel. At least 85% of subjects having a cancer may exhibit a tumor marker in at least one region in the panel. At least 90%, of subjects having a cancer may exhibit a tumor marker in at least one region in the panel. At least 92% of subjects having a cancer may exhibit a tumor marker in at least one region in the panel. At least 95% of subjects having a cancer may exhibit a tumor marker in at least one region in the panel. At least 96% of subjects having a cancer may exhibit a tumor marker in at least one region in the panel. At least 97% of subjects having a cancer may exhibit a tumor marker in at least one region in the panel. At least 98% of subjects having a cancer may exhibit a tumor marker in at least one region in the panel. At least 99% of subjects having a cancer may exhibit a tumor marker in at least one region in the panel. At least 99.5% of subjects having a cancer may exhibit a tumor marker in at least one region in the panel.

Detection may be performed with a high sensitivity and/or a high specificity. Sensitivity can refer to a measure of the proportion of positives that are correctly identified as such. In some cases, sensitivity refers to the percentage of all existing tumor markers that are detected. In some cases, sensitivity refers to the percentage of sick people who are correctly identified as having certain disease. Specificity can refer to a measure of the proportion of negatives that are correctly identified as such. In some cases, specificity refers to the proportion of unaltered bases which are correctly identified. In some cases, specificity refers to the percentage of healthy people who are correctly identified as not having certain disease. The non-unique tagging method described previously significantly increases specificity of detection by reducing noise generated by amplification and sequencing errors, which reduces frequency of false positives. Detection may be performed with a sensitivity of at least 95%, 97%, 98%, 99%, 99.5%, or 99.9% and/or a specificity of at least 80%, 90%, 95%, 97%, 98% or 99%. Detection may be performed with a sensitivity of at least 90%, 95%, 97%, 98%, 99%, 99.5%, 99.6%, 99.98%, 99.9% or 99.95%. Detection may be performed with a specificity of at least 90%, 95%, 97%, 98%, 99%, 99.5%, 99.6%, 99.98%, 99.9% or 99.95%. Detection may be performed with a specificity of at least 70% and a sensitivity of at least 70%, a specificity of at least 75% and a sensitivity of at least 75%, a specificity of at least 80% and a sensitivity of at least 80%, a specificity of at least 85% and a sensitivity of at least 85%, a specificity of at least 90% and a sensitivity of at least 90%, a specificity of at least 95% and a sensitivity of at least 95%, a specificity of at least 96% and a sensitivity of at least 96%, a specificity of at least 97% and a sensitivity of at least 97%, a specificity of at least 98% and a sensitivity of at least 98%, a specificity of at least 99% and a sensitivity of at least 99%, or a specificity of 100% a sensitivity of 100%. In some cases, the methods can detect a tumor marker at a sensitivity of sensitivity of about 80% or greater. In some cases, the methods can detect a tumor marker at a sensitivity of sensitivity of about 95% or greater. In some cases, the methods can detect a tumor marker at a sensitivity of sensitivity of about 80% or greater, and a sensitivity of sensitivity of about 95% or greater.

Detection may be highly accurate. Accuracy may apply to the identification of tumor markers in cell free DNA, and/or to the diagnosis of cancer. Statistical tools, such as co-variate analysis described above, may be used to increase and/or measure accuracy. The methods can detect a tumor marker at an accuracy of at least 80%, 90%, 95%, 97%, 98% or 99%, 99.5%, 99.6%, 99.98%, 99.9%, or 99.95%. In some cases, the methods can detect a tumor marker at an accuracy of at least 95% or greater.

Detection Limit/Noise Range

Noise can be introduced through errors in copying and/or reading a polynucleotide. For example, in a sequencing process, a single polynucleotide can first be subject to amplification. Amplification can introduce errors, so that a subset of the amplified polynucleotides may contain, at a particular locus, a base that is not the same as the original base at that locus. Furthermore, in the reading process a base at any particular locus may be read incorrectly. As a consequence, the collection of sequence reads can include a certain percentage of base calls at a locus that are not the same as the original base. In typical sequencing technologies this error rate can be in the single digits, e.g., 2%-3%. In some instances, the error rate can be up to about 10%, up to about 9%, up to about 8%, up to about 7%, up to about 6%, up to about 5%, up to about 4%, up to about 3%, up to about 2%, or up to about 1%. When a collection of molecules that are all presumed to have the same sequence are sequenced, this noise may be sufficiently small that one can identify the original base with high reliability.

However, if a collection of parent polynucleotides includes a subset of polynucleotides that vary at a particular locus, noise can be a significant problem. This can be the case, for example, when cell-free DNA includes not only germline DNA, but DNA from another source, such as fetal DNA or DNA from a cancer cell. In this case, if the frequency of molecules with sequence variants may be in the same range as the frequency of errors introduced by the sequencing process, then true sequence variants may not be distinguishable from noise. This may interfere, for example, with detecting sequence variants in a sample. For example, sequences can have a per-base error rate of 0.5-1%. Amplification bias and sequencing errors introduce noise into the final sequencing product. This noise can diminish sensitivity of detection. As a non-limiting example, sequence variants whose frequency is less than the sequencing error rate can be mistaken for noise.

A noise range or detection limit refers to instances where the frequency of molecules with sequence variants is in the same range as the frequency of errors introduced by the sequencing process. A "detection limit" may also refer to instances where too few variant-carrying molecules are sequenced for the variant to be detected. The frequency of molecules with sequence variants may be in the same range as the frequency of errors as a result of a small amount of nucleic acid molecules. As a non-limiting example, a sampled amount of nucleic acids, e.g. 100 ng, may contain a relatively small number of cell-free nucleic acid molecules, e.g. circulating tumor DNA molecules, such that the frequency of a sequence variant may be low, even though the variant may be present in a majority of circulating tumor DNA molecules. Alternately, the sequence variant may be rare or occur in only a very small amount of the sampled nucleic acids such that a detected variant is indistinguishable from noise and/or sequencing error. As a non-limiting example, at a particular locus, a tumor marker may only be detected in 0.1% to 5% of all reads at that locus.

Distortion can be manifested in the sequencing process as a difference in signal strength, e.g., total number of sequence reads, produced by molecules in a parent population at the same frequency. Distortion can be introduced, for example, through amplification bias, GC bias, or sequencing bias. This may interfere with detecting copy number variation in a sample. GC bias results in the uneven representation of areas rich or poor in GC content in the sequence reading. Also, by providing reads of sequences in greater or less amounts than their actual number in a population, amplification bias can distort measurements of copy number variation.

One way to reduce noise and/or distortion from a single individual molecule or from an ensemble of molecules is to group sequence reads into families derived from original individual molecules to reduce noise and/or distortion from a single individual molecule or from an ensemble of molecules. Efficient conversion of individual polynucleotides in a sample of initial genetic material into sequence-ready tagged parent polynucleotides may increase the probability that individual polynucleotides in a sample of initial genetic material will be represented in a sequence-ready sample. This can produce sequence information about more polynucleotides in the initial sample. Additionally, high yield generation of consensus sequences for tagged parent polynucleotides by high-rate sampling of progeny polynucleotides amplified from the tagged parent polynucleotides, and collapsing of generated sequence reads into consensus sequences representing sequences of parent tagged polynucleotides can reduce noise introduced by amplification bias and/or sequencing errors, and can increase sensitivity of detection. Collapsing sequence reads into a consensus sequence is one way to reduce noise in the received message from one molecule. Using probabilistic functions that convert received frequencies into likelihood or posterior estimates of each of the possible true nucleotides using defined estimates of amplification and sequencing error profiles is another way to reduce noise and/or distortion. With respect to an ensemble of molecules, grouping reads into families and determining a quantitative measure of the families reduces distortion, for example, in the quantity of molecules at each of a plurality of different loci. Again, collapsing sequence reads of different families into consensus sequences eliminate errors introduced by amplification and/or sequencing error. Furthermore, determining frequencies of base calls based on probabilities derived from family information also reduces noise in the received message from an ensemble of molecules. Frequency reporting or tumor marker calls also can be made using a plurality of reference sequences and coverage observations, from which a frequency for observing a tumor marker at a position will be determined. Reference sequences can comprise sequences or marker profiles from healthy individuals or from individuals having a disease or condition, such as cancer. A frequency from "known" reference samples can be used to set a threshold frequency for making a marker detection call. For example, a frequency of 0.1% for a nucleotide having an "A" at a certain position can be used as a threshold for determining whether or not to call a base at that position "A" in a test subject. For example, at least 20, at least 50, at least 100, at least 500, at least 1,000, at least 2,000, at least 3,000, at least 4,000, at least 5,000, at least 6,000, at least 7,000, at least 8,000, at least 9,000, at least 10,000, at least 11,000, at least 12,000, at least 13,000, at least 14,000, at least 15,000, at least 16,000, at least 17,000, at least 18,000, at least 19,000, at least 20,000, at least 30,000, at least 40,000, at least 50,000, at least 60,000, at least 70,000, at least 80,000, at least 90,000, or at least 100,000 reference sequences can be used.

Noise and/or distortion may be further reduced by identifying contaminating molecules from other processed samples by comparing molecule tagging and location information to a collection of observed molecules within the sample being processed or across batches of samples. Noise and/or distortion may be further reduced by comparing genetic variations in a sequence read with genetic variations other sequence reads. A genetic variation observed in one sequence read and again in other sequence reads increases the probability that a detected variant is in fact a tumor marker and not merely a sequencing error or noise. As a non-limiting example, if a genetic variation is observed in a first sequence read and also observed in a second sequence read, a Bayesian inference may be made regarding whether the variation is in fact a genetic variation and not a sequencing error.

Repeated detection of a variant may increase the probability, likelihood, and/or confidence that a variant is accurately detected. A variant can be repeatedly detected by comparing two or more sets of genetic data or genetic variations. The two or more sets of genetic variations can be detected in both samples at multiple time points and different samples at the same time point (for example a re-analyzed blood sample). In detecting a variant in the noise range or below the noise threshold, the re-sampling or repeated detection of a low frequency variant makes it more likely that the variant is in fact a variant and not a sequencing error. Re-sampling can be from the same sample, such as a sample that is re-analyzed or re-run, or from samples at different time points.

Co-variate detection may increase the probability, likelihood, and/or confidence that a variant is accurately detected. For co-variate tumor markers, the presence of one tumor marker is associated with the presence of one or more other tumor markers. Based on the detection of a co-variate genetic variation, it may be possible to infer the presence of an associated co-variate genetic variation, even where the associated genetic variation is present below a detection limit. Alternately, based on the detection of a co-variate genetic variation, the diagnostic confidence indication for the associated genetic variation may be increased. Further, in some instances where a co-variate variant is detected, a detection threshold for a co-variate variant detected below a detection limit may be decreased. Non-limiting examples of co-variate variations or genes include: driver mutations and resistance mutations, driver mutations and passenger mutations. As specific example of co-variants or genes is EGFR L858R activating mutation and EGFR T790M resistance mutation, found in lung cancers. Numerous other co-variate variants and genes are associated with various resistance mutations and will be recognized by one having skill in the art.

In one implementation, using measurements from a plurality of samples collected substantially at once or over a plurality of time points, the diagnostic confidence indication for each variant can be adjusted to indicate a confidence of predicting the observation of the copy number variation (CNV) or mutation or tumor marker. The confidence can be increased by using measurements at a plurality of time points to determine whether cancer is advancing, in remission or stabilized. The diagnostic confidence indication can be assigned by any of a number of statistical methods and can be based, at least in part, on the frequency at which the measurements are observed over a period of time. For example, a statistical correlation of current and prior results can be done. Alternatively, for each diagnosis, a hidden Markov model can be built, such that a maximum likelihood or maximum a posteriori decision can be made based on the frequency of occurrence of a particular test event from a plurality of measurements or a time points. As part of this model, the probability of error and resultant diagnostic confidence indication for a particular decision can be output as well. In this manner, the measurements of a parameter, whether or not they are in the noise range, may be provided with a confidence interval. Tested over time, one can increase the predictive confidence of whether a cancer is advancing, stabilized or in remission by comparing confidence intervals over time. Two sampling time points can be separated by at least about 1 microsecond, 1 millisecond, 1 second, 10 seconds, 30 seconds, 1 minute, 10 minutes, 30 minutes, 1 hour, 12 hours, 1 day, 1 week, 2 weeks, 3 weeks, one month, or one year. Two time points can be separated by about a month to about a year, about a year to about 5 years, or no more than about three months, two months, one month, three weeks, two weeks, one week, one day, or twelve hours. In some embodiments, two time points can be separated by a therapeutic event such as the administration of a treatment or the performance of a surgical procedure. When the two time points are separated by the therapeutic event, CNV or mutations detected can be compared before and after the event.

After sequencing data of cell free polynucleotide sequences is collected, one or more bioinformatics processes may be applied to the sequence data to detect genetic features or variations such as cfDNA characteristics at regulatory elements, nucleosomal spacing/nucleosome binding patterns, chemical modifications of nucleic acids, copy number variation, and mutations or changes in epigenetic markers, including but not limited to methylation profiles, and genetic variants such as SNVs, CNVs, indels, and/or fusions. In some cases, in which copy number variation analysis is desired, sequence data may be: 1) aligned with a reference genome and mapped to individual molecules; 2) filtered; 4) partitioned into windows or bins of a sequence; 5) coverage reads and molecules counted for each window; 6) coverage molecules can then be normalized using a statistical modeling algorithm; and 7) an output file can be generated reflecting discrete copy number states at various positions in the genome. In some cases, the number of coverage reads/molecules or normalized coverage reads aligning to a particular locus of the reference genome is counted. In other cases, in which mutation analysis is desired, sequence data may be 1) aligned with a reference genome and mapped to individual molecules; 2) filtered; 4) frequency of variant bases calculated based on coverage reads for that specific base; 5) variant base frequency normalized using a stochastic, statistical or probabilistic modeling algorithm; and 6) an output file can be generated reflecting mutation states at various positions in the genome. A reference genome for mapping can include the genome of any species of interest. Human genome sequences useful as references can include the hg19 assembly, GRCh38.p4, or any previous or available hg assembly. Such sequences can be interrogated using the genome browser available at genome.ucsc.edu/index.html. Other species genomes include, for example PanTro2 (chimp) and mm9 (mouse).

In some cases, identifiers (such as those including barcodes) can be used to group sequence reads during mutation analysis. In some cases, sequence reads are grouped into families, e.g., by using identifiers or a combination of identifiers and start/stop positions or sequences. In some cases, a base call can be made by comparing nucleotides in one or more families to a reference sequence and determining the frequency of a particular base 1) within each family, and 2) between the families and the reference sequences. A nucleotide base call can be made based on criteria such as the percentage of families having a base at a position. In some cases, a base call is reported if its frequency is greater than a noise threshold as determined by frequency in a plurality of reference sequences (e.g., sequences from healthy individuals). Temporal information from the current and prior analysis of the patient or subject is used to enhance the analysis and determination. In some embodiments, sequence information from the patient or subject is compared to sequence information obtained from a cohort of healthy individuals, a cohort of cancer patients, or germline DNA from the patient or subject. Germline DNA can be obtained, without limitation, from bodily fluid, whole blood, platelets, serum, plasma, stool, red blood cells, white blood cells or leukocytes, endothelial cells, tissue biopsies, synovial fluid, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, or any other bodily fluids. A cohort of cancer patients can have the same type of cancer as the patient or subject, the same stage of cancer as the patient or subject, both, or neither. In some embodiments, a cohort of cancer patients, a cohort of healthy individuals, or germline DNA from the subject is used to provide a baseline frequency of a base at a position, and the baseline frequency is used in making a base call in the subject. Without limitation, a frequency for a base at a position in a cohort of healthy individuals, or germline DNA from the subject can be compared to the frequency of a base detected among sequence reads from the subject.

In some embodiments, the methods and systems of the present disclosure can be used to detect a minor allele frequency (MAF) of 0.025% or lower, 0.05% or lower, 0.075% or lower, or 0.1% or lower. Copy number variation can be measured as a ratio of (1) unique molecule counts (UMCs) for a gene in a test sample to (2) UMCs for that gene in a reference sample (e.g., control sample). In some embodiments, the methods and systems of the present disclosure can be used to detect a copy number variation that is a copy number amplification (CNA). In some embodiments, the methods and systems of the present disclosure can be used to detect a CNA of at least 1.5, 2, 3, 4, 5, 6, 7, 8, 9, 10, 11, 12, 13, 14, 15, 16, 17, 18, 19, 20, 25, 30, 35, 40, 45, 50, 55, 60, or more. In some embodiments, the methods and systems of the present disclosure can be used to detect a copy number variation that is a copy number loss (CNL). In some embodiments, the methods and systems of the present disclosure can be used to detect a CNL of less than 0.9, 0.8, 0.7, 0.6, 0.5, 0.4, 0.3, 0.2, 0.1, or 0.05.

A variety of different reactions and/operations may occur within the systems and methods disclosed herein, including but not limited to: nucleic acid sequencing, nucleic acid quantification, sequencing optimization, detecting gene expression, quantifying gene expression, genomic profiling, cancer profiling, or analysis of expressed markers. Moreover, the systems and methods have numerous medical applications. For example, it may be used for the identification, detection, diagnosis, treatment, monitoring, staging of, or risk prediction of various genetic and non-genetic diseases and disorders including cancer. It may be used to assess subject response to different treatments of the genetic and non-genetic diseases, or provide information regarding disease progression and prognosis.

Computer Control Systems

The present disclosure provides computer control systems that are programmed to implement methods of the disclosure. FIG. 1 shows a computer system 101 that is programmed or otherwise configured to analyze sequencing data, detect tumor markers and determine cancer status. The computer system 101 can regulate various aspects of sequence analysis of the present disclosure, such as, for example, matching data against known sequences and variants. The computer system 101 can be an electronic device of a user or a computer system that is remotely located with respect to the electronic device. The electronic device can be a mobile electronic device.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure. The CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user (e.g., a physician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 930.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, information about cancer diagnosis. Examples of UI's include, without limitation, a graphical user interface (GUI) and web-based user interface.

In one aspect provided herein is a system comprising a computer comprising a processor and computer memory, wherein the computer is in communication with a communications network, and wherein computer memory comprises code which, when executed by the processor, (1) receives sequence data into computer memory from the communications network; (2) determines whether a genetic variant in the sequence data represents a germline mutant or a somatic cell mutant, using the methods described herein; and (3) reports out, over the communications network, the determination.

The communications network can be any available network that connects to the internet. The communications network can utilize, for example, a high-speed transmission network including, without limitation, Broadband over Powerlines (BPL), Cable Modem, Digital Subscriber Line (DSL), Fiber, Satellite, and Wireless.

In one aspect provided herein is a system comprising: a local area network; one or more DNA sequencers comprising computer memory configured to store DNA sequence data which are connected to the local area network; a bioinformatics computer comprising a computer memory and a processor, which computer is connected to the local area network; wherein the computer further comprises code which, when executed, copies DNA sequence data stored on a DNA sequencer, writes the copied data to memory in the bioinformatics computer, and performs steps as described herein.

Methods and systems of the present disclosure can be implemented by way of one or more algorithms. An algorithm can be implemented by way of software upon execution by the central processing unit 105. The algorithm can, for example, determine whether a cancer is present and/or progressing.

All publications and patent applications mentioned in this specification are herein incorporated by reference to the same extent as if each individual publication or patent application were specifically and individually indicated to be incorporated by reference.

From the foregoing it will be appreciated that, although specific embodiments of the present disclosure have been described herein for purposes of illustration, various modifications may be made without deviating from the spirit and scope of the present disclosure. Accordingly, the present disclosure is not limited except as by the appended claims.

While preferred embodiments of the present disclosure have been shown and described herein, it will be obvious to those skilled in the art that such embodiments are provided by way of example only. It is not intended that the present disclosure be limited by the specific examples provided within the specification. While the present disclosure has been described with reference to the aforementioned specification, the descriptions and illustrations of the embodiments herein are not meant to be construed in a limiting sense. Numerous variations, changes, and substitutions will now occur to those skilled in the art without departing from the present disclosure. Furthermore, it shall be understood that all aspects of the present disclosure are not limited to the specific depictions, configurations or relative proportions set forth herein which depend upon a variety of conditions and variables. It should be understood that various alternatives to the embodiments of the present disclosure described herein may be employed in practicing the present disclosure. It is therefore contemplated that the present disclosure shall also cover any such alternatives, modifications, variations or equivalents. It is intended that the following claims define the scope of the present disclosure and that methods and structures within the scope of these claims and their equivalents be covered thereby.

EXAMPLES

Example 1: Next Generation Sequencing Assay for Detection of ctDNA in Early Stage Cancer Patients Deidentified cfDNA sequencing data from 10288 advanced cancer patients (pts) undergoing clinical circulating tumor DNA testing (73 genes of Table 2) were included in this study. CfDNA was extracted from plasma and quantified. A DNA library was prepared and sequenced to 15,000× average read depth. Using Ingenuity Variant Analysis, point mutations and small indels suspicious for germline origin (allele fraction 40-60%) were classified following American College of Medical Genetics and Genomics guidelines. More than 50 cancer types were studied, including lung (40%), breast (20%), colorectal cancer (CRC) (8%), prostate (6%), and pancreas (3%). The average age of the subjects was 63.6 years (range: 18-95), and 42% were male. Of 34,873 putative germline variants identified, 520 (1.5%) were pathogenic or likely pathogenic (PV), 16,939 (49%) were of uncertain significance, and 17,414 (50%) were benign or likely benign. Of the 250 subjects (2.4%) with hereditary cancer syndrome gene PVs, 83 were excluded due to high level of somatic tumor burden leaving 167 (1.6%) with putative germline PVs; rates were higher in patients under 50 years of age vs those 50 years and older overall (3.3% vs 1.4%, p=0.02) and in breast cancer patients (4.3% vs 1.5%, p=0.03). Results are shown in Table 4.

The observed frequency of incidentally identified putative germline PVs was lower than the true germline rate, but these findings illustrate that detection from cfDNA is clinically feasible. Importantly, incidental germline findings could impact oncology treatment planning (e.g. PARP inhibitors for BRCA1/2 mutations) and could benefit families via increased surveillance/primary prevention.

Example 2: Discrimination of Germline EGFR T790M Mutations in Cell-Free DNA

To address whether genomic analysis of plasma cfDNA could permit simultaneous tumor and germline genotyping, with accurate resolution of tumor-derived variants and germline variants, somatic and germline variants in the EGFR gene, including known germline variants and a group of oncogenic mutations present in 10-20% of NSCLC patients, were studied. One EGFR mutation, T790M, can be detected rarely as a germline variant where its presence has been associated with familial lung cancer. EGFR T790M is more commonly seen as an acquired somatic mutation after a patient with NSCLC develops resistance to EGFR tyrosine kinase inhibitors (TKIs). Lung cancers harboring T790M-mediated resistance after initial therapy exhibit sensitivity to a third-generation EGFR TKI, osimertinib.

A 49-year-old never smoker with a family history of lung cancer presented with metastatic lung adenocarcinoma with primary progression on the second-generation EGFR tyrosine kinase inhibitor (TKI) afatinib. Initial tissue genotyping had shown EGFR L858R and T790M mutations, as well as other somatic alterations in CDKN2A, TP53, and CTNNB1. Due to the L858R mutation in EGFR, first-line afatinib was started. However, the patient returned with progressive brain metastases after only two months of therapy. At the time of referral, plasma next generation sequencing (NGS) demonstrated the previously observed EGFR L858R, TP53, and CTNNB1 variants at an allelic fraction (AF) of 1.4-5.3%, while the EGFR T790M allele was detected at 50.9% AF, as seen in Table 5.

TABLE 4

| PV by Cancer Type (N) | | | | | | | |
|---|---|---|---|---|---|---|---|
| Gene | ALL | Ovarian | Pancreatic | Prostate | Breast | Lung | CRC[1] | Other |
| BRCA2 | 78 | 3 | 7 | 18 | 26 | 17 | 1 | 6 |
| BRCA1 | 38 | 11 | 1 | | 9 | 12 | 1 | 4 |
| TP53 | 16 | | | | 4 | 8 | 2 | 2 |
| CDKN2A | 10 | | 1 | | 3 | 2 | | 4 |
| ATM | 5 | | 1 | | 2 | 2 | | |
| KIT | 4 | | | | 1 | 2 | 1 | |
| NF1 | 4 | | | 1 | | 1 | | 2 |
| RET | 4 | | 1 | | | 2 | | 1 |
| APC | 4 | | | | | | 1 | 3 |
| RB1 | 2 | | | | | | | 2 |
| MLH1 | 1 | | | | | | 1 | |
| SMAD4 | 1 | | | | | | 1 | |
| | | | | | | | | |
| TOTAL | 167 | 14 | 11 | 19 | 45 | 46 | 8 | 24 |
| # patients | 10288 | 205 | 328 | 577 | 2047 | 4136 | 830 | 2165 |
| % of patients | 1.6% | 6.8% | 3.4% | 3.3% | 2.2% | 1.1% | 1.0% | 1.1% |

[1]Lynch genes not sequenced except for MLH1 exon 12

TABLE 5

| Alteration | Time 1 (AF) | Time 2 (AF) | Time 3 (AF) |
|---|---|---|---|
| EGFR L858R | 5.3% | 0.6% | 18.1% |
| EGFR T790M | 50.9% | 49.2% | 54.4% |
| EGFR C797S | ND | ND | 1.3% |
| EGFR Q787Q | 51.5% | 48.7% | 54.8% |
| TP53 P278R | 3.8% | ND | 19.7% |

The patient was initiated on osimertinib, an EGFR tyrosine kinase inhibitor (TKI) which is active in the setting of EGFR T790M-mediated resistance to initial EGFR TKIs, and had clinical benefit lasting nine months, at which time scans showed early progression in the lung. Repeat plasma NGS showed the EGFR L858R variant at 0.6% AF but T790M was relatively stable at 49.2% AF (FIG. 7, where 701 is EGFR L858R; 702 is EGFR T790M; 703 is EGFR Q787Q and 704 is TP53 P278R). The patient then received investigational therapy on a clinical trial and developed further disease progression. Repeat plasma NGS at this time demonstrated increased levels of the EGFR L858R at 18% AF, T790M at 54% AF, and a third EGFR mutation that mediates acquired resistance to osimertinib, C797S, at 1.3% AF. This mutation may mediate acquired resistance to osimertinib, and the presence of an EGFR T790M mutation at initial diagnosis of the lung cancer, along with its high AF at cfDNA analysis, and the family history of lung cancer, raised the suspicion that the EGFR T790M mutation might have represented a germline risk allele.

Droplet Digital PCR

Blood (6-10 mL) was collected into EDTA lavender capped vacutainer tubes and centrifuged for 10 min at 1200 g. The plasma supernatant was further cleared by centrifugation for 10 min at 3000 g. The second supernatant was stored in cryostat tubes at −80° C. until use. Cell free DNA was isolated using the QIAmp Circulating Nucleic Acid Kit (Qiagen) and droplet digital PCR (ddPCR) was performed. Briefly, TaqMan PCR reaction mixtures were assembled from a 2×ddPCR Mastermix (Bio-Rad) and 40× TaqMan probes/primers made for each assay. Droplets were generated using an automated droplet Generator (Bio-RAD). PCR was performed to endpoint. After PCR, droplets were read on either a QX100 or QX200 droplet reader (Bio-Rad). Analysis of the ddPCR data was performed with QuantaSoft analysis software (Bio-Rad). All ddPCR reagents were ordered from Bio-Rad. All primer and probes for were custom-ordered from Life Technologies. Primers and conditions were as follows.

EGFR L858R forward primer, 5'-GCAGCATGTCAA-GATCACAGATT-3' (SEQ ID NO. 1); reverse primer, 5'-CCTCCTTCTGCATGGTATTCTTTCT-3' (SEQ ID NO. 2); probe sequences: 5'-VIC-AGTTTGGCCAGCCCAA-MGB-NFQ-3' (SEQ ID NO. 3), 5'-FAM-AGTTTGGCCCGCCCAA-MGB-NFQ-3' (SEQ ID NO. 4). Cycling conditions: 95° C.×10 min (1 cycle), 40 cycles of 94° C.×30 s and 58° C.×1 min, and 10° C. hold.

EGFR del 19 forward primer, 5'-GTGAGAAAGT-TAAAATTCCCGTC-3' (SEQ ID NO. 5); reverse primer, 5'-CACACAGCAAAGCAGAAAC-3' (SEQ ID NO. 6); probe sequences: 5'-VIC-ATCGAGGATTTCCTTGTTG-MGB-NFQ- 3' (SEQ ID NO. 7), 5'-FAM-AGGAAT-TAAGAGAAGCAACATC-MGB-NFQ-3' (SEQ ID NO. 8). Cycling conditions: 95° C.×10 min (1 cycle), 40 cycles of 94° C.×30 s and 55° C.×1 min, followed by 10° C. hold.

EGFR T790M, forward primer, 5'-GCCTGCTGGG-CATCTG-3' (SEQ ID NO. 9), reverse primer, 5'-TCTTTGTGTTCCCGGACATAGTC-3' (SEQ ID NO.

10); probe sequences: 5'-VIC-ATGAGCTGCGTGATGAG-MGB-NFQ-3' (SEQ ID NO. 11), 5'-FAM-ATGAGCTG-CATGATGAG-MGB-NFQ-3' (SEQ ID NO. 12). Cycling conditions: 95° C.×10 min (1 cycle), 40 cycles of 94° C.×30 s and 58° C.×1 min, followed by 10° C. hold.

Plasma Next-Generation Sequencing cfDNA was isolated from 10 ml of whole blood drawn in cell-free DNA tubes, enriched by hybrid capture targeting exons of 70 genes and critical introns of 6 genes, and sequenced to an average depth of ~15,000× on an Illumina NextSeq500 sequencer.

Germline Sequencing

For selected cases, de-identified buffy coat specimens were provided and genomic DNA was extracted for Sanger sequencing of EGFR.

Statistical Analysis

The relationship between AF of EGFR driver mutation and measures of copy number variation within the heterozygous group of variants was analyzed using a linear regression. The probability density function of the distribution of the standard deviation and mean AFs for individual cases was estimated using a Gaussian approximation, and outliers were identified using the Tukey method. A 95% confidence interval was determined for EGFR T790M prevalence in each diagnosis of interest. The prevalence among the different diagnoses was compared using a two-tailed Fisher's exact test.

Results

Figure 2A:
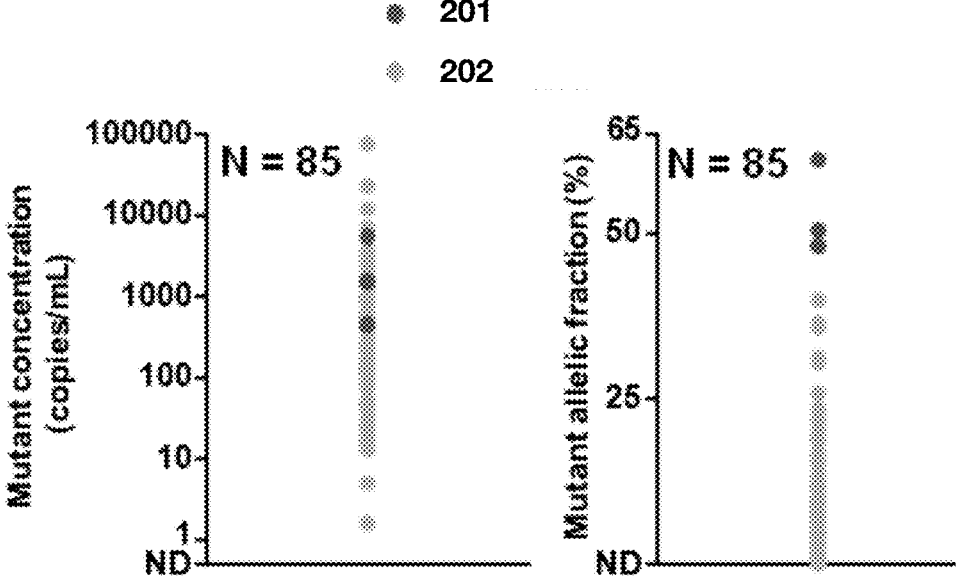
FIG. 2A shows that germline T790M mutations (201—black dots) are present at a similar concentration as somatic T790M mutations (202—grey dots), but at a higher allelic fraction (AF).
Figure 2B:
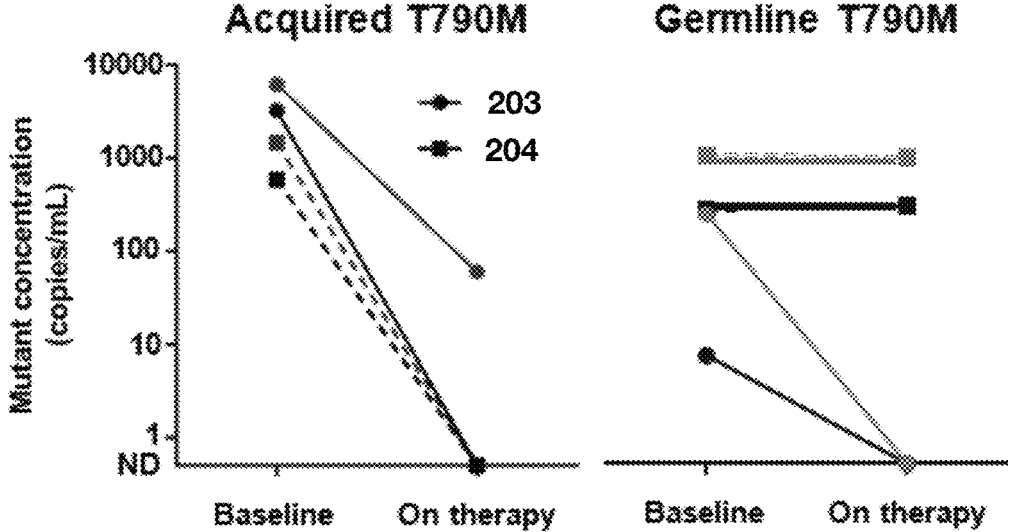
FIG. 2B shows that the concentrations of somatic EGFR mutations in four patients on treatment decrease while the concentration of germline EGFR T790M remains constant (203 represents EGFR driver mutation and 204 represents EGFR T790M).

Of 85 patients with advanced NSCLC who had an EGFR T790M mutation, three were known to carry a germline EGFR T790M mutation based on prior germline sequencing, whereas the remainder had acquired EGFR T790M after TKI treatment. Studying the absolute concentration of T790M alleles in copies/mL of plasma, some cases with somatic T790M carried an even higher concentration of mutant T790M alleles in plasma than the three cases with germline EGFR T790M (FIG. 2A). By contrast, with the AF of T790M, calculated as the proportion of copies of mutant T790M out of all mutant or wildtype variants at that locus, the AF of the three germline cases hovered around 50%, higher than the AF of the somatic T790M cases (FIG. 2A). Changes in the levels of somatic versus germline EGFR mutations in plasma cfDNA upon treatment with third-generation EGFR TKIs such as osimertinib were then studies. In patients carrying acquired EGFR T790M after first-generation TKI resistance, the concentration of both the EGFR T790M mutations and the driver mutations (e.g. L858R or exon 19 deletion) decreased dramatically in response to therapy (FIG. 2B). By contrast, in patients with germline EGFR T790M mutations, the EGFR driver mutation responded on therapy while the EGFR T790M levels stayed relatively stable (FIG. 2B). These data provided proof-of-concept that quantitation of variant levels in plasma cfDNA can be used to discriminate between somatic and germline origins of tumor-associated mutations.

Figure 2C:
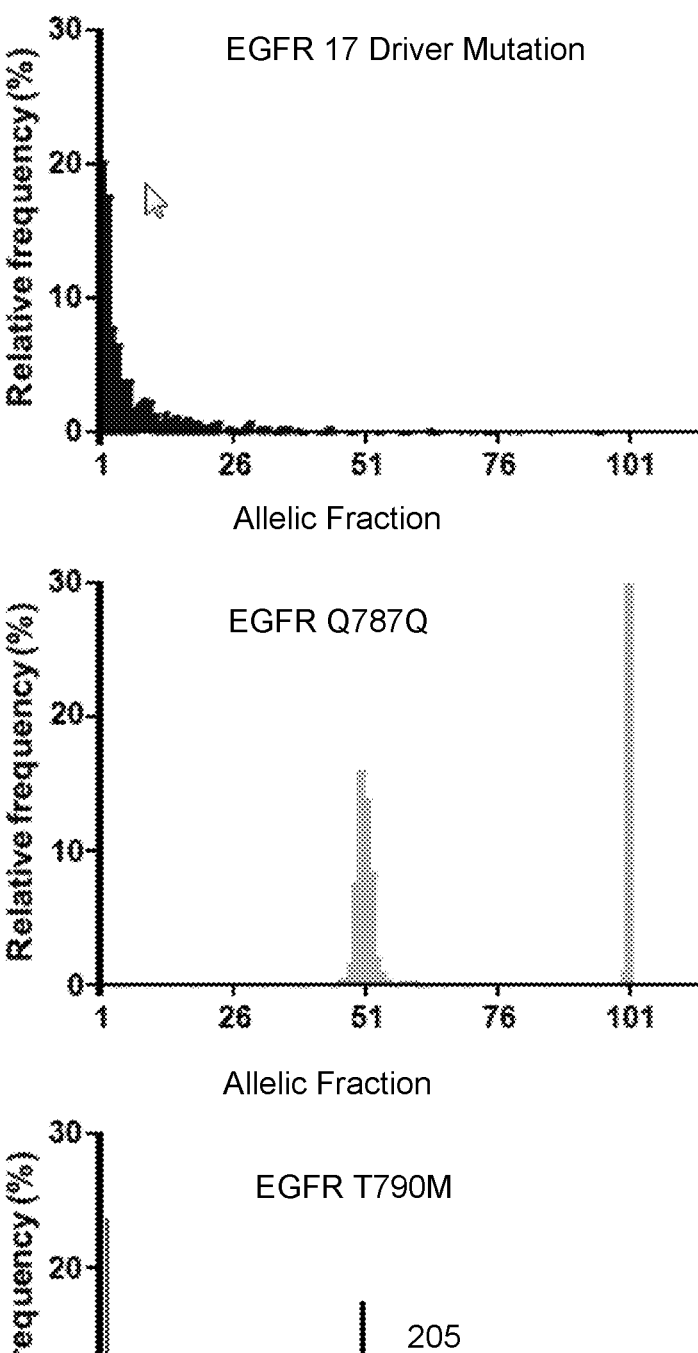
FIG. 2C shows that the AF distribution for EGFR T790M (bottom plot) across plasma NGS results for 950 cases includes a somatic peak also seen with EGFR driver mutations (top plot), as well as a heterozygous peak (arrow 205) also seen more clearly with a common SNP (EGFR Q787Q, middle plot).

Next-generation sequencing (NGS) has the potential to capture a broad range of variants across a number of cancer-related genes. To further investigate the behavior of germline and somatic EGFR mutations in plasma cfDNA, the exonic regions of 70 oncogenes and tumor suppressor genes, and intronic regions of 6 genes in which oncogenic rearrangements occur, were sequenced. A database of clinical plasma NGS results was queried to study the distribution of somatic and germline EGFR mutations, resulting in the identification of test sets of 950 consecutive NSCLC samples for each of the following: known somatic mutations (L858R and exon 19 deletions), a common germline single nucleotide polymorphism (SNP) within the EGFR tyrosine kinase domain (Q787Q)(17), and T790M, and plotted the AF distribution of each (FIG. 2C). The distribution of known SNPs comprised two discrete, normally distributed probability distributions centered at AFs of 50% and 100%, compatible with heterozygosity and homozygosity of the Q787Q allele. The distribution of the known somatic alterations, L858R and exon 19 deletions, by contrast, demonstrated an exponential decay distribution beginning at the assay's limit of detection with the long tail extending to AFs exceeding 90%, compatible with somatic AFs that varied substantially but that were generally low (<5%). The distribution of T790M conformed predominantly to this same somatic distribution. However, there was a minor but discrete, normally-distributed sub-population centered at 50% AF (FIG. 2C, arrow 205). This pattern supports study of variant AF in cfDNA as a method for categorizing variants like EGFR T790M, which may be of either germline or somatic origin.

Figure 3A:
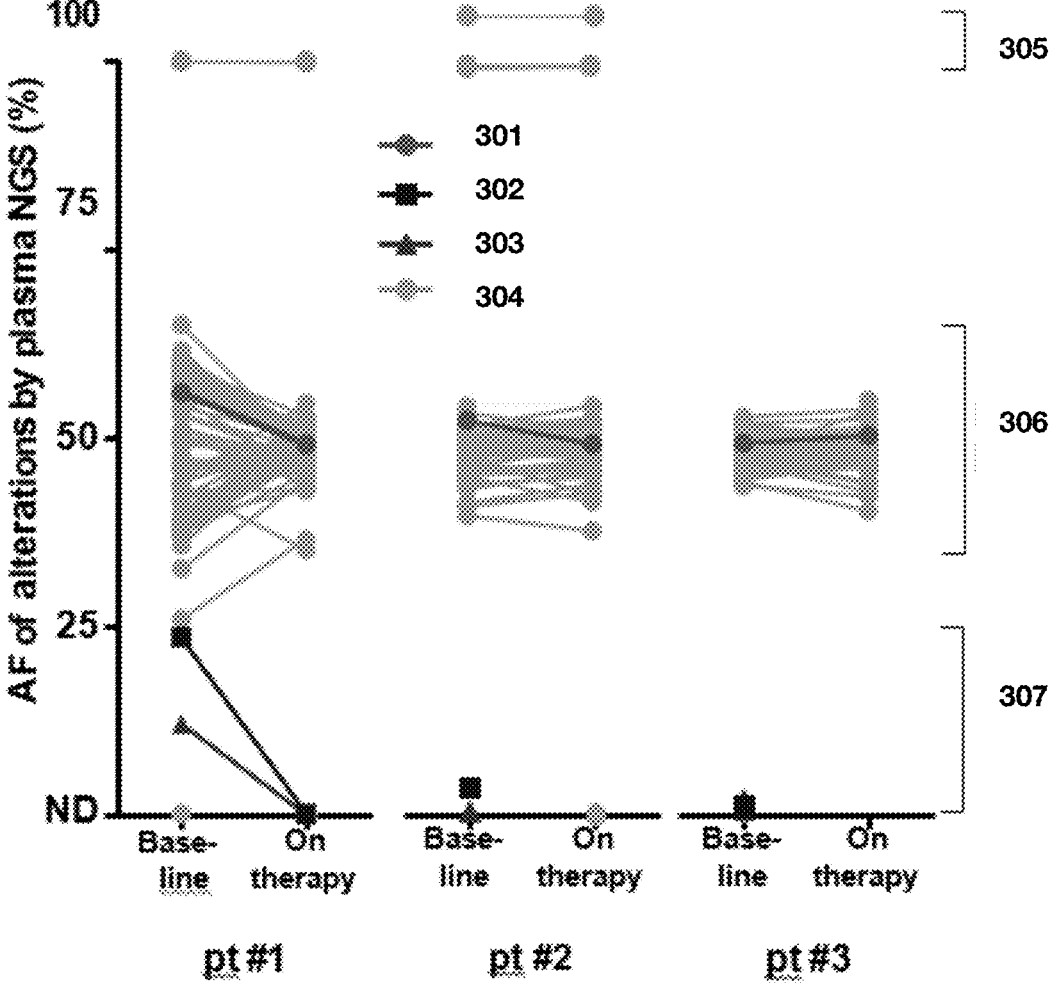
FIG. 3A shows plasma NGS for pre-treatment and on-treatment plasma specimens from three initial cases, all positive for germline EGFR T790M. Three groups of variants were evident among all coding and non-coding variants detected, corresponding to the expected AF of homozygous, heterozygous, and tumor-derived variants. Variants in the tumor-derived group responded on therapy while variants in the homozygous and heterozygous groups remained at a relatively constant AF.

AF distribution was further studied by performing plasma NGS on pre-treatment and on-treatment plasma specimens from three cases with germline EGFR T790M known to harbor EGFR driver mutations in their cancer (two with L858R, one with L861Q). Studying the AFs of all coding and non-coding variants identified on plasma NGS, three groups of variants were clearly visualized (FIG. 3A, where 301 is EGFR T790M; 302 is EGFR driver mutation; 303 is TP53 mutation; 304 is other alterations; 305 is homozygous band; 306 is heterozygous band and 307 is tumor band). The lowest AF group of variants includes the EGFR driver and TP53 mutations, representing cancer-derived variants. The highest AF group of variants was centered around 100% AF, representing homozygous germline variants. Finally, a middle group of variants centered around 50%, which included the known germline EGFR T790M mutations and represented heterozygous germline variants. On treatment with a third-generation EGFR TKI (two with osimertinib, one with ASP7283), the low AF cancer-derived variants decreased or became undetectable (24%→0.2%, 3.7%→ND, 1.1%→ND), the low AF cancer-derived variants decreased or became undetectable. By contrast, the middle group of heterozygous germline variants changed only modestly and remained centered around 50%→AF (56%→49%, 52%→49%, 49%→50%). Interestingly, some of these heterozygous variants appeared to have an increase in AF as the cancer responded to therapy while others had a decrease in AF. These changes in the heterozygous group on treatment could represent a reduction in tumor-derived copy number variation, leading to a change in the variant AF in cfDNA.

Figure 7:
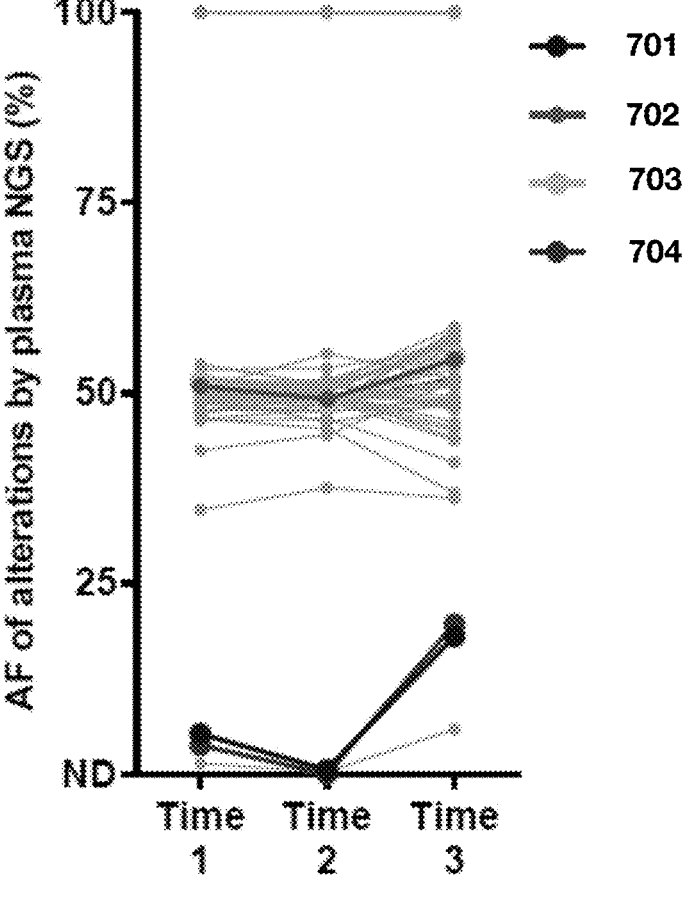
FIG. 7 shows an AF plot of coding and noncoding variants detected at three timepoints (AF of the TP53 mutation at time 2 imputed at 0%). The EGFR T790M mutation is seen within a band of variants that includes the common SNP (EGFR Q787Q), suspicious for an incidentally detected germline EGFR T790M.

All coding and noncoding variants from plasma NGS of the initial case presented above were then studied (Table 5). This revealed a pattern similar to the germline EGFR T790M cases studied, where the patient's EGFR T790M mutation fell within the heterozygous group of variants, and the AF changed minimally on therapy as compared to the EGFR L858R mutation (FIG. 7).

Figure 3B:
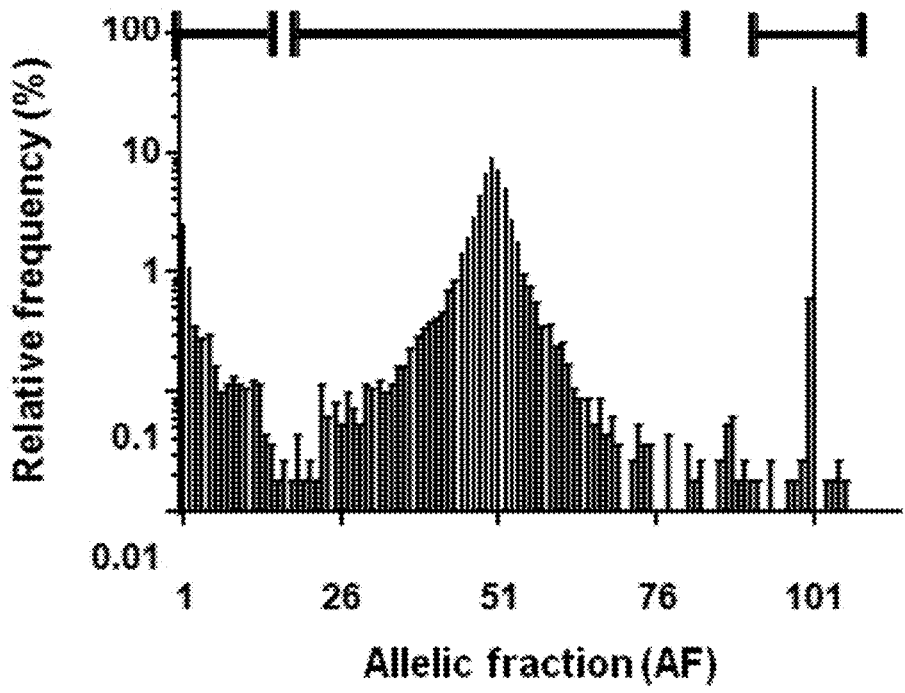
FIG. 3B shows plasma NGS results from an additional 102 cases, for a total of 105 cases. A trimodal distribution was seen with peaks near 0% (likely tumor-derived), 49% (likely heterozygous), and 100% (likely homozygous) for all coding and non-coding variants detected across the 105 cases.
Figure 3C:
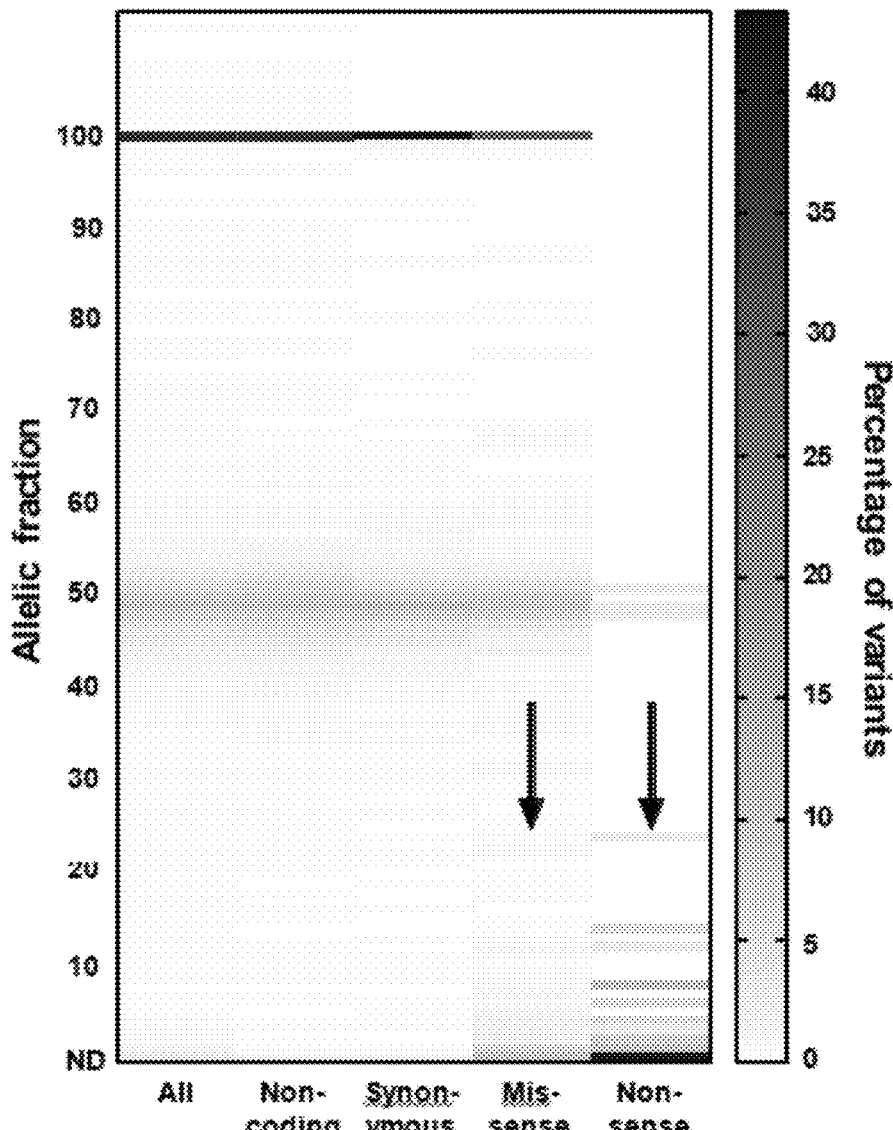
FIG. 3C shows that, for missense and nonsense variants, there was enrichment at low AF (arrows), where tumor-derived variants would be expected to be found. By contrast, synonymous variants, likely reflecting benign germline polymorphisms, were enriched around 50% and 100% AF.

To further study the relationship between tumor content in cfDNA and heterozygous copy number variation, a database was queried for an additional 63 plasma NGS cases which were positive for EGFR T790M and 39 plasma NGS cases positive for an EGFR driver mutation without T790M. These 105 cases each had a median of 107 coding and noncoding variants detected. Looking at the AF distribution of all 10,702 variants in total (FIG. 3B), a trimodal distribution is clearly seen, with three AF peaks at ~0%, 49%, and 100%. Compared to noncoding exonic and intronic variants, coding missense and nonsense variants were enriched in the low AF group of variants (FIG. 3C), consistent with this representing a group of cancer-derived variants.

Figure 4A:
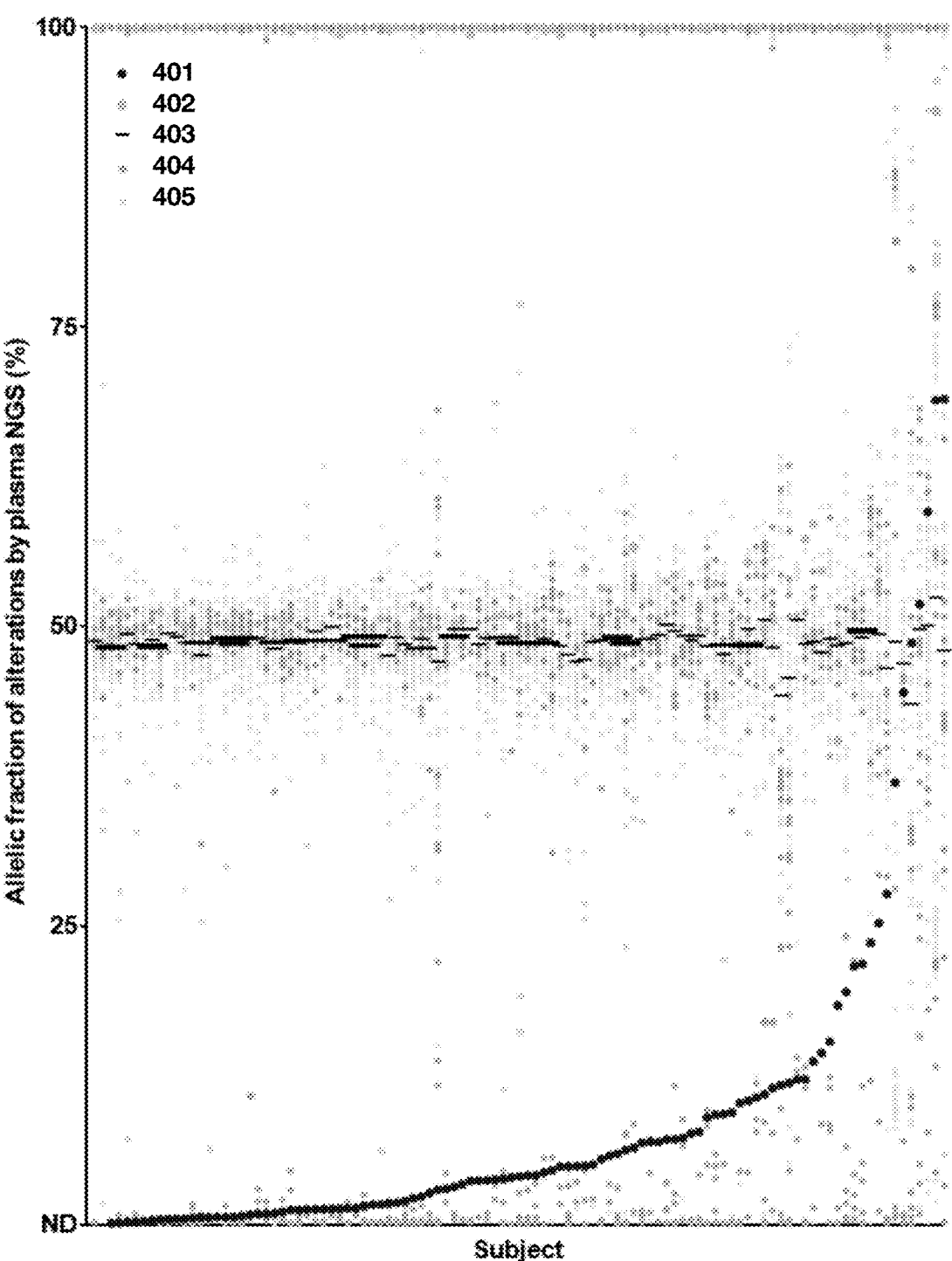
FIG. 4A shows the AF of all variants found on plasma NGS of 105 cases positive for EGFR mutations, in increasing order of EGFR driver mutation AF (401—black dots), with a common EGFR SNP shown (402—larger grey dots).
Figure 4B:
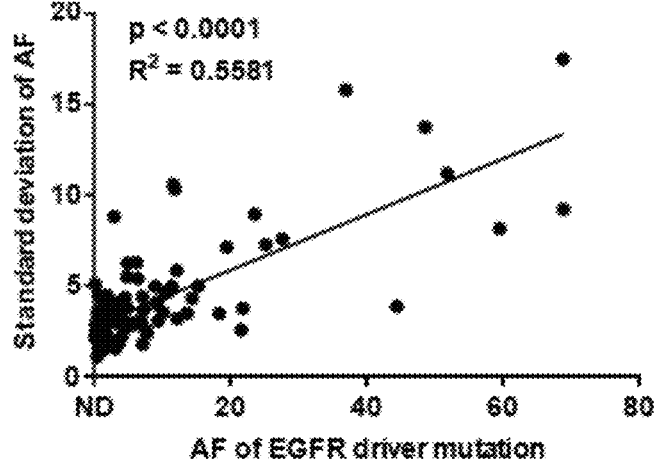
FIG. 4B shows that, for variant AFs between 25% and 75%, the standard deviation and absolute difference between case and population mean increase with an increase in EGFR driver AF.
Figure 4B:
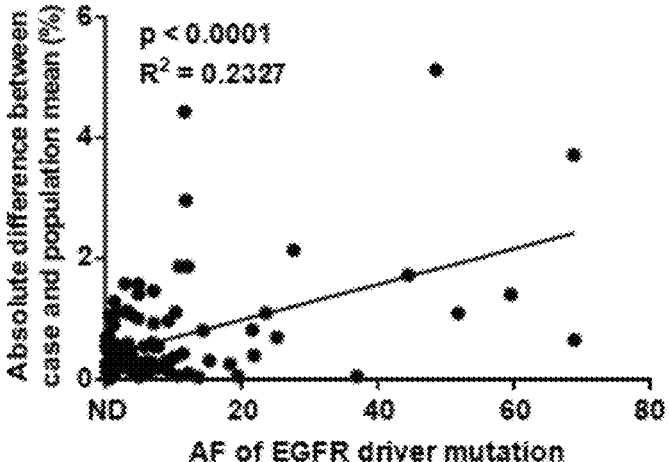
Figure 8A:
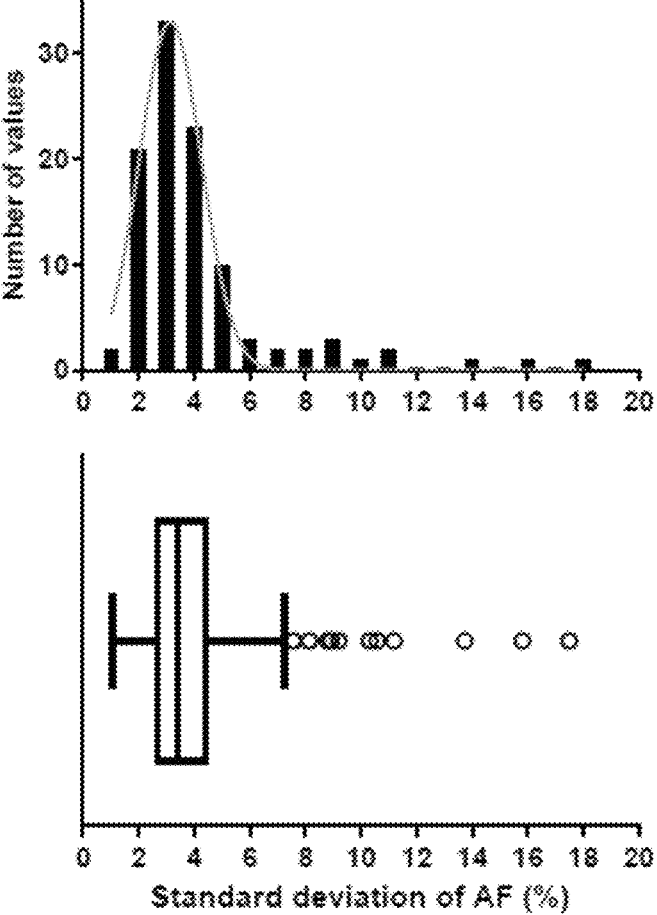
FIG. 8A shows that a curve can be fit for the standard deviation, even with outliers present.
Figure 8B:
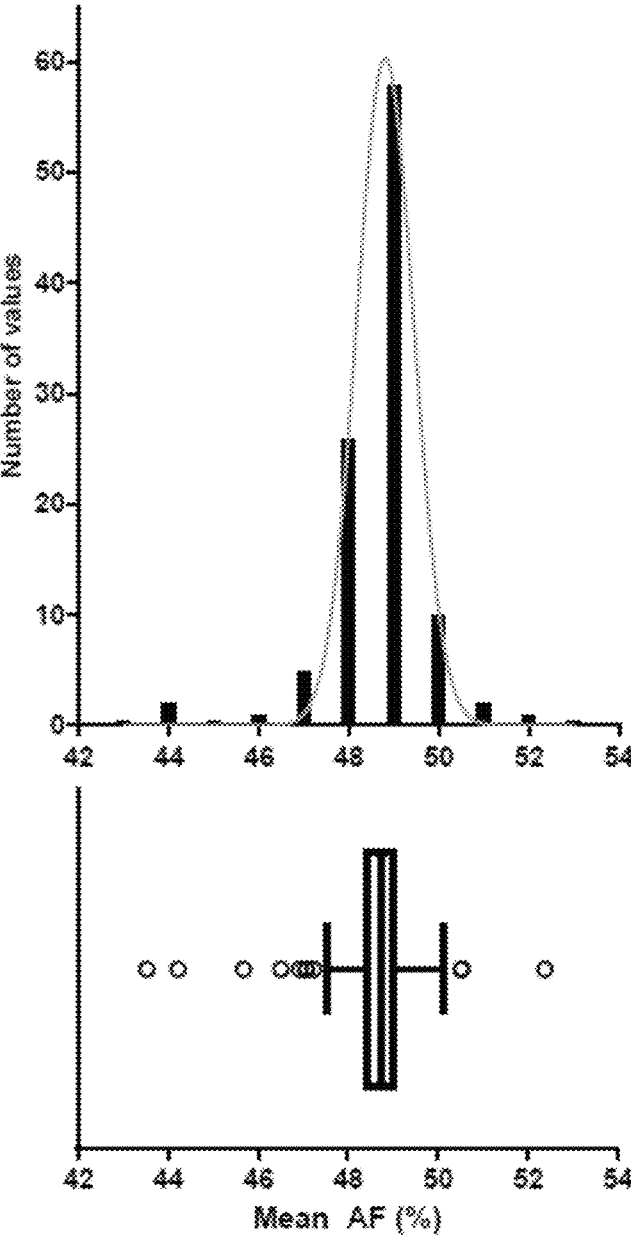
FIG. 8B shows that a curve can be fit for the mean, even with outliers present.

To study the relationship between potential germline and somatic variants, each plasma NGS case was plotted individually in order of low to high AF of the EGFR driver mutations (FIG. 4A, where 401 (black dot) is EGFR driver mutation; 402 (bigger grey dot) is EGFR Q787Q (known SNP); 403 is mean of heterozygous band; 404 (middle size grey dot) is other coding alterations and 405 (smaller grey dot) is non-coding alterations). While AF of the driver mutation is not a perfect measure of tumor content in cfDNA (due to the presence or absence of EGFR gene amplification in some cases) it can serve as an estimate of tumor content in cfDNA across a cohort. Studying the distribution of variant AFs in the heterozygous group, here designated as all variants with an AF between 25% and 75%, the distribution changed as the AF of the EGFR driver mutation increased. An increase in EGFR driver AF was associated with an increased standard deviation of the heterozygous group (FIG. 4B) as well as an increase in the absolute difference between the case and the population mean, both of which suggest the presence of cancer-derived copy number variation. Studying the standard deviation of the AF of the variants in the heterozygous group, a normal distribution was fit to 94 cases, while 11 cases had outlier characteristics (FIG. 8A). Similarly, studying the median of the AF for the variants in the heterozygous group, a normal distribution was fit to 94 cases while 11 cases had outlier characteristics (FIG. 8B). Because these outlier populations overlapped, 16 cases in total exhibited one of these two outlier characteristics with evidence of high copy number variation in cfDNA, which may have been due to high levels of tumor DNA causing variability in the AF of germline variants.

Figure 5:
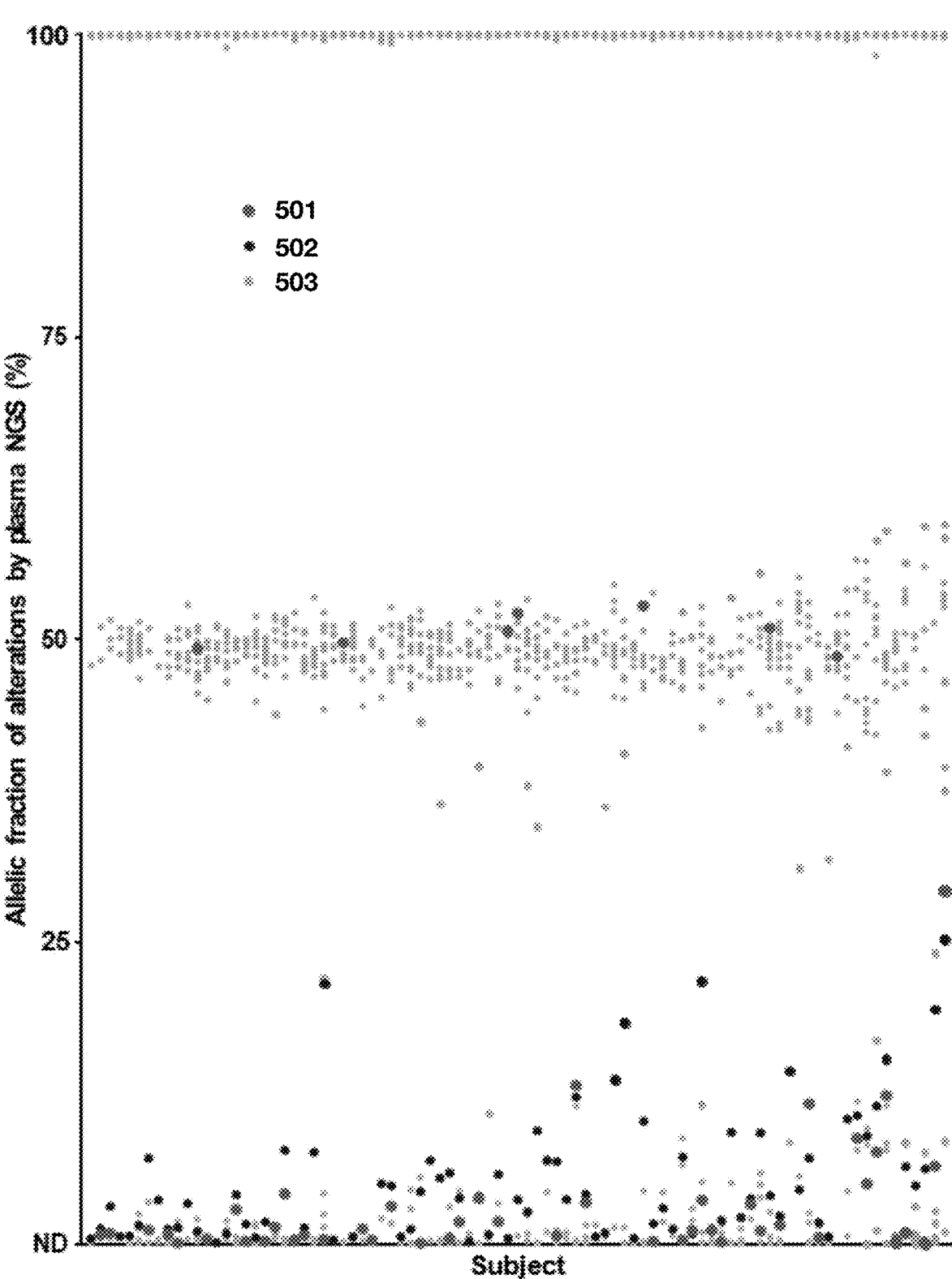
FIG. 5 shows the distinction between heterozygous and tumor-derived coding variants in cases with low copy number variation.

Because the high copy number variation can result in substantial deviation of the AF of germline variants from the expected 50%, germline-somatic discrimination could be impaired in these outlier cases. Thus, these 16 outlier cases were segregated from the 89 cases without outlier characteristics (FIG. 5). With visual review of the coding variants of outlier cases, it can be challenging to distinguish a clear separation between germline heterozygous variants and somatic cancer-derived variants, but by contrast, visual review of the coding variants of cases without these characteristics of high copy number variation (FIG. 5, where 501 (bigger grey dot) is EGFR T790M; 502 (black dot) is EGFR driver mutation and 503 (smaller grey dot) is other coding alterations), allows for the clear distinction of a group of heterozygous variants with AFs in the range of 35 to 60%, which are non-overlapping with a group of cancer-derived variants with AFs below 30%. Thus, by excluding plasma NGS cases with high copy number variation (and thus high tumor content), plasma NGS results can be accurately differentiated into somatic variants within the cancer-derived group and incidentally identified germline risk alleles within the heterozygous group.

Following the logic of these proof-of-concept studies, an integrated bioinformatics algorithm was developed and evaluated to segregate germline and somatic alterations across the 70 genes assayed using plasma NGS. This algorithm first assigned variants a presumed germline or somatic origin using a priori knowledge, including both internal and external databases of known germline and somatic variants (pathogenic and benign). For example, the EGFR Q787Q alteration is a benign polymorphism present in ~52% of germline exomes in the ExAC database, allowing this to be designated as of presumed germline origin regardless of allelic fraction. Conversely, the EGFR L858R alteration is a relatively common oncogenic mutation in NSCLC but does not appear in germline databases, allowing this to be designated as of presumed somatic origin. Such a priori binning usually results in a median of 78 variants per case being assigned as germline, which allows construction of a heterozygous probability distribution by variant AF as described in the studies above. If all presumed somatic mutations (generally fewer in number) are present below the lower limit of this heterozygous germline distribution, germline-somatic discrimination of the remaining unassigned variants proceeds according to their AF relative to the germline distribution described by a priori variant classification. However, if the AF of presumed somatic variants exceed the AF of the lower limit of the heterozygous germline distribution, or if extreme chromosomal instability is detected (as assessed by the apparent diploid fraction of the genome), germline/somatic discrimination is deemed uncertain for the variants remaining within that region of overlap, and variants are presumed to be somatic in origin and reported as such. This approach allows identification of suspected germline variants with a high positive predictive value, understanding that sensitivity for variants of germline origin will be reduced in settings of high tumor DNA content.

Figure 9:
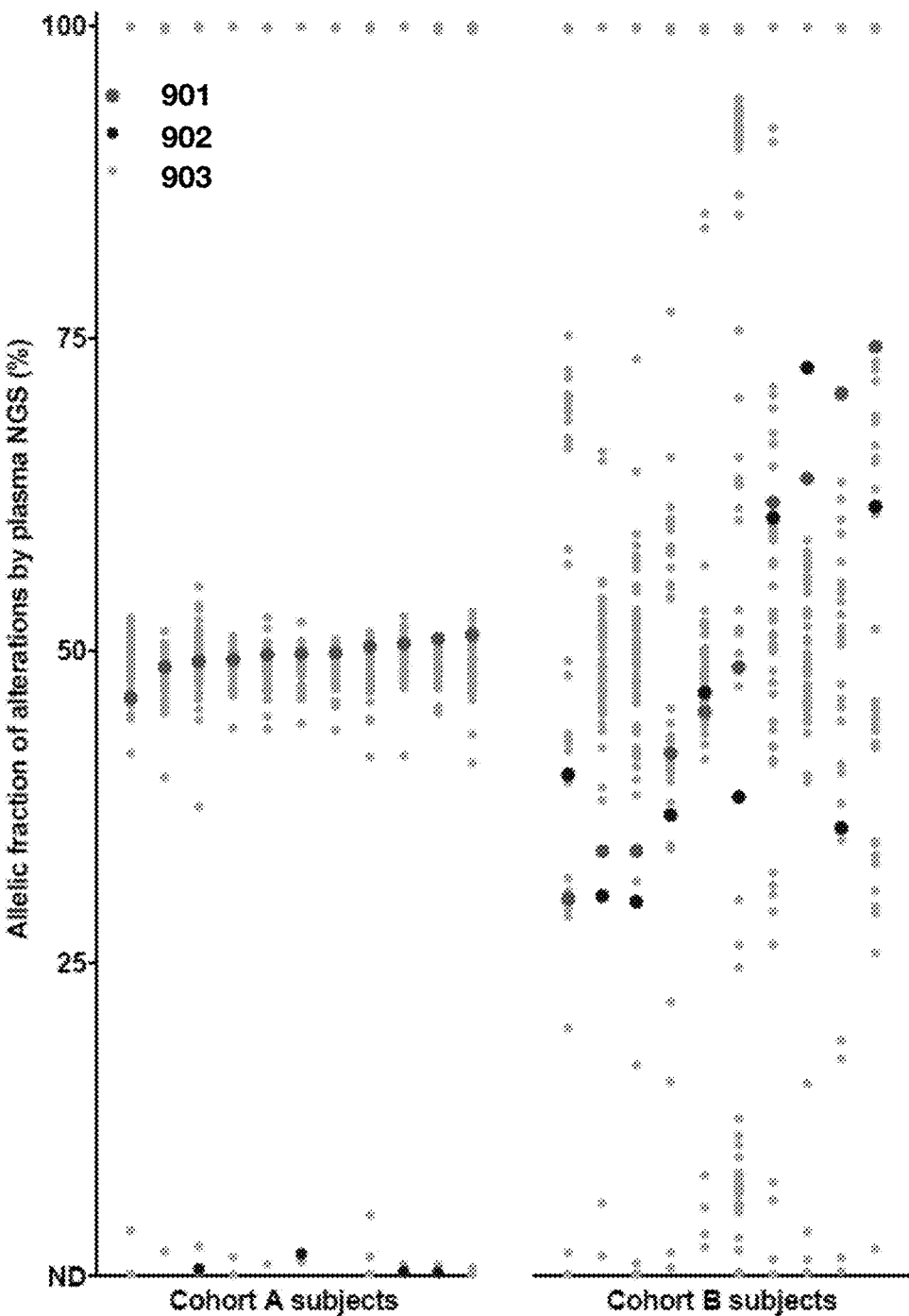
FIG. 9 shows that, among 11 plasma NGS cases (Cohort A) designated with low copy number variation and high AF of EGFR T790M (left), all 11 were confirmed to be germline (100% positive predictive value). Among 10 cases (Cohort B) with high copy number variation and high AF of EGFR T790M (right), one was positive for a germline T790M mutation.

This algorithm was then applied to 21 Prospectively collected clinical samples with high AF (30%-75%) EGFR T790M mutations detected on plasma NGS (FIG. 9, where 901 (bigger grey dot) is EGFR T790M; 902 (black dot) is EGFR driver mutation and 903 (smaller grey dot) is other coding alterations). Cases were segregated into two cohorts based upon the germline-somatic segregation of EGFR T790M described above. Cohort A included 11 cases in which the distribution of somatic vs. germline derived variants led to the prediction of a germline T790M mutation being present. Cohort B included 10 cases in which determination of germline vs. somatic was complicated due by high copy number variation and a broad heterozygous group. The genomic DNA-containing cellular fractions of each sample were then irreversibly de-identified and submitted to a CLIA-certified clinical laboratory for EGFR sequencing in a double-blinded manner such that no germline result was traceable to any individual patient. All 11 cases in cohort A were confirmed to harbor a germline EGFR T790M (positive predictive value 100%, 11/11). Of 10 cases in cohort B, one was found to be germline, resulting in a sensitivity of 92% (11/12) and an overall accuracy of 95% (20/21). The presence of a germline sample in Cohort B was suspected to be a case with high tumor content such that the AF of presumed somatic mutations overlapped with heterozygous germline distribution, making it difficult to discriminate germline variants with certainty.

Figure 6B:
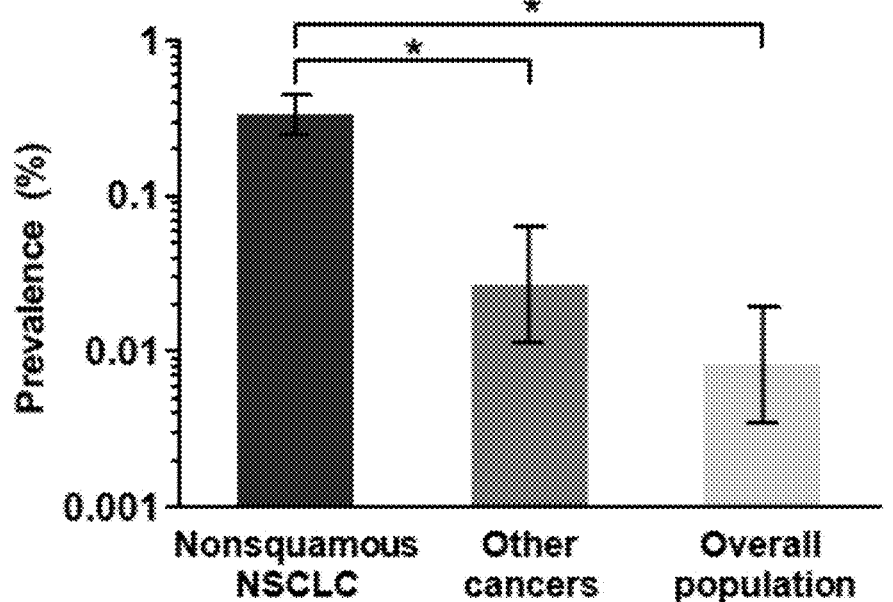
FIG. 6B shows that, as compared to the population prevalence of germline EGFR T790M in a reference cohort (0.008%), there is a higher prevalence in subjects with nonsquamous NSCLC (0.34%) but not in subjects with other cancers (0.03%, p=0.06), suggesting that germline EGFR T790M is a risk variant for lung cancer.

Having validated a method for identifying plasma NGS cases which carry germline EGFR T790M, existing plasma NGS data were used to learn about the association of germline variants with specific cancer types. A clinical testing database of 31,414 consecutive unique patients representing a wide variety of adult solid tumor types was queried to identify 911 cases positive for EGFR T790M, of which 48 were of germline origin as adjudicated by the above methodology. Though non-squamous NSCLC was the cancer diagnosis in a minority of the overall patient cohort (41%), this was the cancer diagnosis in 43 of the 48 patients with germline EGFR T790M (90%, FIG. 6A). Moreover, of the remaining 5 patients with germline EGFR T790M, three had a related diagnosis (squamous NSCLC, small cell lung cancer, carcinoma of unknown primary). The population frequency of germline EGFR T790M in patients with non-squamous NSCLC (43/12,774, 0.34%) was substantially higher than was seen in patients with another cancer diagnosis (5/18,640, 0.03%, FIG. 6B), the latter being only moderately higher than that reported by general population sequencing efforts (e.g. ExAC's median allele frequency of 0.0082%). These observations are congruent with the concept that patients with germline T790M are at increased risk specifically for NSCLC, and they suggest that this allele does not confer substantially increased risk of other cancers aside from lung cancer.

The above analyses demonstrate the power of cfDNA genomics as a tool for investigation of germline cancer risk alleles. Using existing data and samples from ongoing clinical research efforts, a bioinformatic algorithm was developed and validated for to distinguishing germline variants from cancer-derived somatic variants within cfDNA NGS profiles, providing a single assay that can offer insight into tumor genotype for therapy selection as well as screen for hereditary risk alleles. A clinical testing database was queried to explore the rare germline allele, EGFR T790M, and enrichment for this mutation was observed in patients with nonsquamous NSCLC. The above data highlight the ability of plasma genotyping, currently used for routine clinical care, to detect germline variants and, in certain circumstances differentiate them from somatic variants.

---

What is claimed is:

1. A method of identifying a germline origin or a somatic origin of a genetic variant comprising:

allocating a read budget of sequence reads that specifies a first number of sequence reads directed to a backbone sub-panel that interrogates a plurality of backbone genomic loci and a second number of sequencing reads directed to a hotspot sub-panel that interrogates a plurality of hotspot genomic loci, wherein the second number is selected to achieve a user-defined lower-limit-of-detection;

a) receiving, from a sequencer, sequence data indicative of a plurality of sequence reads of cfDNA molecules generated in accordance with the allocated read budget, wherein the sequence data comprises sequence data for the plurality of backbone genomic loci and the plurality of hotspot genomic loci;

b) processing, using a computer, the sequence data to:

(i) for each of the plurality of backbone genomic loci, obtain an allele fraction (AF) measure and a measure of AF variability, (ii) bin the plurality of backbone genomic loci based on a presumed origin, and (iii) using the AF measures and the measures of AF variability of the binned plurality of backbone genomic loci, determine an AF variability threshold such that backbone genomic loci of the binned plurality of backbone genomic loci having AF variability above the AF variability threshold are designated high copy number loci and backbone genomic loci of the binned plurality of backbone genomic loci having AF variability below the AF variability threshold are designated low copy number loci and an AF threshold that separates germline from somatic AF distributions associated with the backbone genomic loci of the binned plurality of backbone genomic loci designated as the low copy number loci;

c) for a variant detected at any hotspot genomic locus of the plurality of hotspot genomic loci, obtaining, using a computer, a variant AF and a variant AF variability, and comparing the variant AF variability against the AF variability threshold to identify the variant with the measure of variant AF variability below the AF variability threshold as having low copy number; and d) based on the variant having a low copy number, identifying germline origin or somatic origin for the variant by comparing, using a computer, the variant AF against the AF threshold, wherein, the variant is germline origin if the variant AF is above the AF threshold, and the variant is somatic origin if the variant AF is below the AF threshold.

2. The method of claim 1, further comprising identifying a copy number variation (CNV) level, wherein said measure of AF variability for a genomic locus below said AF variability threshold indicates a low CNV for said genomic locus, and wherein said measure of AF variability for a genomic locus above said AF variability threshold indicates a high CNV for said genomic locus.

3. The method of claim 1, wherein the AF threshold is derived from a second AF measure of a variant of a known origin, wherein said known origin is (i) somatic or (ii) germline.

4. The method of claim 3, wherein said second AF measure is derived from said sequence data for a second genomic locus from said plurality of backbone genomic loci.

5. The method of claim 3, wherein said second AF measure is derived from a genomic locus from cfDNA from a control subject.

6. The method of claim 3, wherein d) comprises identifying said variant as being of the same origin as said known origin, if there is a difference of 10% or less between the variant AF and the AF threshold.

7. The method of claim 1, further comprising assigning a presumed origin of each locus of said plurality of backbone genomic loci, wherein said presumed origin is one of: (i) presumed somatic origin, (ii) presumed germline origin, and (iii) presumed indeterminate origin.

8. The method of claim 7, wherein binning said plurality of backbone genomic loci based on said presumed origin, generates a first bin comprising genomic loci of presumed somatic origin, a second bin comprising genomic loci of presumed germline origin, and a third bin comprising genomic loci of indeterminate origin;

and determining, for one or more genomic regions in each of the first bin, the second bin, and the third bin, a quantitative AF measure for one or more loci in each of the one or more genomic regions based on cfDNA sequencing reads to generate a first AF set, a second AF set, and a third AF set, respectively.

9. The method of claim 8, wherein the AF threshold is determined by:

(a) generating a first frequency distribution based on said first AF set and a second frequency distribution based on said second AF set, wherein no overlap exists between said first frequency distribution and said second frequency distribution;

(b) identifying the AF threshold based on said first and second frequency distributions, which AF threshold is (i) no less than the largest quantitative AF measure among said first AF set and (ii) no more than the smallest quantitative AF measure among said second AF set.

10. The method of claim 8, wherein the AF threshold is determined by (i) generating a first frequency distribution based on said first AF set and a second frequency distribution based on said second AF set, wherein an overlap exists between said first frequency distribution and said second frequency distribution and (ii) identifying the AF threshold based on said first and second frequency distributions, which the AF threshold is the largest quantitative AF measure among said first AF set;

wherein the method further comprises identifying a second AF threshold based on said first and second frequency distributions, which second AF threshold is the smallest quantitative AF measure among said second AF set; and wherein d) comprises identifying each backbone genomic locus of the plurality of backbone genomic loci as:

(A) somatic origin if said AF measure is no more than the AF threshold, (B) germline origin if said AF measure is no less than said second AF threshold, or (C) ambiguous if said AF measure is greater than the AF threshold and less than the second AF threshold.

11. The method of claim 1, wherein said measure of variability is a standard deviation of said AF measure.

12. The method of claim 1, wherein a genomic locus is selected from a member of the group consisting of BRAF, BRCA1, BRCA2, EGFR, KRAS, PIK3CA, ROS1, and TP53.

13. The method of claim 1, further comprising prior to a), providing a plurality of cfDNA molecules.

14. The method of claim 13, further comprising amplifying said plurality of cfDNA molecules.

15. The method of claim 13, further comprising enriching for a subset of said plurality of cfDNA molecules, wherein said subset comprises cfDNA molecules comprising a sequence of a genomic region of interest.

16. The method of claim 13, further comprising tagging said plurality of cfDNA molecules.

17. The method of claim 13, further comprising sequencing said cfDNA molecules to generate said sequence reads of cfDNA.

18. The method of claim 1, further comprising aligning said set of sequence reads to a genetic locus.

19. The method of claim 1, further comprising mapping said sequence reads to a reference genome.

20. The method of claim 1, wherein binning comprises use of a computer database.

21. The method of claim 1, comprising obtaining a sample and generating a set of at least 1 million sequence reads.

22. The method of claim 1, comprising a read depth of about 5,000×.

23. The method of claim 1, comprising a read depth of about 10,000×.

24. The method of claim 1, comprising a read depth of about 20,000×.

25. The method of claim 1, wherein a targeted-sequencing panel comprises the backbone sub-panel and the hotspot sub-panel and encompasses a plurality of genes or genomic regions such that a predetermined proportion of cancer patients exhibits a genetic variant in at least one region of the targeted-sequencing panel.

26. The method of claim 25, wherein capture probes for the targeted-sequencing panel comprise (i) probes directed to hotspot regions and (ii) nucleosome-aware probes that optimize capture efficiency based on cfDNA fragment-size variation and GC-content.

27. The method of claim 25, wherein the targeted-sequencing panel comprises a plurality of sub-panels comprising one or more of: (a) a tissue-of-origin sub-panel, (b) a whole-genome scaffold sub-panel, and (c) a transcription-start-site/CpG-island sub-panel.

28. The method of claim 1, wherein the read budget is between 100 million and 100 billion sequence reads.

29. The method of claim 1, wherein the plurality of backbone genomic loci are sequenced at a first average read depth and the hotspot loci are sequenced at a second, deeper average read depth.

30. The method of claim 1, wherein nucleic acids from two or more subjects are pooled and sequenced in a single run at ratios determined by amounts of nucleic acid obtained from each subject.

* * * * *